(12) United States Patent
Yamashita et al.

(10) Patent No.: US 9,506,910 B2
(45) Date of Patent: Nov. 29, 2016

(54) URINE COMPONENT ANALYSIS DEVICE

(71) Applicants: OMRON HEALTHCARE Co., Ltd., Muko-shi, Kyoto (JP); OMRON CORPORATION, Kyoto-shi, Kyoto (JP)

(72) Inventors: Hideyuki Yamashita, Kyoto (JP); Naoto Ohgami, Kyoto (JP); Yutaro Okuno, Kyoto (JP); Toshiyuki Iwahori, Muko (JP); Hirotsugu Ueshima, Kyoto (JP)

(73) Assignees: OMRON HEALTHCARE CO., LTD., Muko-shi (JP); OMRON CORPORATION, Kyoto-shi (JP)

( * ) Notice: Subject to any disclaimer, the term of this patent is extended or adjusted under 35 U.S.C. 154(b) by 0 days.

(21) Appl. No.: 14/173,453

(22) Filed: Feb. 5, 2014

(65) Prior Publication Data

US 2014/0150535 A1 Jun. 5, 2014

Related U.S. Application Data

(63) Continuation of application No. PCT/JP2012/061397, filed on Apr. 27, 2012.

(30) Foreign Application Priority Data

Aug. 5, 2011 (JP) ................................ 2011-172060

(51) Int. Cl.
   *G01N 33/50* (2006.01)
   *G01N 33/493* (2006.01)
   *G01N 33/84* (2006.01)

(52) U.S. Cl.
   CPC ............ *G01N 33/50* (2013.01); *G01N 33/493* (2013.01); *G01N 33/84* (2013.01)

(58) Field of Classification Search
   CPC ..... G01N 33/50; G01N 33/493; G01N 33/84
   See application file for complete search history.

(56) References Cited

U.S. PATENT DOCUMENTS

2010/0159606 A1  6/2010  Nakaminami et al.
2010/0247377 A1  9/2010  Tsutsumida et al.

FOREIGN PATENT DOCUMENTS

CN        101427133 A    5/2009
JP       A-2000-131316    5/2000

(Continued)

OTHER PUBLICATIONS

Office Action issued in Chinese Patent Application No. 201280038707.0 dated Oct. 27, 2014 (with translation).

(Continued)

*Primary Examiner* — Sam P Siefke
(74) *Attorney, Agent, or Firm* — Oliff PLC

(57) ABSTRACT

In a urine component analysis device, a correlation storage section stores data indicating a correlation between a measured concentration in one urine and in total urine in one day for each of a first and second specific component in the urine excreted by a human. A data input section inputs data indicating a concentration of the first specific component and of the second specific component in one urine of a subject. A concentration of the first specific component and of the second specific component in total urine in one day are determined by performing conversion using the correlation stored in the correlation storage section based on the concentration of the first specific component and the second specific component in the one urine. A concentration ratio between the first specific component and the second specific component in total urine in one day is determined based on the results of conversion.

30 Claims, 35 Drawing Sheets

(56) References Cited

FOREIGN PATENT DOCUMENTS

| JP | A-2001-249136 | 9/2001 |
| JP | A-2004-251670 | 9/2004 |
| JP | A-2005-24267 | 1/2005 |
| JP | A-2006-29819 | 2/2006 |
| JP | A-2006-126184 | 5/2006 |
| JP | B2-3823039 | 9/2006 |
| JP | A-2006-300657 | 11/2006 |
| JP | B2-4329123 | 9/2009 |
| JP | A-2010-8183 | 1/2010 |
| JP | A-2010-151826 | 7/2010 |
| JP | A-2010-236863 | 10/2010 |

OTHER PUBLICATIONS

International Search Report issued in International Application No. PCT/JP2012/061397 mailed Jun. 5, 2012.
English-language Translation of International Preliminary Report on Patentability issued in International Application No. PCT/JP2012/061397 issued Sep. 6, 2013.
Jun. 24, 2015 Office Action issued in Chinese Application No. 201280038707.0.
Dec. 24, 2015 Office Action issued in Chinese Application No. 201280038707.0.
Aug. 11, 2016 Decision of Rejection issued in Chinese Application No. 201280038707.0.

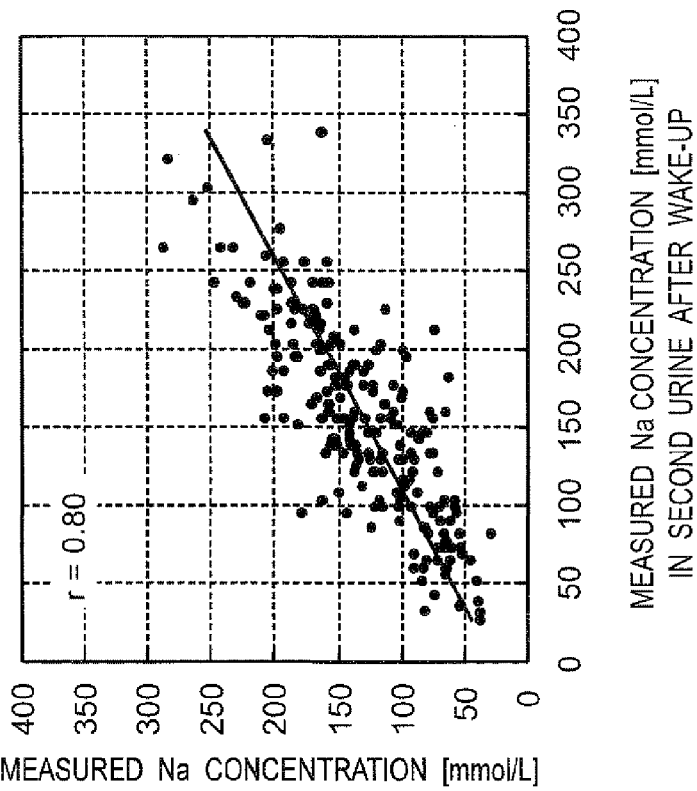
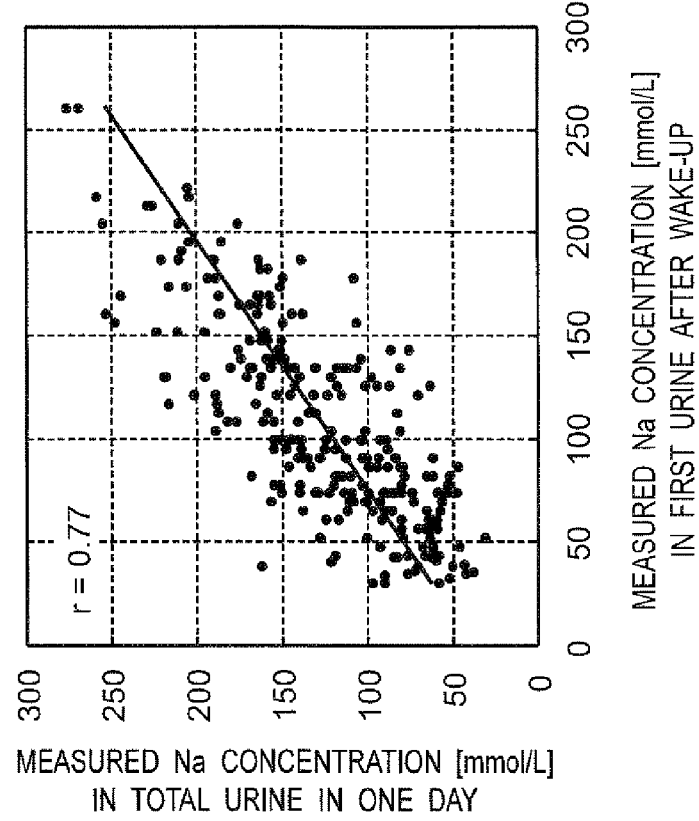
Fig. 5

Fig.6
CORRELATION BETWEEN K CONCENTRATION IN ONE URINE AND K CONCENTRATION IN TOTAL URINE IN ONE DAY
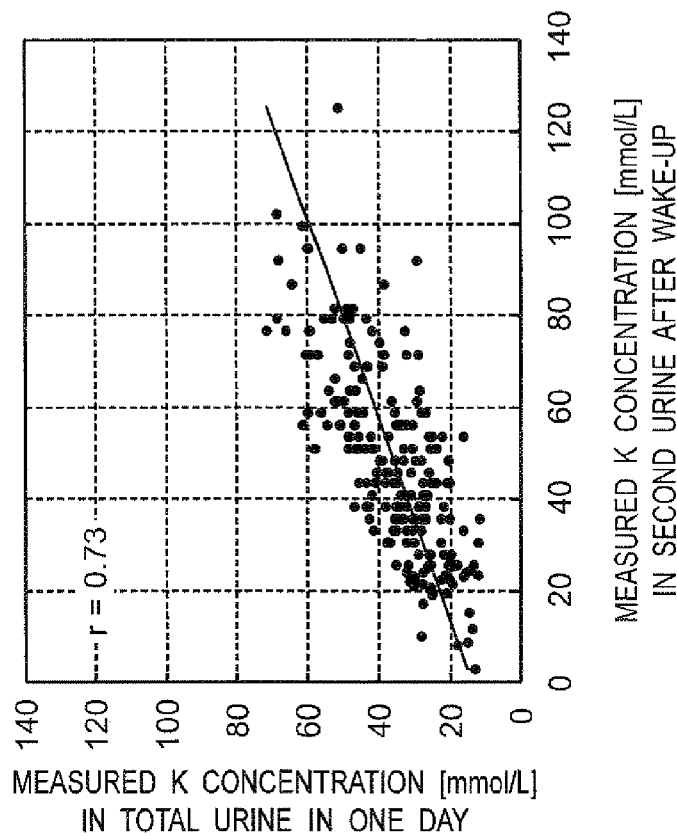
Fig.6A
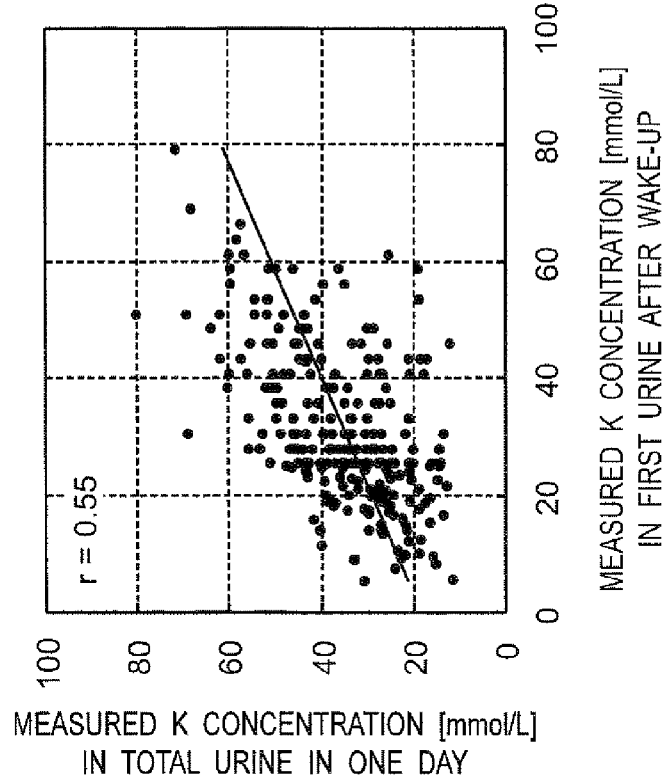
Fig.6B

Fig. 7
RESULT OF EXAMINATION WITH MEASURED Na/K RATIO IN TOTAL URINE IN ONE DAY
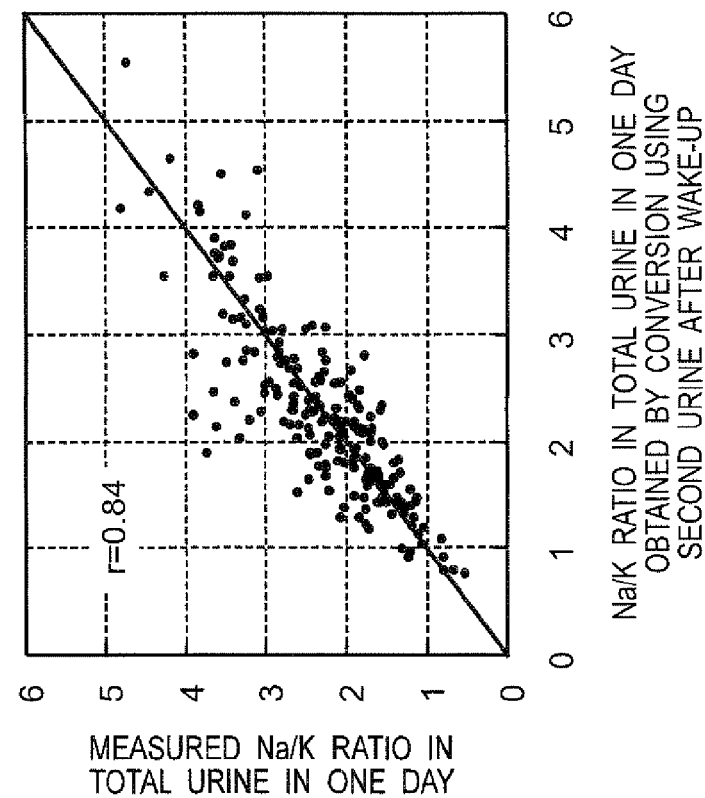
Fig. 7B
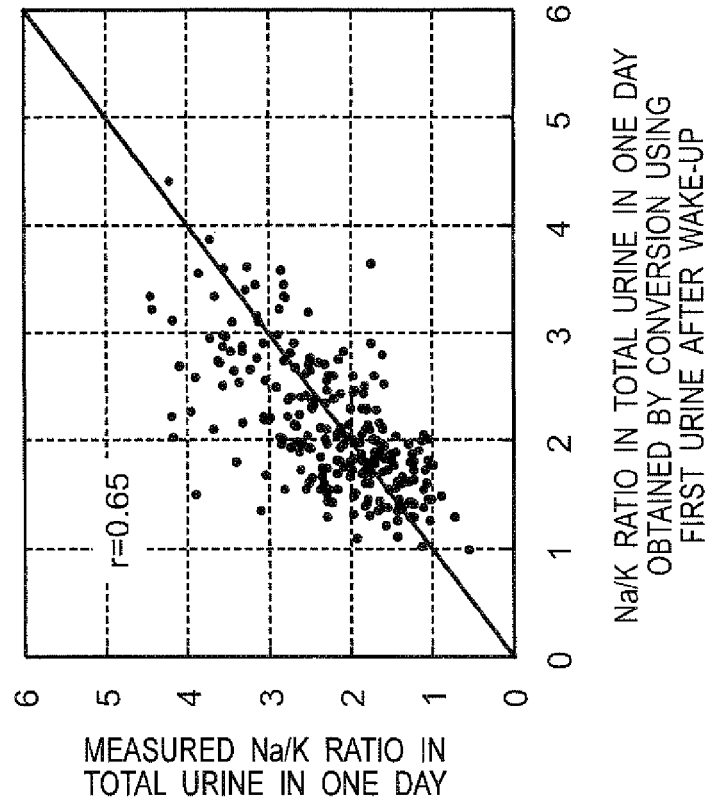
Fig. 7A Fig. 8
RESULT OF EXAMINATION WITH MEASURED DAILY Na/K RATIO IN TOTAL URINE
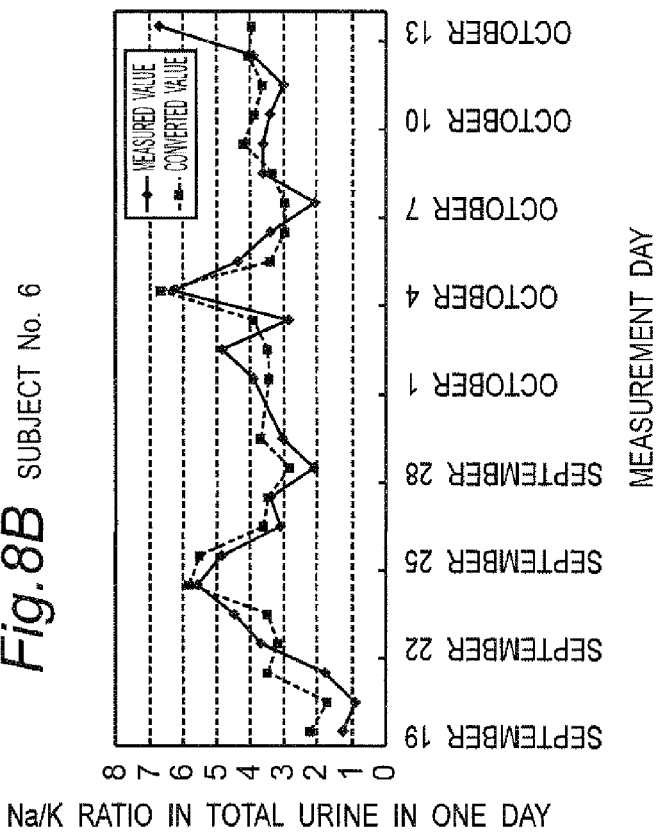
Fig.8B SUBJECT No. 6
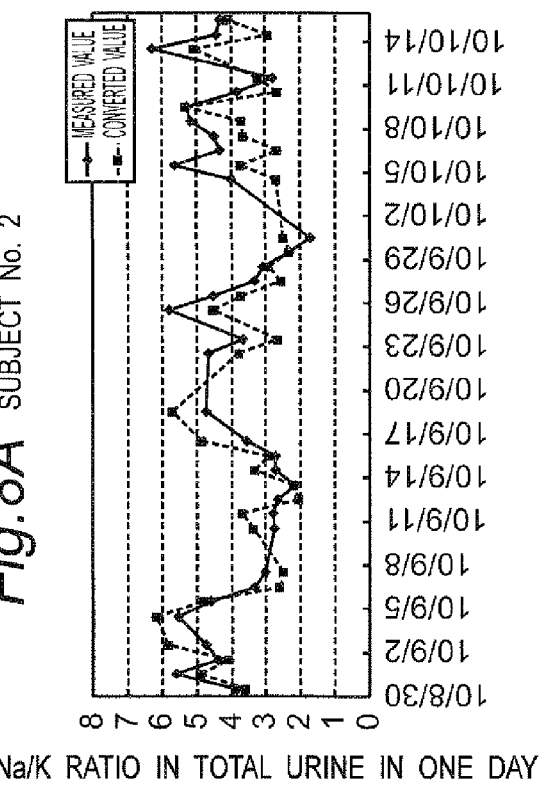
Fig.8A SUBJECT No. 2

Fig. 9
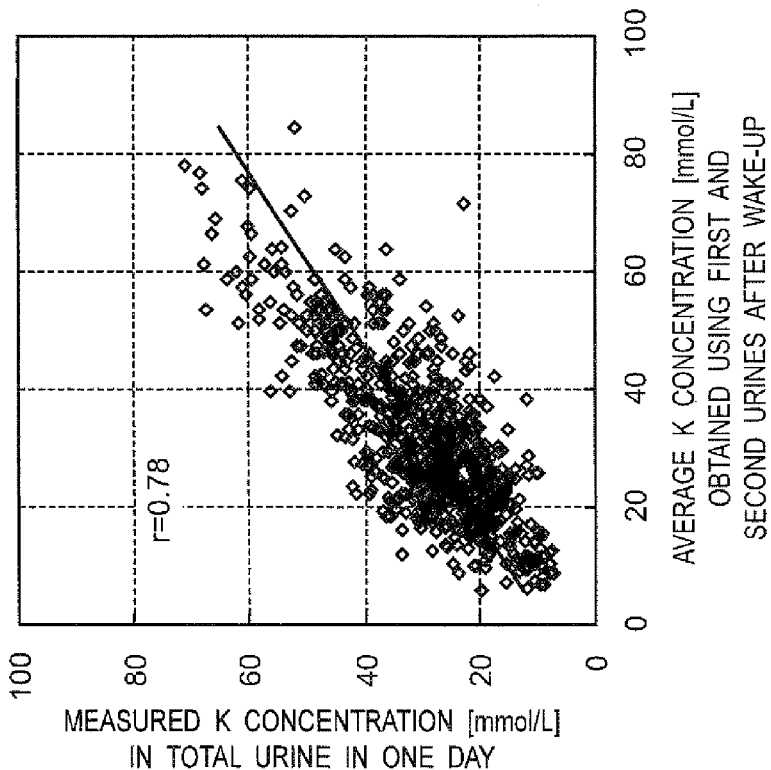
Fig. 9A
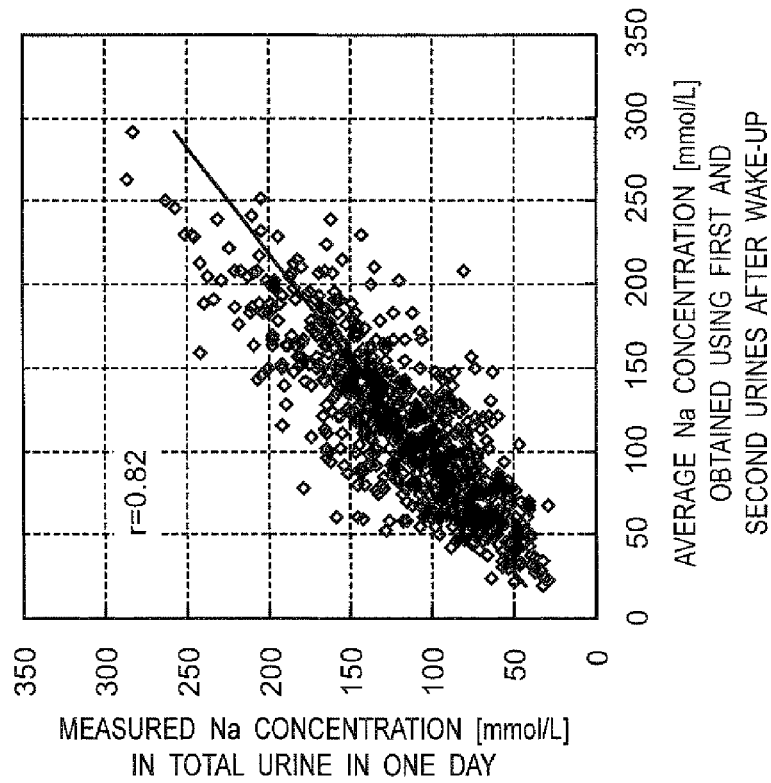
Fig. 9B

Fig. 10
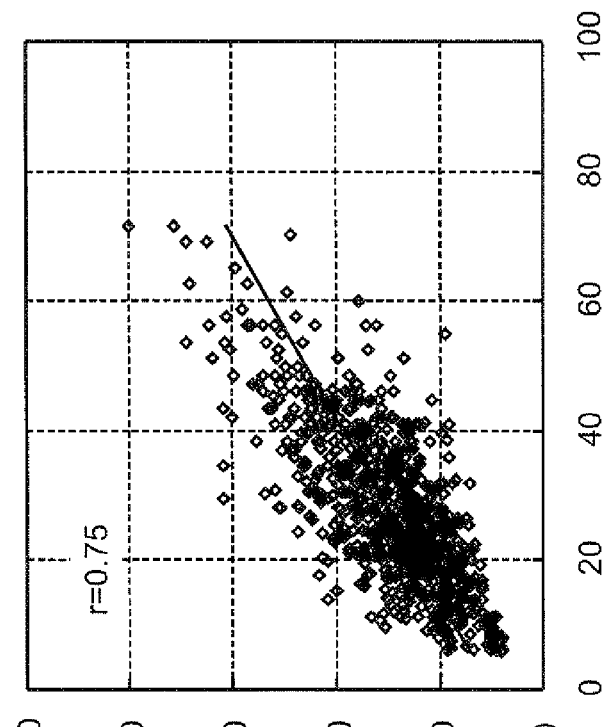
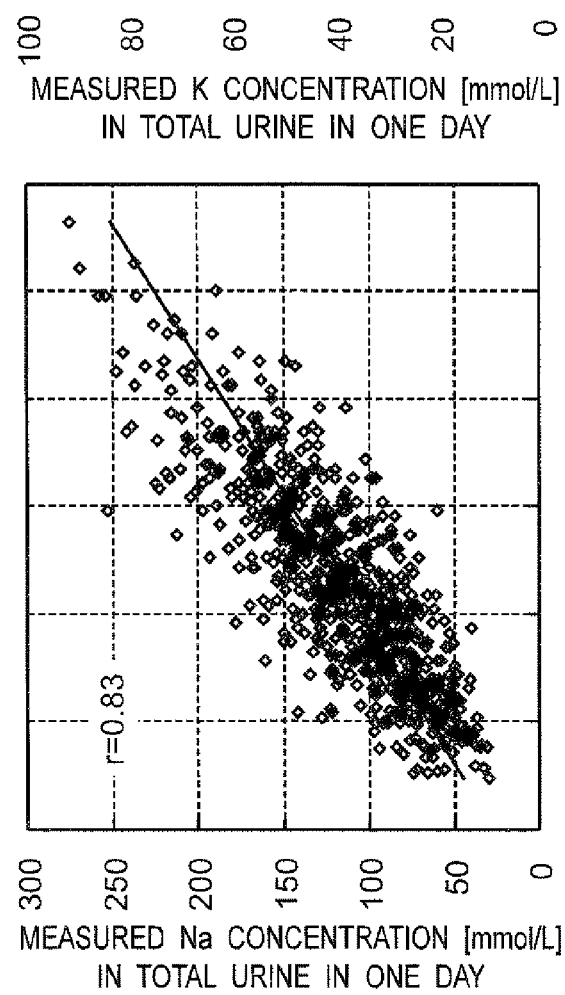

Fig. 11
RESULT OF EXAMINATION WITH MEASURED Na/K RATIO IN TOTAL URINE IN ONE DAY
Fig. 11A
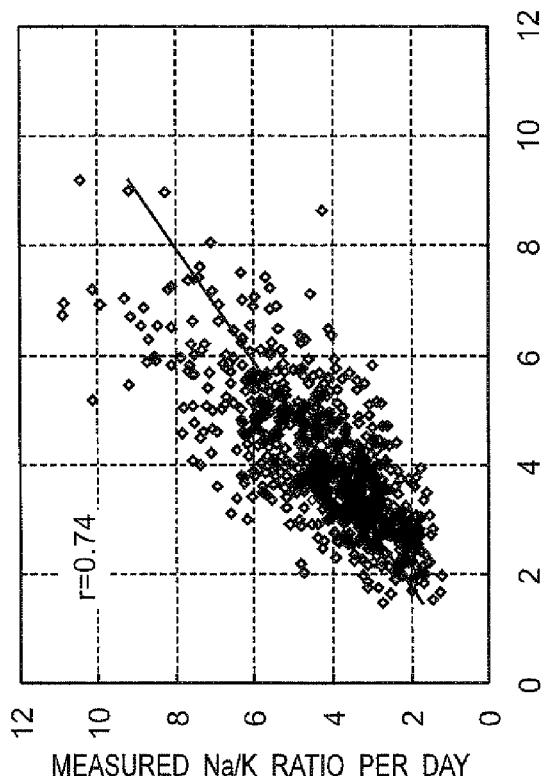
Fig. 11B
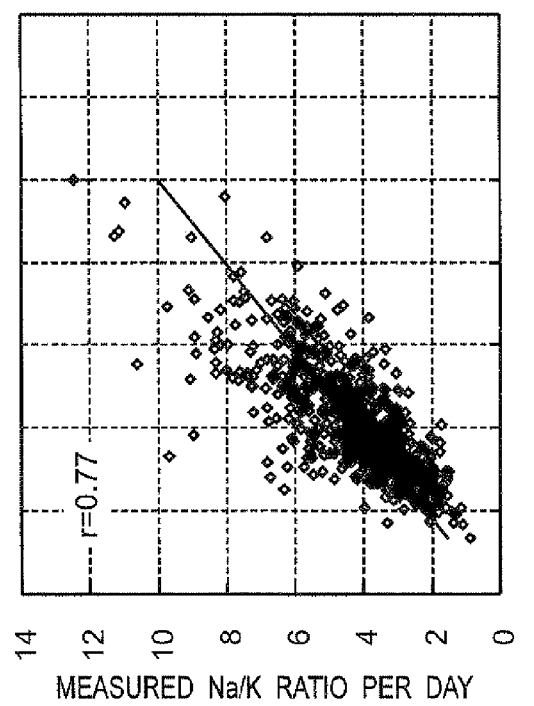

Fig. 14
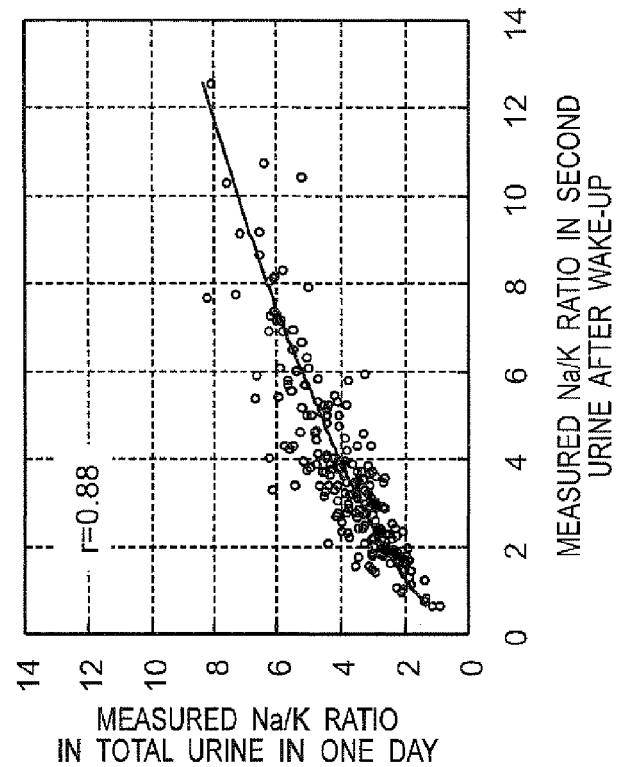
Fig. 14A
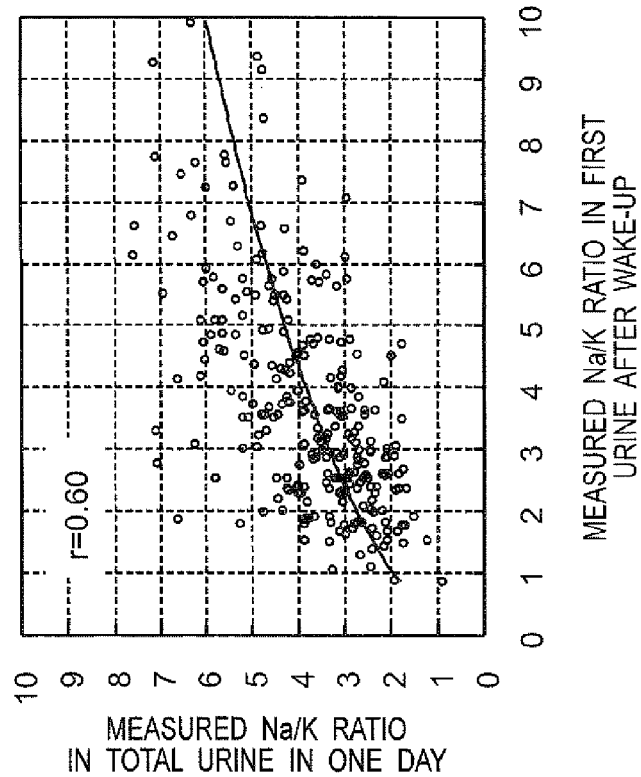
Fig. 14B

Fig. 15
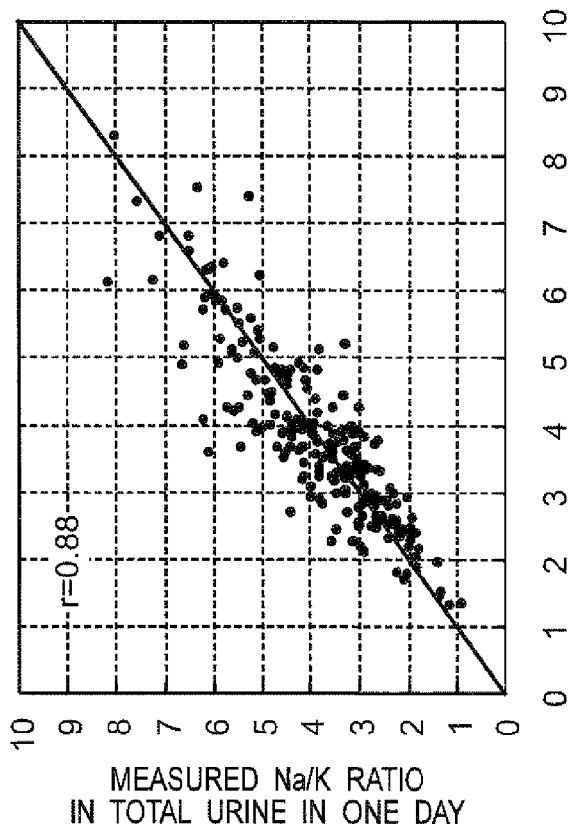
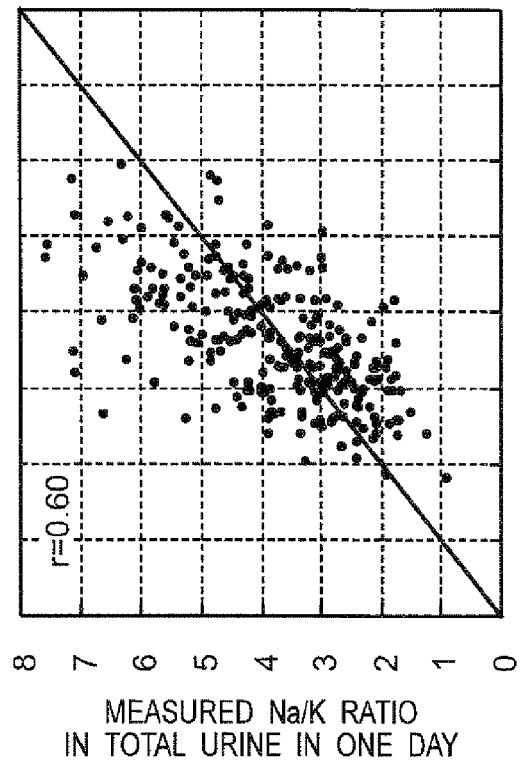

Fig.16
RESULT OF EXAMINATION WITH MEASURED DAILY Na/K RATIO IN TOTAL URINE
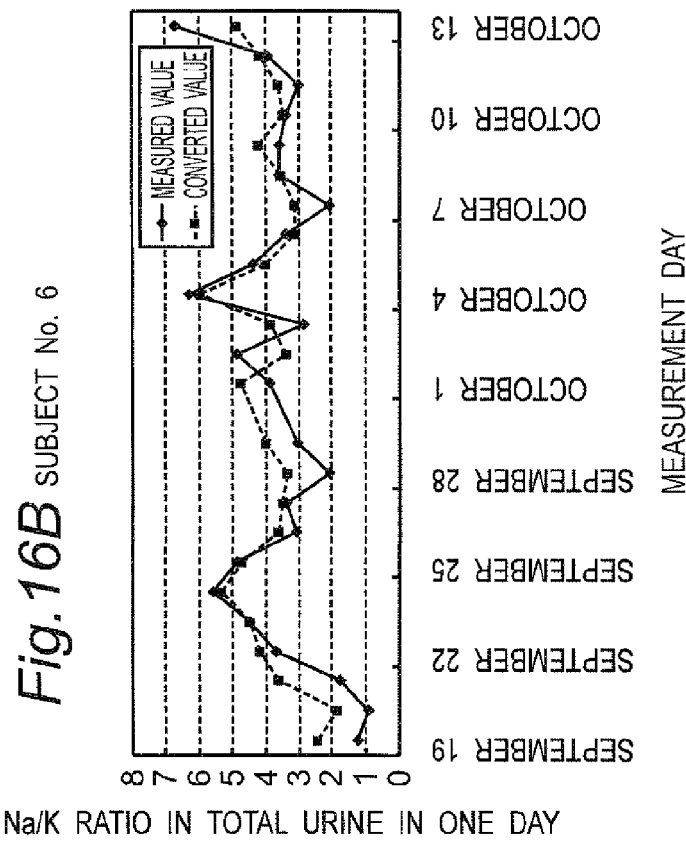
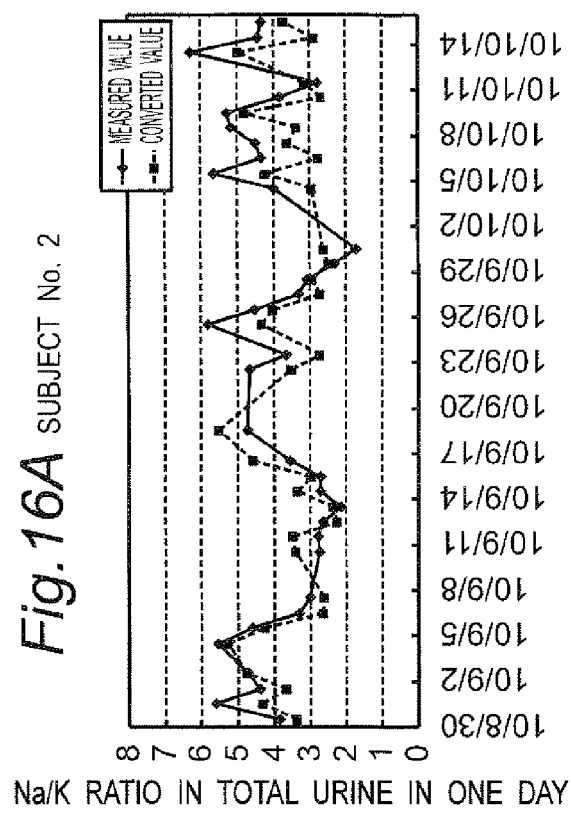

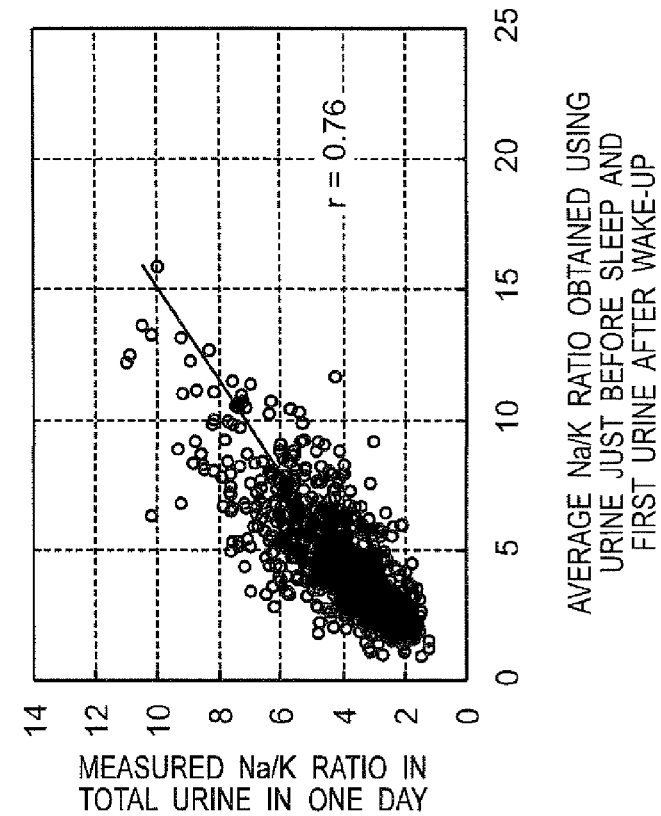
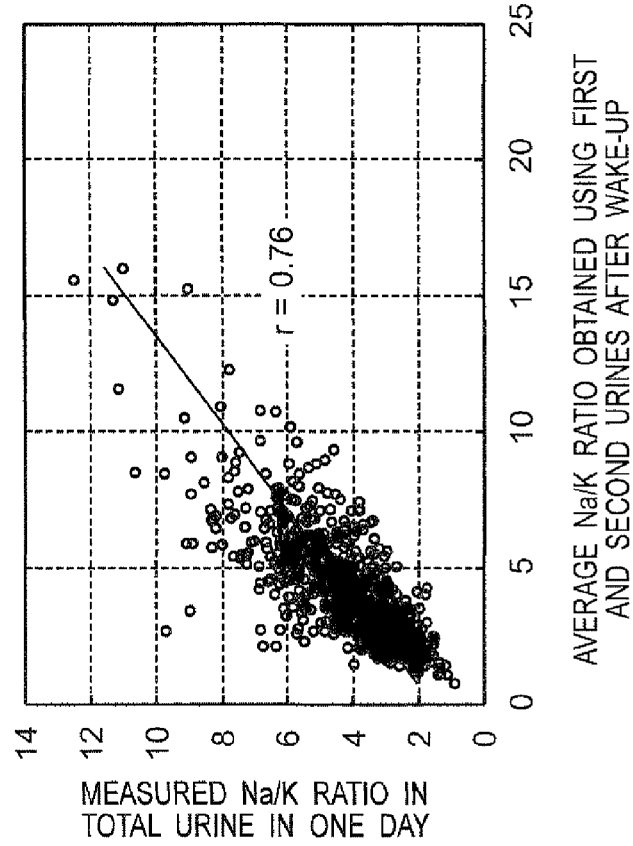
Fig. 17
Fig. 17A
Fig. 17B
CORRELATION BETWEEN Na/K RATIO OBTAINED USING TWO URINES AND Na/K RATIO IN TOTAL URINE IN ONE DAY

*Fig. 18*
CORRELATION 1 BETWEEN Na/K RATIO OBTAINED USING PLURAL URINES AND Na/K RATIO IN TOTAL URINE OVER PLURAL DAYS
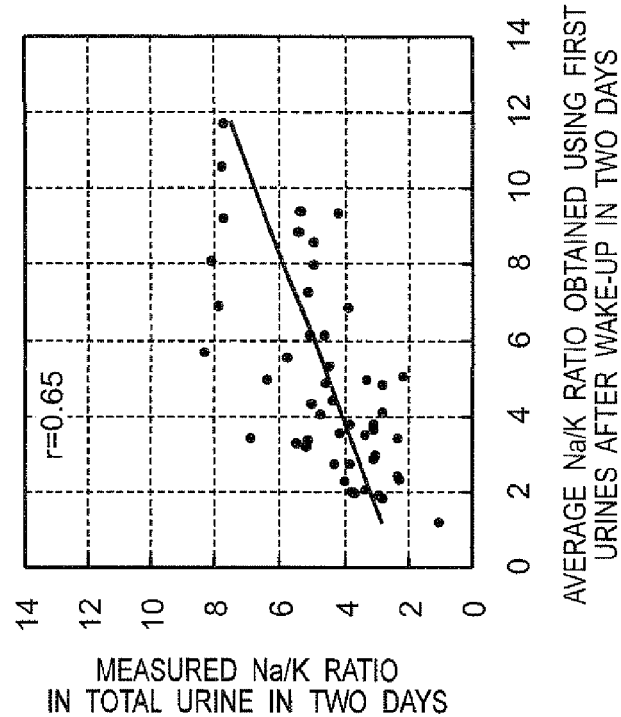
*Fig. 18B*
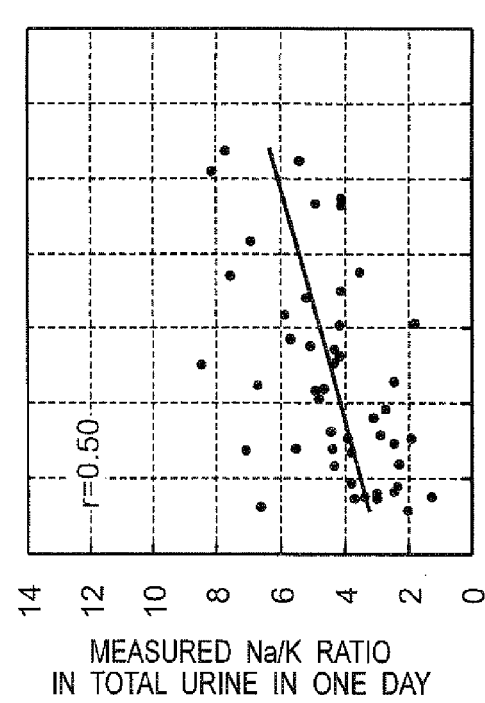
*Fig. 18A*

Fig. 19
CORRELATION 2 BETWEEN Na/K RATIO OBTAINED USING PLURAL URINES AND Na/K RATIO IN TOTAL URINE OVER PLURAL DAYS
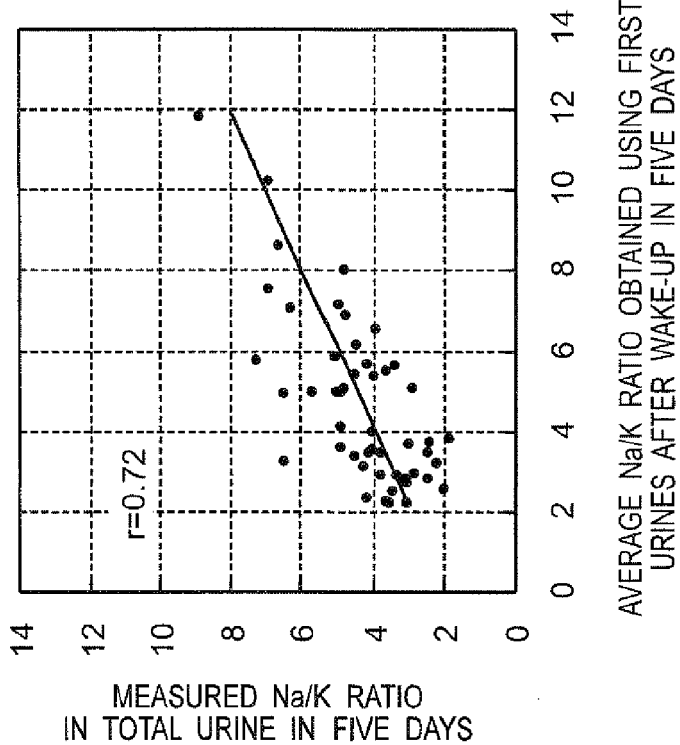
Fig. 19B
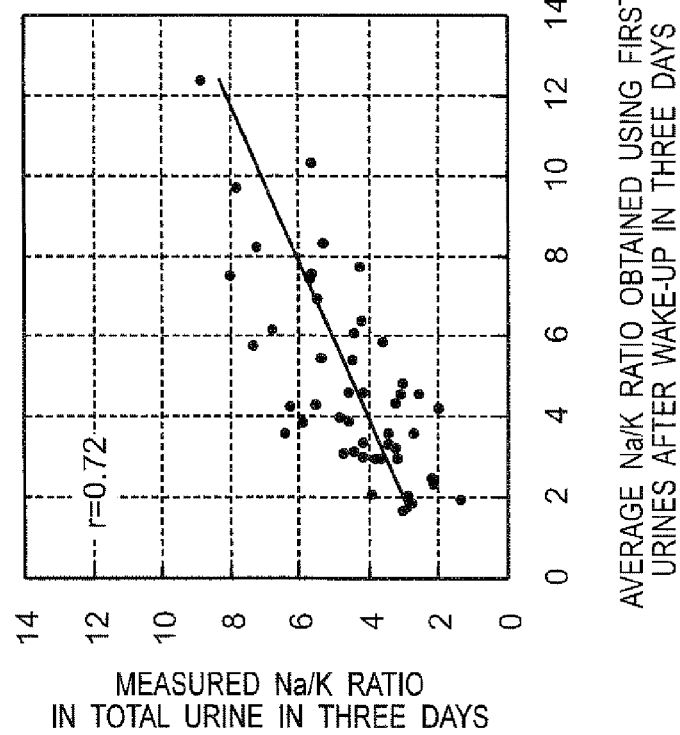
Fig. 19A

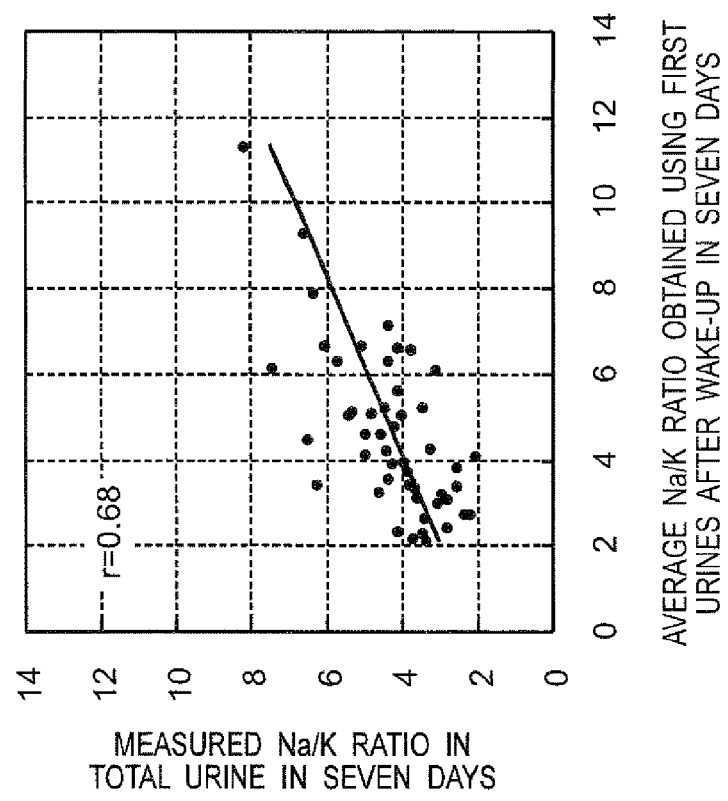

Fig.21

| Na/K RATIO | ADVICE |
|---|---|
| 0.0–1.0 | IDEAL VALUE |
| 1.0–2.0 | GOAL ACHIEVED |
| 2.0–2.5 | GOAL WILL BE ACHIEVED WITH A LITTLE EFFORT |
| 2.5–3.0 | VALUE HIGH AND TAKE CARE OF YOUR DIETARY LIFE |
| 3.0 OR MORE | VALUE SO HIGH. TAKE ENOUGH CARE OF YOUR DIETARY LIFE |

Fig.22

| Na/K RATIO | BLOOD PRESSURE | BMI | ADVICE |
|---|---|---|---|
| 0.0-1.0 | LESS THAN 135/85 mmHg | LESS THAN 25 | IDEAL VALUE FOR BOTH Na/K RATIO AND WEIGHT REDUCTION |
| | 135/85 mmHg OR MORE | 25 OR MORE | "IDEAL VALUE FOR Na/K RATIO. YOU NEED WEIGHT REDUCTION/EXERCISE AND MEDICATION" |
| | | LESS THAN 25 | GOAL ACHIEVED FOR Na/K RATIO AND WEIGHT REDUCTION. YOU NEED CONTINUOUS MEDICATION |
| 1.0-2.0 | LESS THAN 135/85 mmHg | LESS THAN 25 | GOAL ACHIEVED FOR BOTH Na/K RATIO AND WEIGHT REDUCTION |
| | 135/85 mmHg OR MORE | 25 OR MORE | "GOAL ACHIEVED FOR Na/K RATIO. YOU NEED WEIGHT REDUCTION/EXERCISE AND MEDICATION" |
| | | LESS THAN 25 | GOAL ACHIEVED FOR Na/K RATIO AND WEIGHT REDUCTION. YOU NEED CONTINUOUS MEDICATION |
| 2.0-2.5 | LESS THAN 135/85 mmHg | LESS THAN 25 | GOAL WILL BE ACHIEVED WITH A LITTLE EFFORT FOR Na/K RATIO. GOAL ACHIEVED FOR WEIGHT REDUCTION |
| | 135/85 mmHg OR MORE | 25 OR MORE | GOAL WILL BE ACHIEVED WITH A LITTLE EFFORT FOR Na/K RATIO. YOU NEED WEIGHT REDUCTION/EXERCISE AND MEDICATION" |
| | | LESS THAN 25 | GOAL WILL BE ACHIEVED WITH A LITTLE EFFORT FOR Na/K RATIO. GOAL ACHIEVED FOR WEIGHT REDUCTION/EXERCISE. YOU NEED CONTINUOUS MEDICATION |
| 2.5-3.0 | LESS THAN 135/85 mmHg | LESS THAN 25 | Na/K RATIO HIGH AND TAKE CARE OF YOUR DIETARY LIFE. GOAL ACHIEVED FOR WEIGHT REDUCTION |
| | 135/85 mmHg OR MORE | 25 OR MORE | Na/K RATIO HIGH AND TAKE CARE OF YOUR DIETARY LIFE. YOU NEED WEIGHT REDUCTION/EXERCISE AND MEDICATION" |
| | | LESS THAN 25 | Na/K RATIO HIGH AND TAKE CARE OF YOUR DIETARY LIFE. GOAL ACHIEVED FOR WEIGHT REDUCTION/EXERCISE. YOU NEED CONTINUOUS MEDICATION |
| 3.0 OR MORE | LESS THAN 135/85 mmHg | LESS THAN 25 | Na/K RATIO SO HIGH. TAKE ENOUGH CARE OF YOUR DIETARY LIFE. GOAL ACHIEVED FOR WEIGHT REDUCTION |
| | 135/85 mmHg OR MORE | 25 OR MORE | Na/K RATIO SO HIGH. TAKE ENOUGH CARE OF YOUR DIETARY LIFE. YOU NEED WEIGHT REDUCTION/EXERCISE AND MEDICATION" |
| | | LESS THAN 25 | Na/K RATIO SO HIGH. TAKE ENOUGH CARE OF YOUR DIETARY LIFE. GOAL ACHIEVED FOR WEIGHT REDUCTION/EXERCISE. YOU NEED CONTINUOUS MEDICATION |

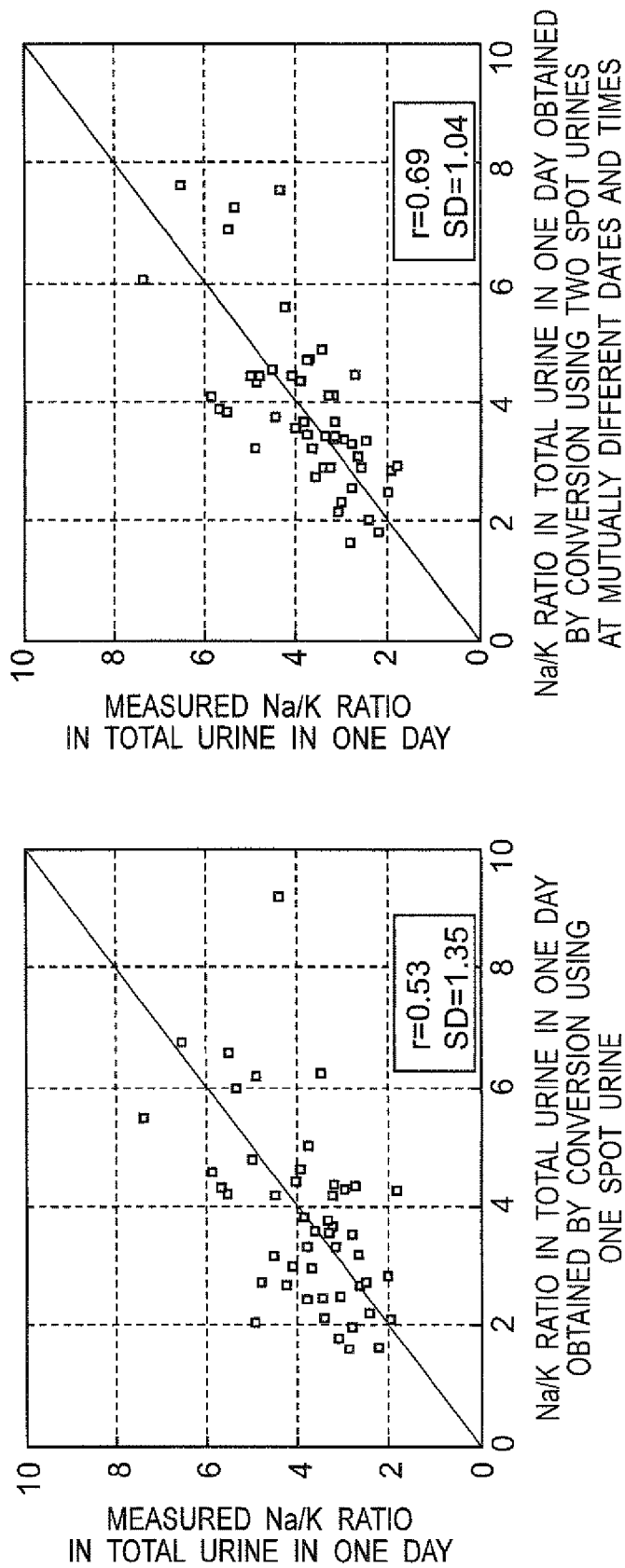

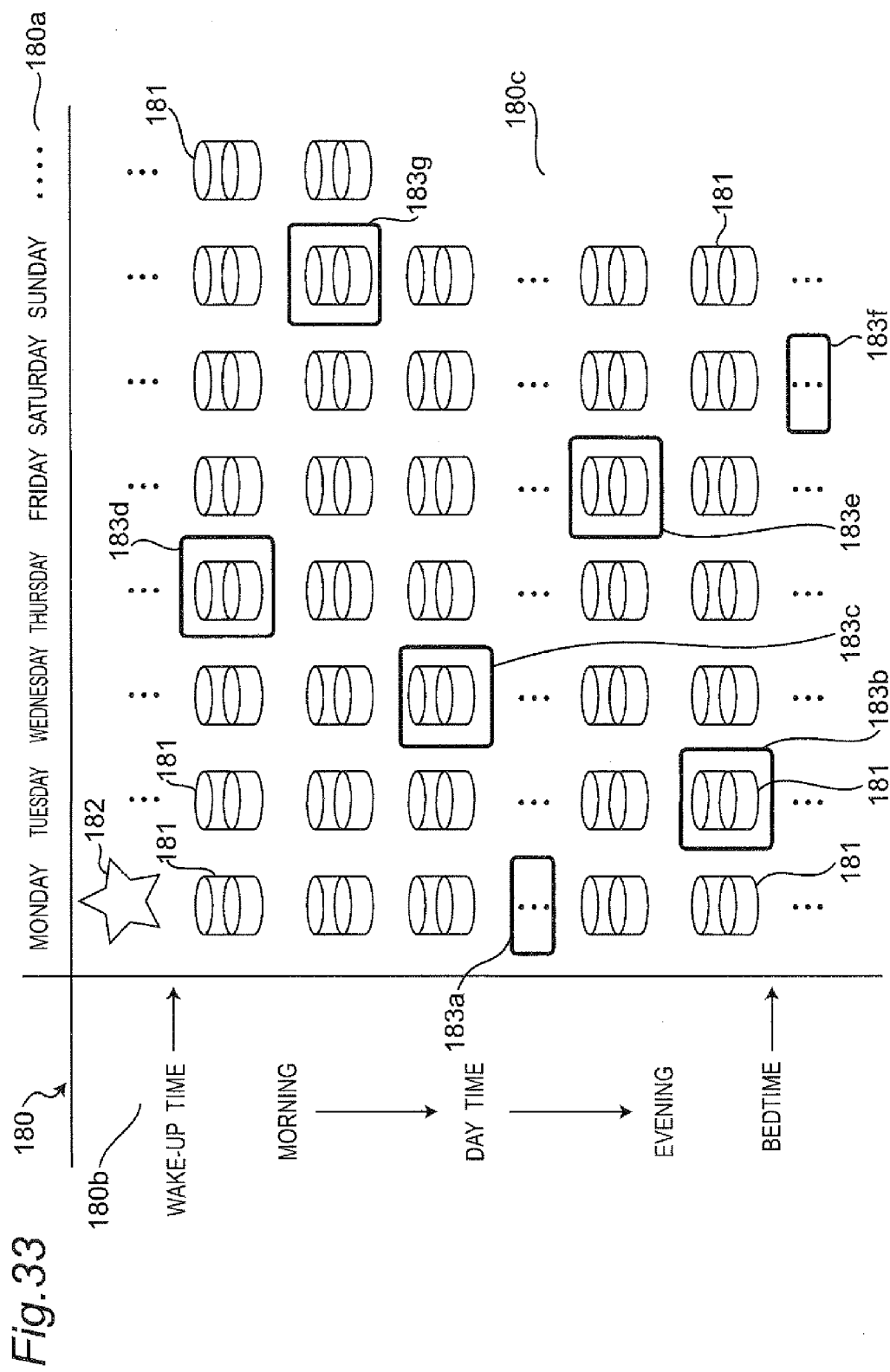

URINE COMPONENT ANALYSIS DEVICE

CROSS-REFERENCE TO RELATED APPLICATIONS

This is a continuation application of International Application No. PCT/JP2012/061397, with an International filing date of Apr. 27, 2012, which claims priority of Japanese Patent Application No. 2011-172060 filed on Aug. 5, 2011, the entire content of which is hereby incorporated by reference.

TECHNICAL FIELD

The present invention relates to a urine component analysis device and a urine component analysis method, and more particularly to a urine component analysis device and a urine component analysis method for determining a concentration ratio between two specific components in urine excreted by a subject.

BACKGROUND ART

As a technique for analyzing a urine component, method has been heretofore known in which a urine transport container including an inner tube and an outer tube is provided, and based on a weight or volume of urine collected in the inner tube, a total amount of urine collected first is determined and excretion amounts of components in the collected urine are measured as disclosed in, for example, Patent Document 1 (Japanese Patent Publication No. 3823039).

A method is known in which an amount of first urine after wake-up, which is excreted by a human, and a concentration of a specific component are measured to determine an excretion amount of the specific component in the first urine after wake-up and an elapsed time from urine discharge before sleep to first urine discharge after wake-up is acquired, the excretion amount of the specific component is converted into a defined time equivalent based on a ratio of the elapsed time to a preset defined time, and an excretion amount of the specific component excreted by the human in one day is calculated based on the converted defined time equivalent as disclosed in Patent Document 2 (Japanese Patent Publication No. 4329123).

SUMMARY OF THE INVENTION

As a dietary therapy for hypertensive patients, reduction of salt and intake of potassium are generally recommended. According to a reliable document ("Details of Diet Survey: Nutritional Epidemiology" written by Walter Willette, translated by Heizo Tanaka; 2nd edition; DAIICHI SYUPPAN CO., LTD; May 2003), sodium and potassium ingested by a human through diet are excreted into urine in ratios of 86% and 77%, respectively. Therefore, results of examining a sodium excretion amount (Na excretion amount) and a potassium excretion amount (K excretion amount), particularly a ratio between a sodium excretion amount and a potassium excretion amount (Na/K ratio), in every-day urine can be reflected in dietary therapies for hypertensive patients.

However, the method in Patent Document 1 (Japanese Patent Publication No. 3823039) has a problem that when measurement is performed over one day or plural days, a subject is required to collect a part of urine every time the subject discharges urine, thus causing a nuisance to the subject. For example, it is quite a nuisance and difficult to practice on a daily basis that a subject goes out with a container and collects urine at a place of visit.

Also, the method in Patent Document 2 (Japanese Patent Publication No. 4329123) has a problem that although only the first urine after wake-up is required, it is necessary to collect all the urine and measure an amount of urine, thus causing a nuisance to the subject. That is, when considering a case where the amount of one urine of a subject is relatively large, the subject is required to provide a relatively large-volume container of about 1 liter. Further, when the subject repeatedly uses the container, it takes time and labor to wash the relatively large-volume container. When a function to measure an amount of one urine is added to a toilet bowl, installation of a very large-scaled device is required.

Here, it may be not necessarily required to measure an amount of urine in order to know a ratio (Na/K ratio) between excretion amounts of sodium and potassium excreted by a subject in one day. This is because there is a correlation between a concentration of a specific component in one urine excreted by a human and a concentration of the specific component in total urine in one day when all the urine excreted by the human in the one day is gathered into one volume.

Thus, an object of the present invention is to provide a urine component analysis device and a urine component analysis method which are capable of easily and conveniently determining a concentration ratio between two specific components in total urine excreted by a subject in one day.

For achieving the object described above, a urine component analysis device of the present invention comprises:

a correlation storage section which stores data indicating a correlation between a concentration ratio between a first specific component and a second specific component in one urine excreted by a human and a concentration ratio between the first specific component and the second specific component in total urine in one day when all the urine excreted by the human in the one day is gathered into one volume;

a data input section which inputs data indicating a concentration ratio between the first specific component and the second specific component in one urine excreted by a subject; and a calculation section which determines a concentration ratio between the first specific component and the second specific component in total urine in one day when all the urine excreted by the subject in the one day is gathered into one volume, by performing conversion using the correlation stored in the correlation storage section, based on the concentration ratio between the first specific component and the second specific component in the one urine of the Subject obtained via the data input section.

In this specification, the "human" may be identical to the "subject". The "human" may include a plurality of persons, and may include the "subject" in this case.

The data input section may once input data indicating a concentration of each of the first specific component and the second specific component in one urine excreted by the subject, and the calculation section may determine a concentration ratio between the first specific component and the second specific component before performing the conversion.

In another aspect, the urine component analysis device of the present invention comprises:

a correlation storage section which stores data indicating a correlation between a concentration in one urine excreted by a human and a concentration in total urine in one day when all the urine excreted by the human in the one day is gathered into one volume for each of a first specific component and a second specific component in the urine excreted by the human;

a data input section which inputs data indicating a concentration of the first specific component and a concentration of the second specific component in one urine excreted by a subject; and a calculation section which determines each of a concentration of the first specific component and a concentration of the second specific component in total urine in one day when all the urine excreted by the subject in the one day is gathered into one volume, by performing conversion using the correlation stored in the correlation storage section, based on the concentration of the first specific component and the concentration of the second specific component in the one urine of the subject obtained via the data input section, and calculates, based on the results of conversion, a concentration ratio between the first specific component and the second specific component in the total urine of the subject in the one day.

In another aspect, the urine component analysis method of the present invention comprises:

storing in a predetermined storage section data indicating a correlation between a concentration ratio between a first specific component and a second specific component in one urine excreted by a human and a concentration ratio between the first specific component and the second specific component in total urine in one day when all the urine excreted by the human in the one day is gathered into one volume;

inputting data indicating a concentration ratio between the first specific component and the second specific component in one urine excreted by a subject; and determining a concentration ratio between the first specific component and the second specific component in total urine in one day when all the urine excreted by the subject in the one day is gathered into one volume, by performing conversion using the correlation stored in the storage section, based on the input concentration ratio between the first specific component and the second specific component in the one urine of the subject.

In another aspect, the urine component analysis method of the present invention comprises:

storing in a predetermined storage section data indicating a correlation between a concentration in one urine excreted by a human and a concentration in total urine in one day when all the urine excreted by the human in the one day is gathered into one volume for each of a first specific component and a second specific component in the urine excreted by the human;

inputting data indicating a concentration of the first specific component and a concentration of the second specific component in one urine excreted by a subject; and determining each of a concentration of the first specific component and a concentration of the second specific component in total urine in one day when all the urine excreted by the subject in the one day is gathered into one volume, by performing conversion using the correlation stored in the storage section, based on the input concentration of the first specific component and the input concentration of the second specific component in the one urine of the subject, and calculating, based on the results of calculation, a concentration ratio between the first specific component and the second specific component in the total urine of the subject in the one day.

According to a urine component analysis device and a urine component analysis method of the present invention, a concentration ratio between two specific components in total urine excreted by a subject in one day can be easily and conveniently determined.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 5A and 5B of FIG. 5 are views each showing a correlation between a measured Na concentration in one urine and a measured Na concentration in total urine in one day.

FIGS. 6A and 6B of FIG. 6 are views each showing a correlation between a measured K concentration in one urine and a measured K concentration in total urine in one day.

FIGS. 7A and 7B of FIG. 7 are views each showing a result of examining a Na/K ratio in total urine in one day, which is obtained by conversion using one urine, by using a measured Na/K ratio in total urine in one day.

FIGS. 8A and 8B of FIG. 8 are views showing, for subjects No. 2 and No. 6 respectively, a result of examining a daily Na/K ratio in total urine, which is obtained by conversion using one urine, by using a daily measured Na/K ratio in the total urine.

FIG. 9A of FIG. 9 are views each showing a correlation between an average Na concentration obtained using two urines (first and second urines after wake-up) and a measured Na concentration in total urine in one day. FIG. 9B of FIG. 9 is a view showing a correlation between an average K concentration obtained using two urines (first and second urines after wake-up) and a measured K concentration in total urine in one day.

FIG. 10A of FIG. 10 is a view showing a correlation between an average Na concentration obtained using two urines (urine just before sleep and first urine after wake-up) and a measured Na concentration in total urine in one day. FIG. 10B of FIG. 10 is a view showing a correlation between an average K concentration obtained using two urines (urine just before sleep and first urine after wake-up) and a measured K concentration in total urine in one day.

FIGS. 11A and 11B of FIG. 11 are views each showing a result of examining a Na/K ratio in total urine in one day, which is obtained by conversion using two urines, by using a measured Na/K ratio in total urine per day.

FIGS. 14A and 14B of FIG. 14 are views each showing a correlation (approximated by an exponential function)

between a measured Na/K ratio in one urine and a measured Na/K ratio in total urine in one day.

FIGS. 15A and 15B of FIG. 15 are views each showing a result of examining a Na/K ratio in total urine in one day, which is obtained by conversion using one urine, by using a measured Na/K ratio in total urine in one day.

FIGS. 16A and 16B of FIG. 16 are views showing, for subjects No. 2 and No. 6 respectively, a result of examining a Na/K ratio in daily total urine, which is obtained by conversion using one urine, by using a measured Na/K ratio in the daily total urine.

FIG. 17A of FIG. 17 is a view showing a correlation between an average Na/K ratio obtained using two urines (first and second urines after wake-up) and a measured Na/K ratio in total urine in one day. FIG. 17B of FIG. 17 is a view showing a correlation between an average Na/K ratio obtained using two urines (urine just before sleep and first urine after wake-up) and a measured Na/K ratio in total urine in one day.

FIG. 18A of FIG. 18 is a view showing a correlation between a measured Na/K ratio in first urine after wake-up and a measured Na/K ratio in total urine in one day. FIG. 18B of FIG. 18 is a view showing a correlation between an average Na/K ratio obtained using first urines after wake-up in two days and a measured Na/K ratio in total urine in two days.

FIG. 19A of FIG. 19 is a view showing a correlation between an average Na/K ratio obtained using first urines after wake-up in three days and a measured Na/K ratio in total urine in three days. FIG. 19B of FIG. 19 is a view showing a correlation between an average Na/K ratio obtained using first urines after wake-up in five days and a measured Na/K ratio in total urine in five days.

FIG. 20 is a view showing a correlation between an average Na/K ratio obtained using first urines after wake-up in seven days and a measured Na/K ratio in total urine in seven days.

FIG. 21 is a view showing one example of the contents of an advice table.

FIG. 22 is a view showing another example of the contents of an advice table.

Figure 23:
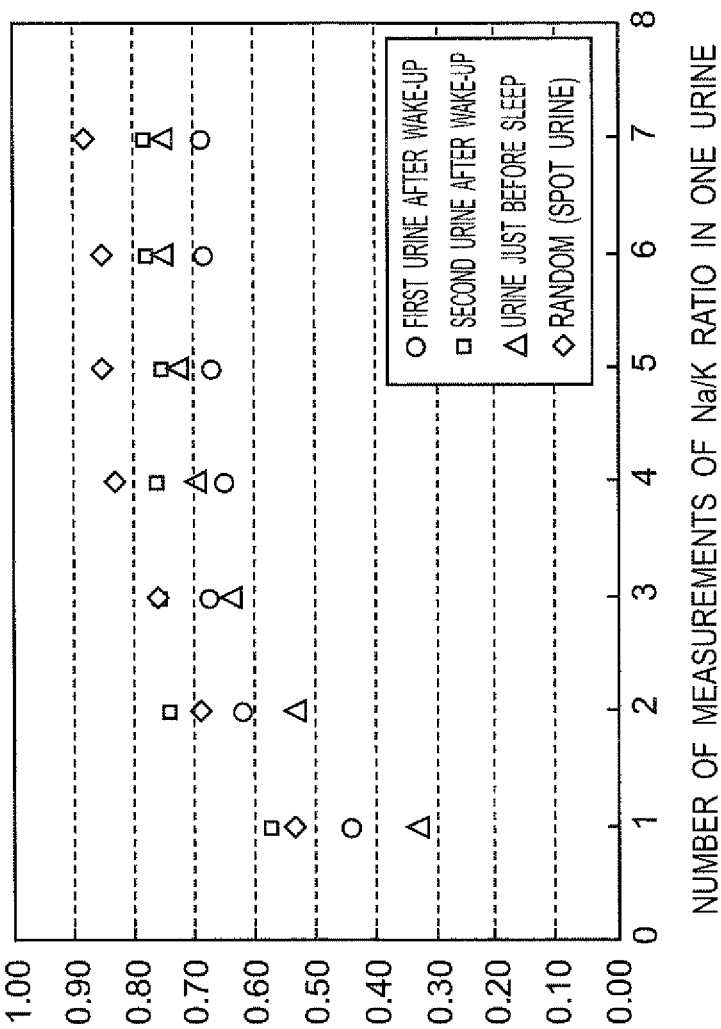

FIG. 23 is a view showing a correlation between a number of measurements and a correlation coefficient when a Na/K ratio in one urine at per day is measured up to 7 days.

FIGS. 24A and 24B are views showing a result of examining a Na/K ratio in total urine in one day, which is obtained by conversion using one spot urine and two spot urines, respectively, by using a measured Na/K ratio in total urine in one day.

Figure 25B:
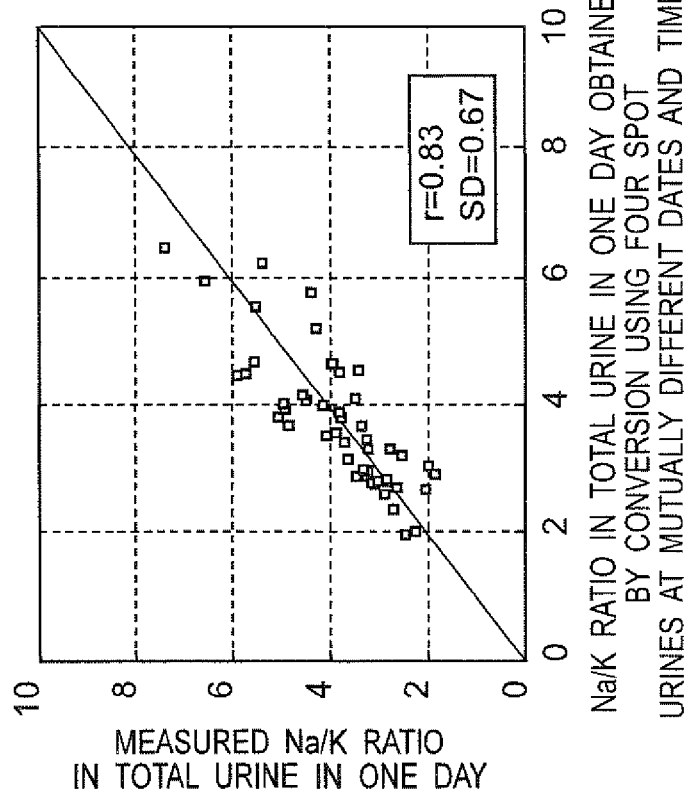
Figure 25A:
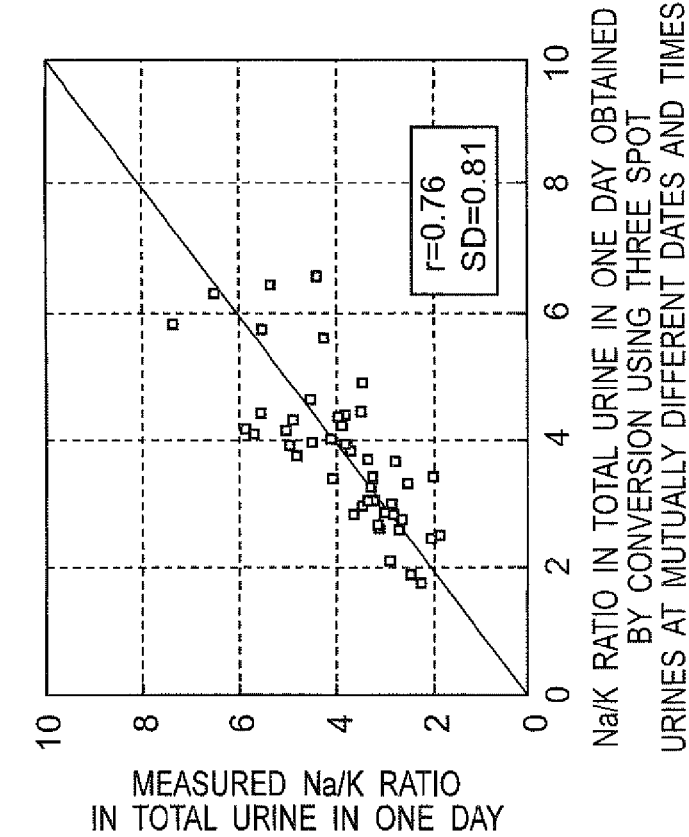

FIGS. 25A and 25B are views showing a result of examining a Na/K ratio in total urine in one day, which is obtained by conversion using three spot urines and four spot urines, respectively, by using a measured Na/K ratio in total urine in one day.

Figure 26:
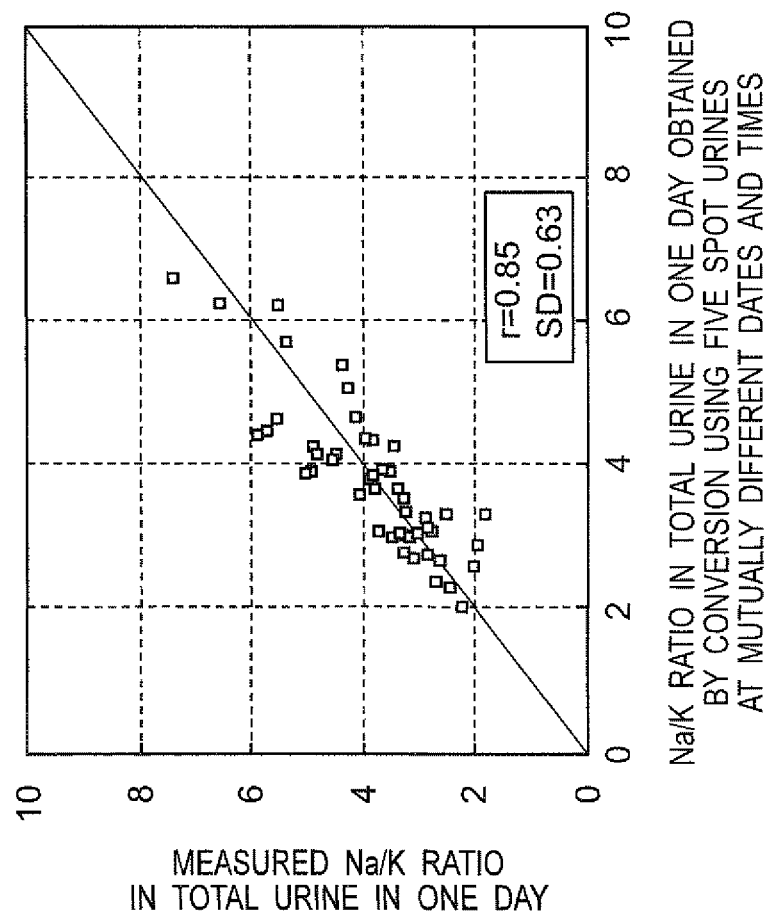

FIG. 26 is a view showing a result of examining a Na/K ratio in total urine in one day, which is obtained by conversion using five spot urines, by using a measured Na/K ratio in total urine in one day.

Figure 27A:
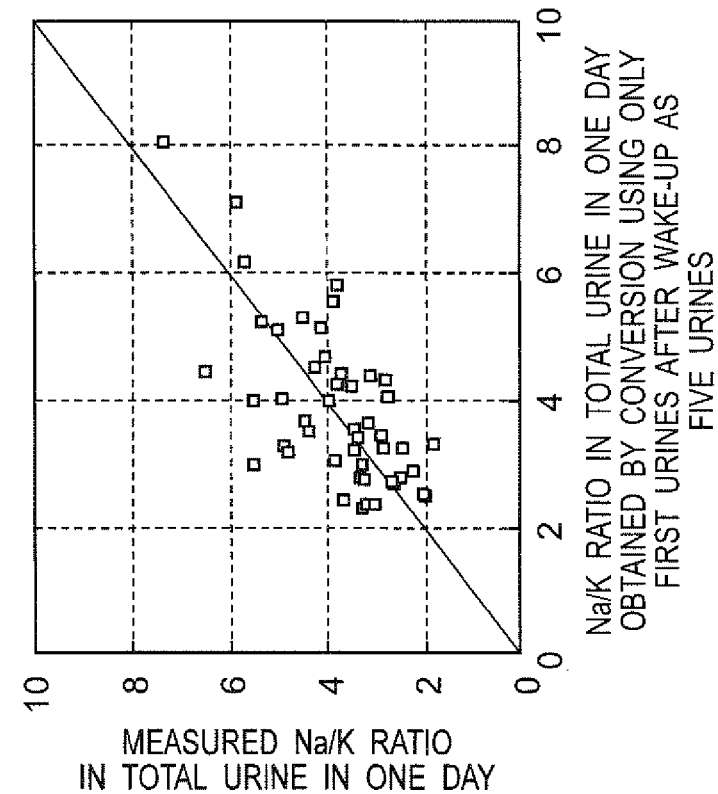
Figure 27B:
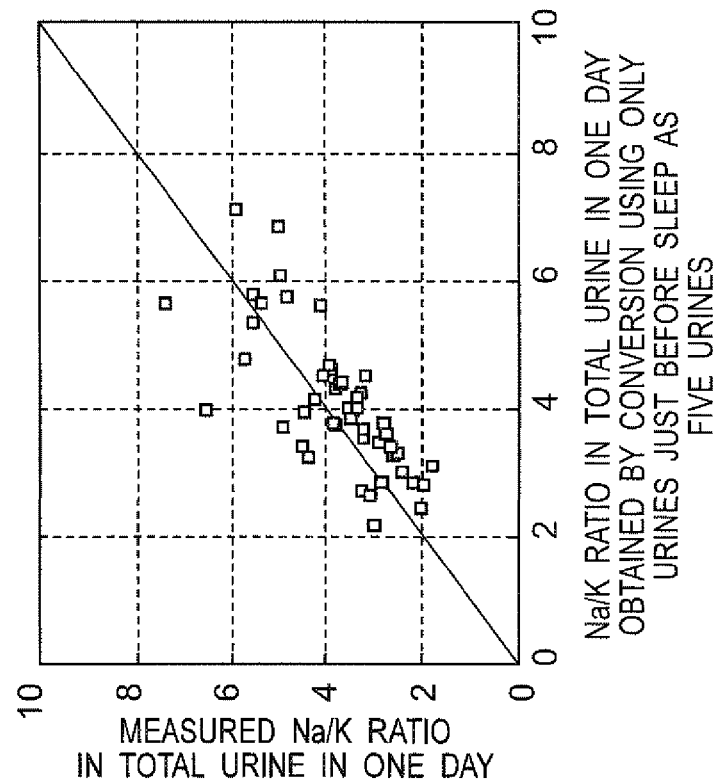

FIGS. 27A and 27B are views showing a result of matching a Na/K ratio in total urine in one day, which is obtained by conversion using only first urines after wake-up and urines just before sleep, respectively, in five days as five urines, with a measured Na/K ratio in total urine in one day.

Figure 28:
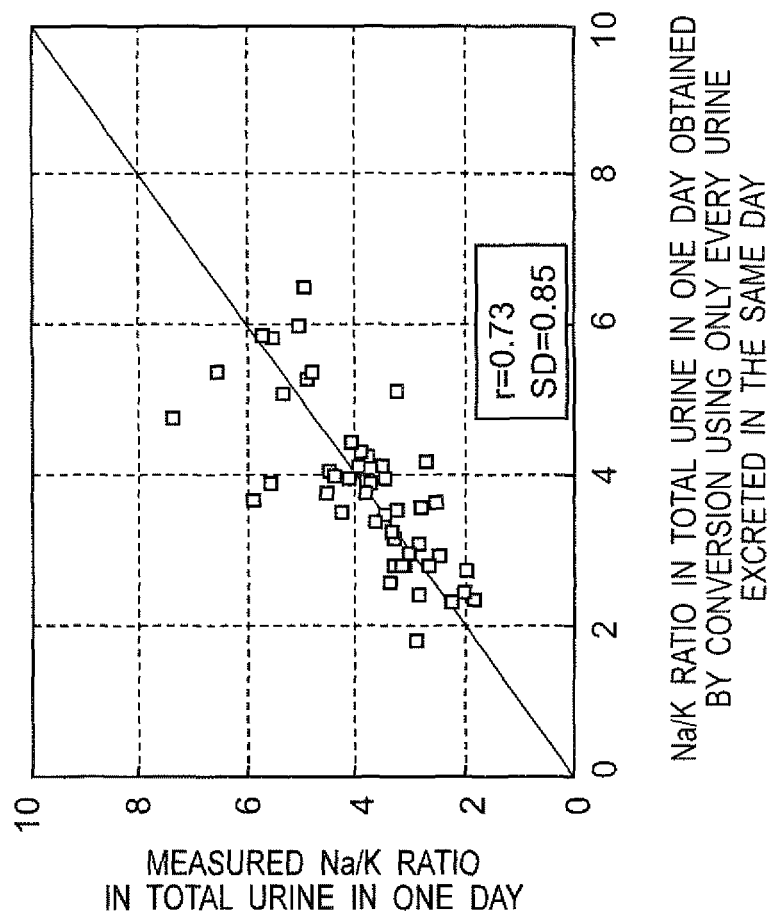

FIG. 28 is a view showing a result of matching a Na/K ratio in total urine in one day, which is obtained by conversion using only plural urines excreted in the same day, with a measured Na/K ratio in total urine in one day.

Figure 1:
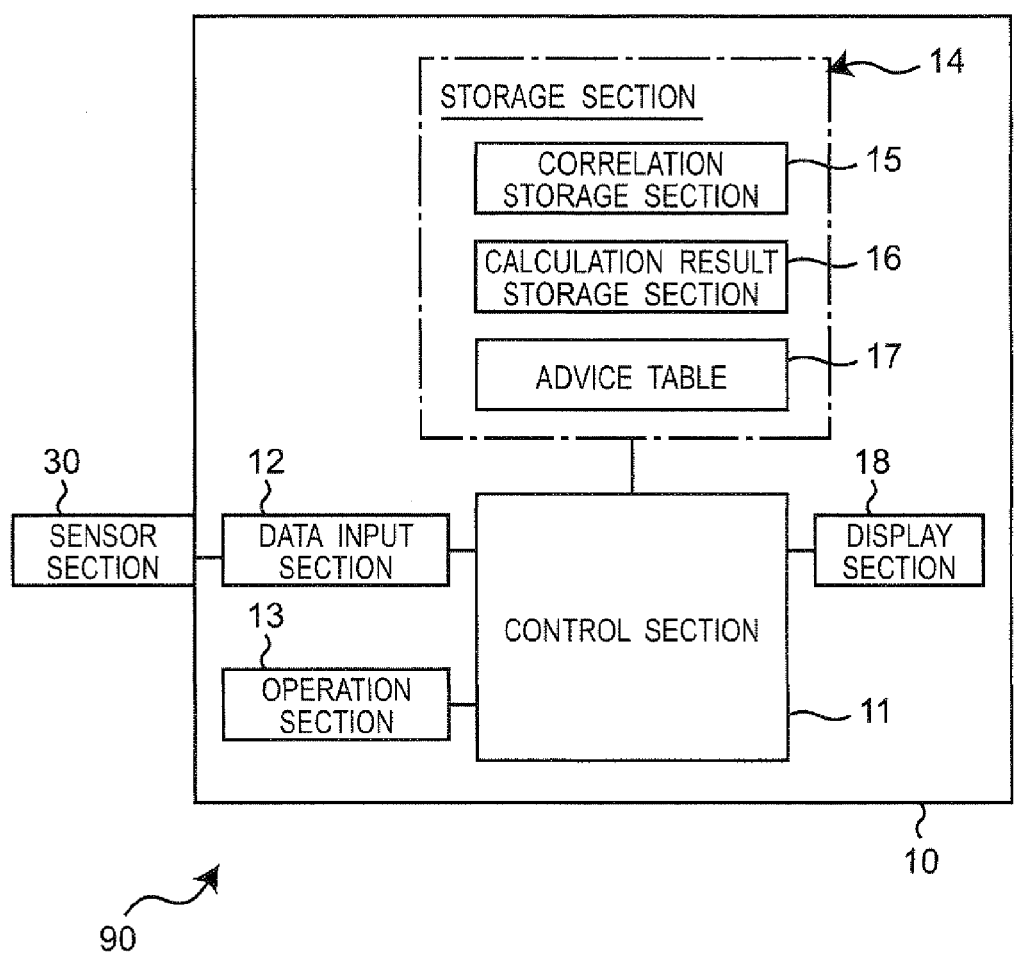
FIG. 1 is a view showing a block configuration of a urine component analysis device of one embodiment of the present invention.
Figure 29:
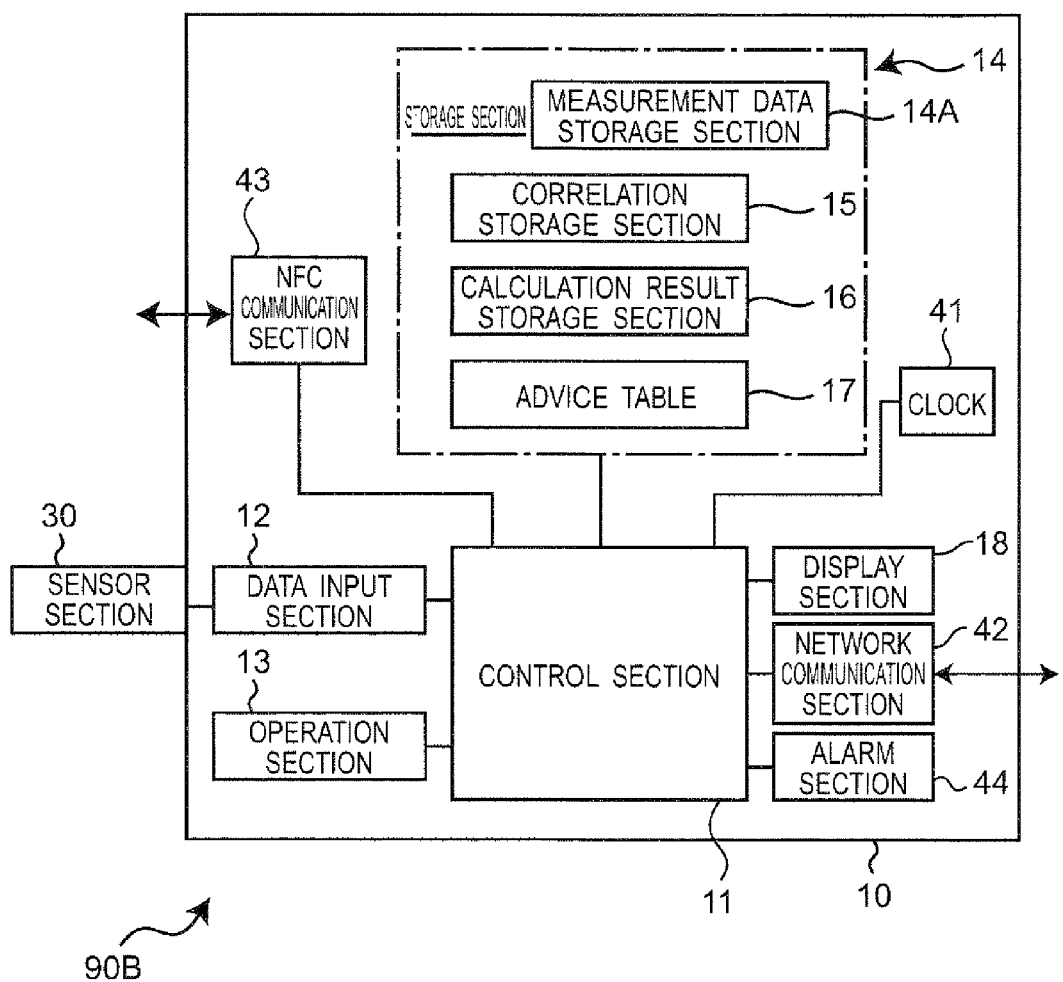

FIG. 29 is a view showing a block configuration of a urine component analysis device suitable for obtaining a result of conversion of a Na/K ratio using data of two or more urine measurements, the urine component analysis device being a modification of the urine component analysis device of FIG. 1.

Figure 30:
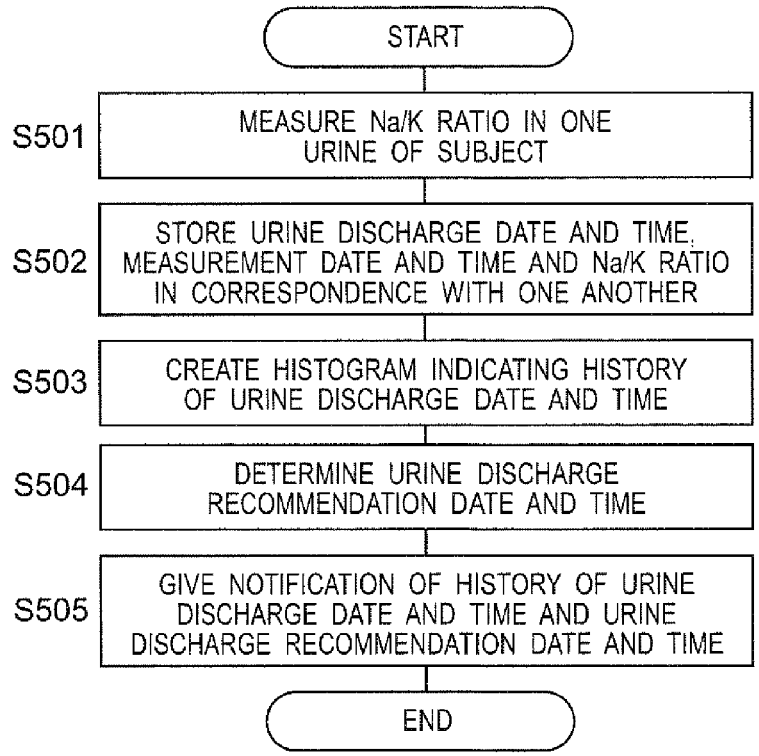

FIG. 30 is a view showing an operational flow about display of a urine discharge history and determination and notification of a urine discharge recommendation date and time by the urine component analysis device of FIG. 29.

Figure 31:
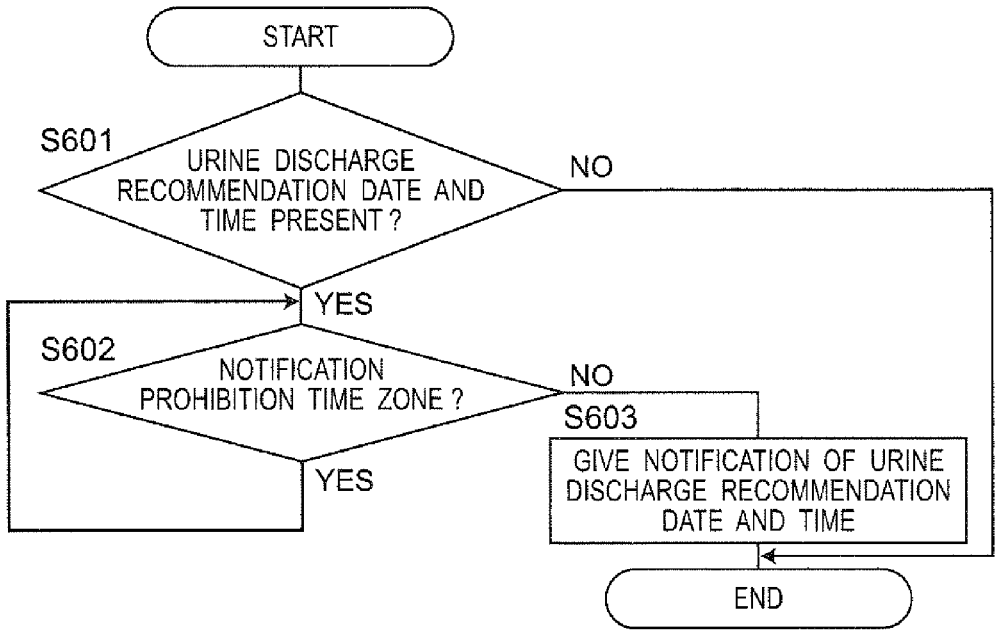

FIG. 31 is a view showing an operational flow about notification of a urine discharge recommendation date and time by the urine component analysis device of FIG. 29.

Figure 32A:
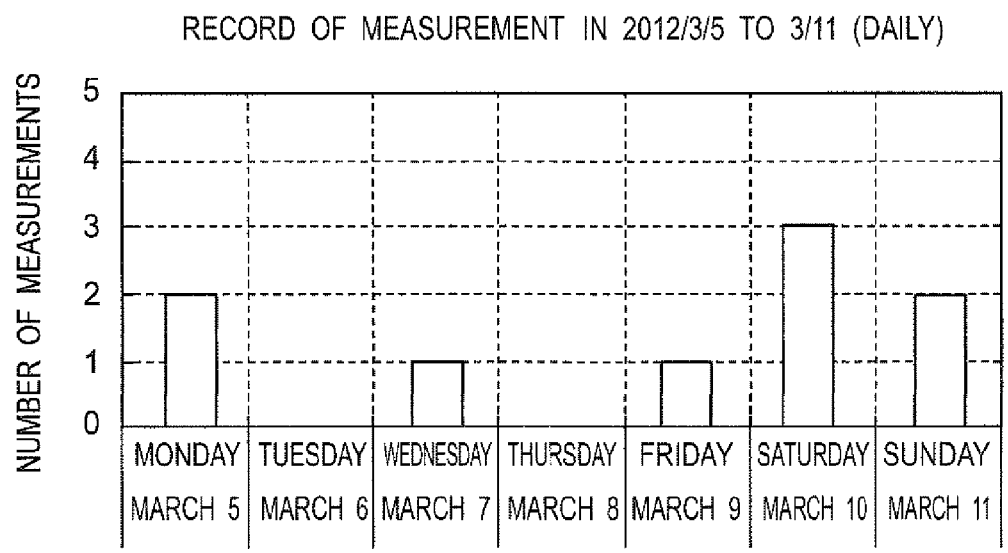
Figure 32B:
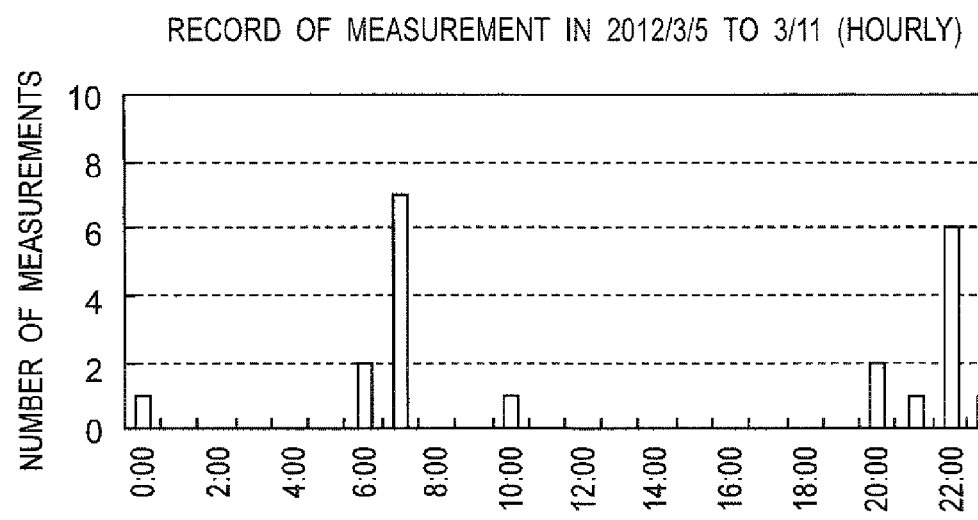

FIGS. 32A and 32B are views each showing an example of display to display a urine discharge history of a subject by a histogram.

FIG. 33 is a view schematically showing one example of how to determine a urine discharge recommendation date and time in the case where past measurement data is absent in the urine component analysis device of FIG. 29.

Figure 34:
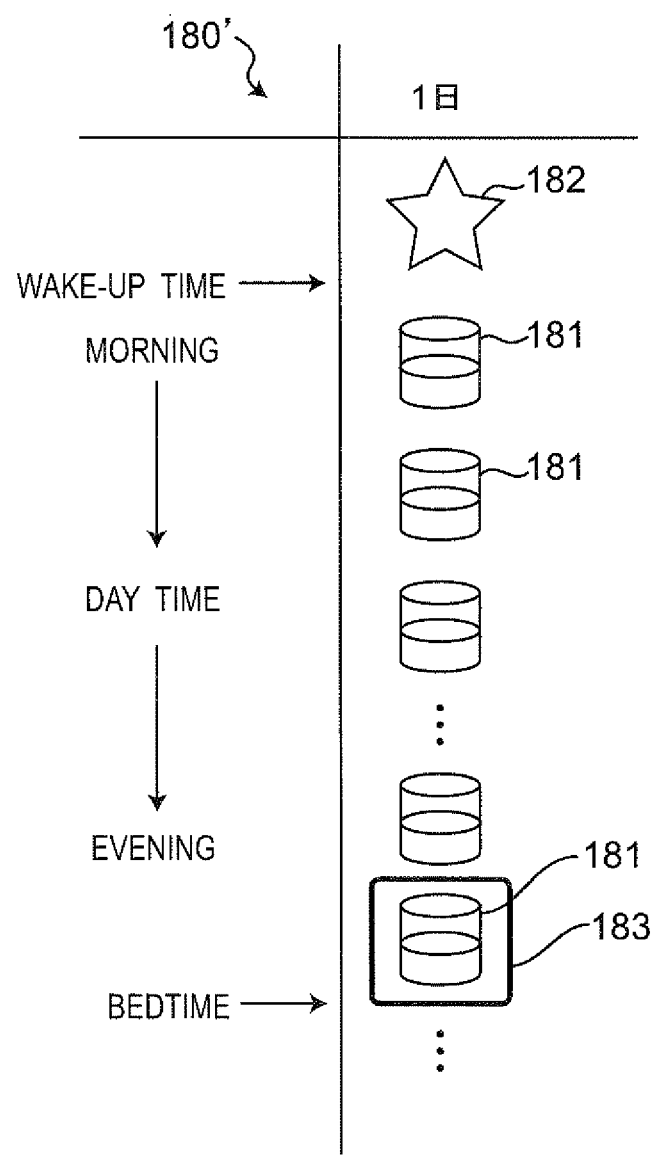

FIG. 34 is a view schematically showing another example of how to determine a urine discharge recommendation date and time in the case where past measurement data is absent in the urine component analysis device of FIG. 29.

Figure 35A:
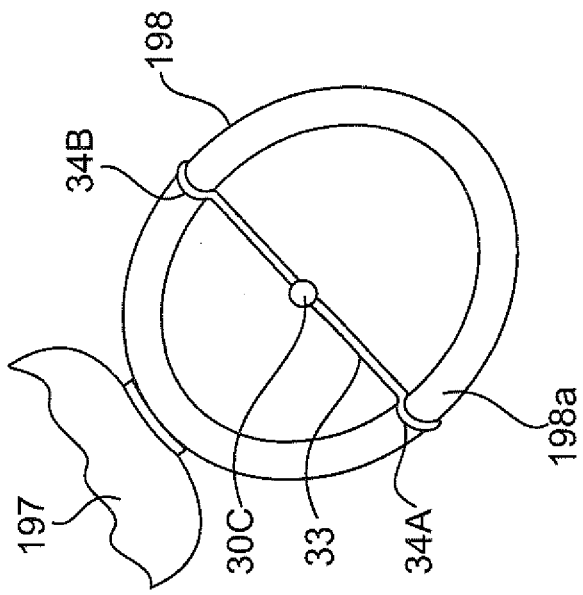
Figure 35B:
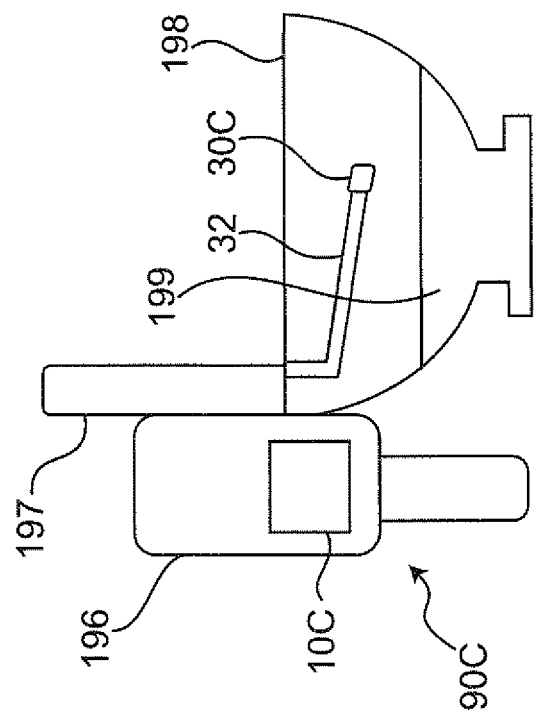

FIGS. 35A and 35B are views each showing an aspect of a urine component analysis device of another embodiment of the present invention.

Figure 36:
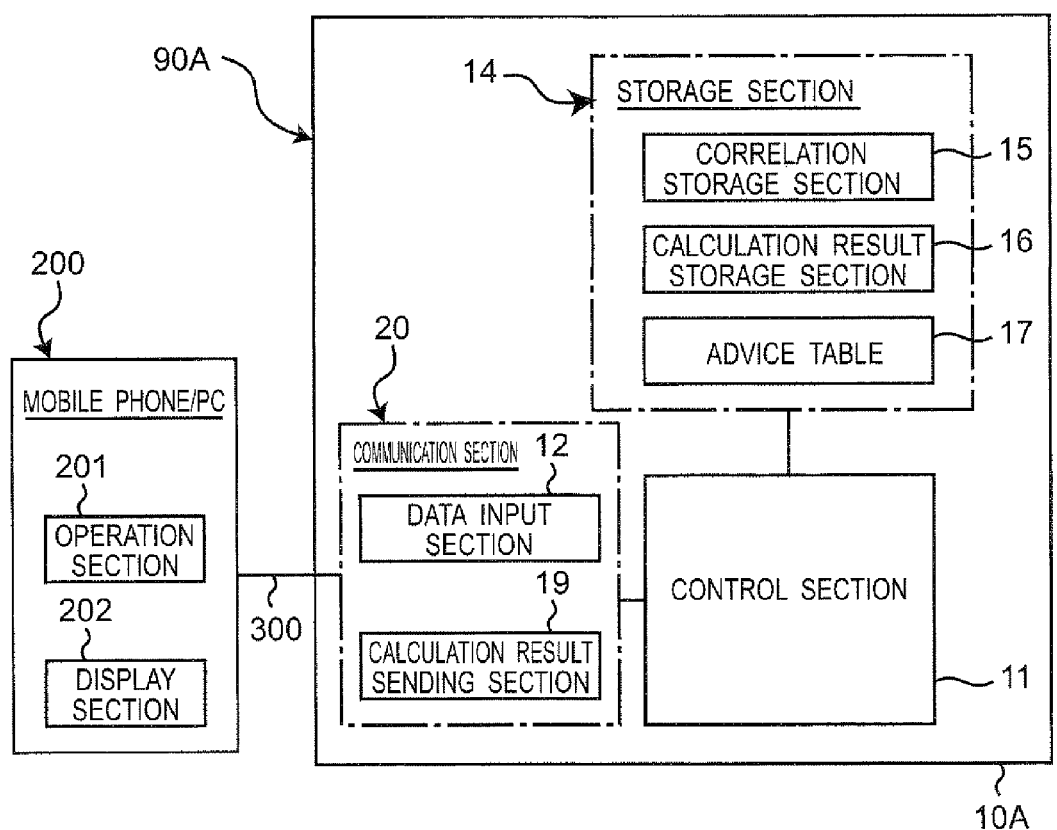

FIG. 36 is a view showing a block configuration of a urine component analysis device of another embodiment of the present invention.

DESCRIPTION OF EMBODIMENTS

Hereinafter, the present invention will be described in detail by way of illustrated embodiments.

First Embodiment

FIG. 1 shows a block configuration of a urine component analysis device (denoted by symbol 90 as a whole) of one embodiment of the present invention.

The urine component analysis device 90 includes a housing 10, a control section 11 mounted and stored in the housing 10, a data input section 12, an operation section 13, a storage section 14 and a display section 18. Further, the urine component analysis device 90 includes a sensor section 30 attached to the housing 10 so as to be projected to outside from the housing 10.

Figure 2A:
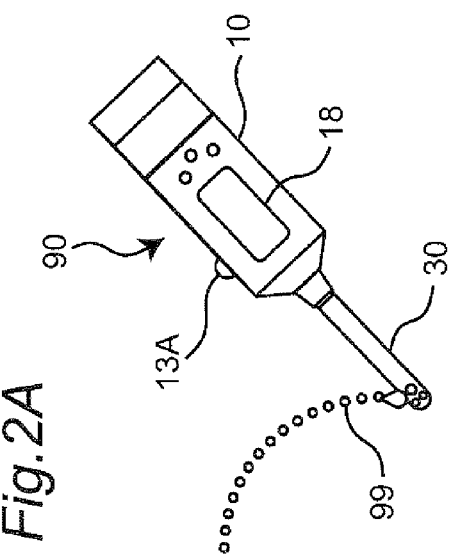
FIGS. 2A, 2B and 2C of are views each showing an aspect in which the urine component analysis device is used.

In this example, the housing 10 has a narrow and long prism-like external shape so that the housing is held by the user's hand as shown in FIG. 2A. The sensor section 30 is attached at one end of the housing 10 and has a narrow and long rod-like external shape. As a result, the urine component analysis device 90 is formed as a hand-held type urine component analysis device that is used by a user with the housing 10 held in the hand.

The sensor section 30 is one publicly known, and it comes into contact with urine 99 excreted by a subject to acquire data about concentrations of two components in the urine (first specific component and second specific component). In this example, the first specific component and the second specific component are sodium (Na) and potassium (K), respectively. In this example, the sensor section 30 may acquire data indicating a Na concentration and a K concentration in one urine 99, or may acquire a concentration ratio between Na and K (referred to as a "Na/K" ratio).

For example, when the hand-held type urine component analysis device 90 is used, urine is spritzed on the sensor section 30 as shown in FIG. 2A with the housing 10 held in the hand when the subject as a user discharges urine. In this way, the sensor section 30 can come into contact with urine excreted by the subject to acquire data about a Na concentration and a K concentration.

Figure 2B:
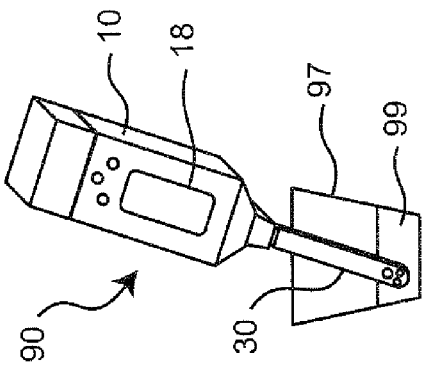

Alternatively, when the subject as a user discharges urine, the subject may collect a part of one urine 99 in a disposable paper cup 97, and immerse the sensor section 30 in the urine 99 in the paper cup 97 with the housing 10 held in the hand as shown in FIG. 2B.

Alternatively, when the subject as a user discharges urine, the subject may infiltrate a part of one urine into a sheet of toilet paper (not illustrated), and bring the sensor section 30 into contact with the urine infiltrated in the sheet of toilet paper with the housing 10 held in the hand.

Figure 2C:
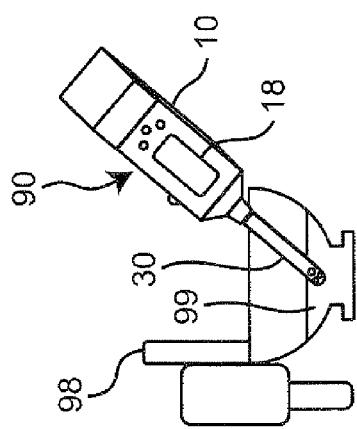

Alternatively, when the subject as a user discharges urine, the subject may store the urine 99 in a toilet bowl 98, and immerse the sensor section 30 in the urine stored in the toilet bowl with the housing 10 held in the hand as shown in FIG. 2C. Even if water exists in the toilet bowl 98 to dilute the urine 99, dilution of the urine 99 does not itself affect the obtained calculation result (concentration ratio).

In any case, according to the hand-held type urine component analysis device, a later-described calculation result is obtained by simple operations.

Figure 2D:
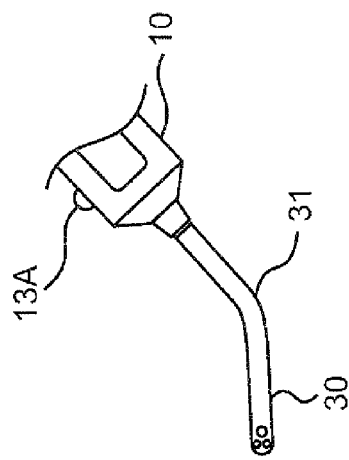
FIG. 2D is a view showing a preferred form of a hand-held type urine component analysis device.

The sensor section 30 is desired to have between itself and the housing 10 a flexible extension section 31 that is plastically deformed to be bent when a force is applied thereto by the subject as a user as shown in FIG. 2D. When the extension section 31 is kept bent, the subject as a user can spritz urine on the sensor section 30 in a comfortable position during urine discharge.

The control section 11 shown in FIG. 1 includes a CPU (central processing unit) operated by software, and acts as a calculation section etc. to execute various kinds of processing.

The data input section 12 inputs, in real time in this example, data about concentrations of two components in the urine (first specific component and second specific component) acquired by the sensor section 30.

The operation section 13 includes a scroll button 13A shown in FIG. 2A, and acts to input various kinds of information from the user. Examples of information to be input include urine specification information indicating whether urine to be measured is the first urine after wake-up or the second urine after wake-up or the urine just before sleep, and information indicating a blood pressure and a BMI (body mass index) of the subject. When urine specification information is input, the operation section 13 acts as a urine specification section.

The storage section 14 includes an EEPROM (an electrically rewritable nonvolatile memory) in this example, and includes a correlation storage section 15, a calculation result storage section 16 and an advice table 17.

As shown in, for example, FIGS. 5A and 5B, the correlation storage section 15 stores data indicating a correlation between a measured Na concentration in one urine and a measured Na concentration in total urine in one day (dots in the figure each represent measured data). Specifically, FIG. 5A shows a case where a relationship between a measured Na concentration in the first urine after wake-up (abscissa x, unit: [mmol/L]) and a measured Na concentration in total urine in one day (ordinate y, unit: [mmol/L]) is approximated by a straight line (shown by a solid line in FIG. 5A), and an expression of the straight line is stored as data indicating a correlation. In this case, it is shown that there is a high correlation with the correlation coefficient being r=0.77. FIG. 5B shows a case where a relationship between a measured Na concentration in the second urine after wake-up (abscissa x, unit: [mmol/L]) and a measured Na concentration in total urine in one day (ordinate y, unit: [mmol/L]) is similarly approximated by a straight line (shown by a solid line in FIG. 5B), and an expression of the straight line is stored as data indicating a correlation. In this case, it is shown that the correlation coefficient is r=0.80.

As shown in FIGS. 6A and 6B, the correlation storage section 15 stores a correlation between a measured K concentration in one urine and a measured K concentration in total urine in one day (dots in the figure each represent measured data). Specifically, FIG. 6A shows a case where a relationship between a measured K concentration in the first urine after wake-up (abscissa x, unit: [mmol/L]) and a measured K concentration in total urine in one day (ordinate y, unit: [mmol/L]) is approximated by a straight line (shown by a solid line in FIG. 6A), and an expression of the straight line is stored as data indicating a correlation. In this case, it is shown that the correlation coefficient is r=0.55. FIG. 6B shows a case where a relationship between a measured K concentration in the second urine after wake-up (abscissa x, unit: [mmol/L]) and a measured K concentration in total urine in one day (ordinate y, unit: [mmol/L]) is similarly approximated by a straight line (shown by a solid line in FIG. 6B), and an expression of the straight line is stored as data indicating a correlation. In this case, it is shown that the correlation coefficient is r=0.73.

A case where an expression approximated by a straight line is stored as data indicating a correlation has been described as an example, but the present invention is not limited to this example. The correlation storage section 15 may store other functions, conversion databases and the like.

The measured Na concentration, K concentration and later-described Na/K ratio in total urine of a subject are measured after all the urine excreted by the subject is gathered into one volume (stored-urine method; the same hereinafter).

The advice table 17 stores a Na/K ratio in correspondence with advices appropriate to the Na/K ratio for the subject, as shown in, for example, FIG. 21. For example, the advice of "Ideal value" corresponds to a Na/K ratio falling within a range of 0.0 to 1.0. The advice of "Goal achieved" corresponds to a Na/K ratio falling within a range of 1.0 to 2.0. The advice of "Goal will be achieved with a little effort" corresponds to a Na/K ratio falling within a range of 2.0 to 2.5. The advice of "Value high and take care of your dietary life" corresponds to a Na/K ratio falling within a range of 2.5 to 3.0. The advice of "Value so high. Take enough care of your dietary life" corresponds to a Na/K ratio of 3.0 or more. The value range segmentation of the Na/K ratio in the advice table 17 is one example, and it is also possible to make a setting with the value range segmentation changed.

The calculation result storage section 16 shown in FIG. 1 sequentially stores calculation results (later-described Na/K ratio in total urine of a subject in one day) from the control section 11 in correspondence with measurement dates and times, respectively. For example, the user can easily know a tendency of daily change in Na/K ratio in total urine of the subject in one day by reading the contents of the calculation result storage section.

The display section 18 includes an LCD (liquid crystal display device) (see FIG. 2A) in this example, and displays various kinds of information such as a calculation result from the control section 11.

Figure 3:
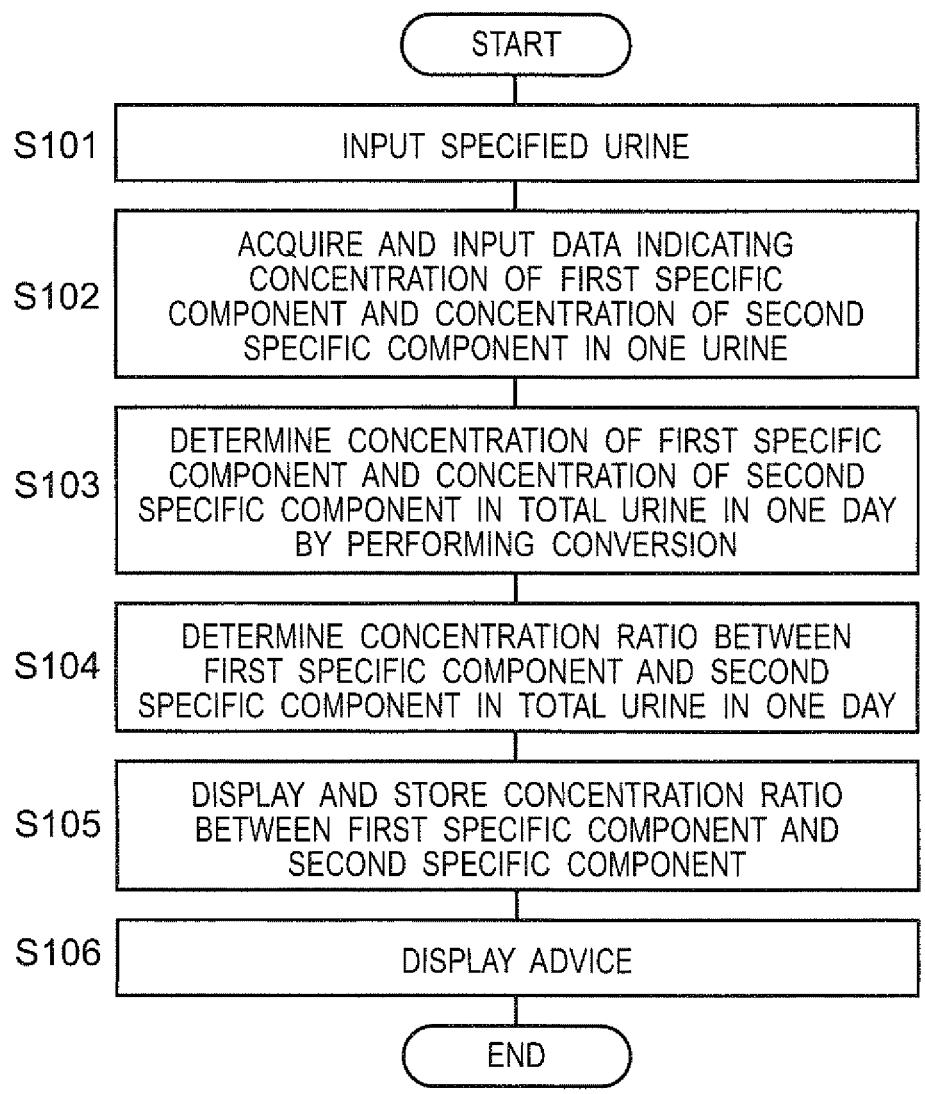
FIG. 3 is a view showing one example of an operational flow of the urine component analysis device.

The urine component analysis device 90 is operated under control by the control section 11 generally in accordance with a flow shown in, for example, FIG. 3.

i) First, for example when a user turns on a power switch (not illustrated), a urine specification mode is started as shown in Step S101 in FIG. 3.

In this example, the control section 11 acts as a urine specification section to display options of "first urine after wake-up", "second urine after wake-up" and "urine just before sleep" etc. on the display section 18 in the urine specification mode. When the user rotates a scroll button 13A as these options are displayed, options of "first urine after wake-up", "second urine after wake-up" and "urine just before sleep" etc. are sequentially highlighted as a selection candidate. For example, when the user depresses the scroll button 13A while "first urine after wake-up" is highlighted, "first urine after wake-up" is input as the urine to be measured. In a manner described above, the user inputs, via the operation section 13, urine specification information indicating whether urine to be measured is the first urine after wake-up or the second urine after wake-up or the urine just before sleep. When input of urine specification information is completed, a urine measurement mode is started.

If urine to be measured is always limited to, for example, "first urine after wake-up", the urine specification mode (Step S101) can be skipped.

ii) Next, in the urine measurement mode, the user spritzes the urine 99 on the sensor section 30 as shown in, for example, FIG. 2A, and depresses the scroll button 13A. Then, as shown in Step S102 in FIG. 3, the sensor section 30 acquires data indicating a Na concentration and a K concentration in one urine 99, and the data input section 12 inputs in real time each of the data indicating a Na concentration and a K concentration in this example.

When this data input is completed, a calculation mode is started.

iii) Next, in the calculation mode, as shown in Step S103 in FIG. 3, the control section 11 acts as a calculation section to determine a Na concentration and a K concentration in total urine in one day when all the urine excreted by the subject in the one day is gathered into one volume, by performing conversion using a correlation (the correlation shown in FIG. 5A and FIG. 6A in this example) stored in the correlation storage section 15, based on the Na concentration and the K concentration in one urine 99 of the subject which are obtained via the data input section 12.

When the object to be converted is one associated with "second urine after wake-up", the correlation shown in FIG. 5B and FIG. 6B is accordingly used.

iv) Further, as shown in Step S104 in FIG. 3, the control section 11 acts as a calculation section to calculate, based on those results of conversion, a Na/K ratio in total urine in one day when all the urine excreted by the subject in the one day is gathered into one volume.

v) Then, as shown in Step S105, the Na/K ratio obtained by conversion is stored in the calculation result storage section 16 in correspondence with a measurement date and time. At the same time, the control section 11 acts as a calculation result notification section to display on the display section 18 the Na/K ratio obtained by conversion.

vi) As shown in Step S106, the control section 11 acts as an advice section to select an advice appropriate to the Na/K ratio obtained by conversion, by referring to the advice table 17 (FIG. 21), and display on the display section 18 the advice along with the Na/K ratio obtained by conversion.

For example, if the Na/K ratio is 0.5, the numerical value and the advice of "Ideal value" are displayed.

In this case, a Na concentration and a K concentration in total urine in one day are each determined by performing conversion based on a Na concentration and a K concentration in one urine excreted by the subject, and therefore it is not necessary to actually measure an amount of urine excreted by the subject. When a Na concentration and a K concentration in at least one urine excreted by the subject are obtained as input data, a result of conversion is obtained. Therefore, according to the urine component analysis device 90, a Na/K ratio in total urine excreted by the subject in one day can be easily and conveniently determined.

FIGS. 7A and 7B each show a result of examining a Na/K ratio in total urine in one day, which is obtained by conversion using one urine as described above, by using a measured Na/K ratio in total urine in one day (including results for two or more subjects). Specifically, FIG. 7A shows a result of determining a correlation coefficient by matching a Na/K ratio in total urine in one day (abscissa), which is obtained by conversion using the first urine after wake-up, with a measured Na/K ratio in total urine in one day (ordinate). The correlation coefficient at this time was r=0.65. FIG. 7B shows a result of determining a correlation coefficient by matching a Na/K ratio in total urine in one day (abscissa), which is obtained by conversion using the second urine after wake-up, with a measured Na/K ratio in total urine in one day (ordinate). The correlation coefficient at this time was r=0.84.

FIG. 8A shows, for subject No. 2, a result of examining a daily Na/K ratio in total urine (data connected by a dashed line in the figure), which is obtained by conversion using one urine (first urine after wake-up), by using a measured daily Na/K ratio in total urine (data connected by a solid line in the figure). FIG. 8B shows, for subject No. 6, a result of examining a daily Na/K ratio in total urine (data connected by a dashed line in the figure), which is obtained by conversion using one urine (first urine after wake-up), by using a measured daily Na/K ratio in total urine (data connected by a solid line in the figure).

In the results of examination in FIGS. 7A and 7B and FIGS. 8A and 8B, a high correlation (correlation coefficient) is obtained between converted value and the measured value. Thus, it has become apparent that a Na/K ratio in total urine excreted by the subject in one day can be accurately determined.

For example, when the user continuously depresses the scroll button 13A for 3 or more seconds subsequent to turning on the power switch, the control section 11 may display on the display section 18 an option of which information of "urine specification", "blood pressure" and "BMI" etc. is to be input. When the user rotates the scroll button 13A as these options are displayed, options of "urine specification", "blood pressure" and "BMI" etc. are sequentially highlighted as a selection candidate. For example, when the user depresses the scroll button 13A while "blood pressure" is highlighted, a mode of input of "blood pressure" is started. In the mode of input of "blood pressure", values indicating input candidates of blood pressure (maximum blood pressure or minimum blood pressure) are displayed on the display section 18 in the ascending or descending manner when the user rotates the scroll button 13A. When the user depresses the scroll button 13A, a value displayed at this time is input as a blood pressure (maximum blood pressure or minimum blood pressure) of the subject. BMI can be inputted in the same manner as in the case of the blood pressure.

In this case, when not only the advice appropriate to the Na/K ratio but also advices appropriate to the blood pressure and BMI are stored in the advice table 17 as shown in FIG. 22, a more appropriate advice can be given to the subject. In the example in FIG. 22, advices are stored while being classified in correspondence with a maximum blood pressure/minimum blood pressure of "less than 135/85 mmHg" and a BMI of "less than 25", a maximum blood pressure/minimum blood pressure of "135/85 mmHg or more" and a BMI of "25 or more" and a maximum blood pressure/minimum blood pressure of "135/85 mmHg or more" and a BMI of "less than 25" for each of Na/K ratio ranges of "0.0 to 1.0", "1.0 to 2.0", "2.0 to 2.5", "2.5 to 3.0" and "3.0 or more".

For example, the advice of "Goal achieved for Na/K ratio. You need weight reduction/exercise and medication" is stored for the Na/K ratio range of "1.0 to 2.0" and the maximum blood pressure/minimum blood pressure" of "135/85 mmHg or more" and the BMI of "25 or more".

The advice of "Na/K ratio so high. Take enough care of your dietary life. You need weight reduction/exercise and medication" is stored for the Na/K ratio range of "3.0 or more" and the maximum blood pressure/minimum blood pressure" of "135/85 mmHg or more" and the BMI of "25 or more".

When such an advice table is provided, a precise and more appropriate advice can be given to the subject.

Second Embodiment

In the first embodiment described above, a Na concentration and a K concentration in total urine in one day are each determined by performing conversion based on a Na concentration and a K concentration in one urine excreted by a subject, but the present invention is not limited thereto. A Na concentration and a K concentration in total urine in one day may be each determined by performing conversion based on a Na concentration and a K concentration in plural urines (two urines in this example) excreted by the subject over one day or plural days.

In this case, as shown in, for example, FIG. 9A, data indicating a correlation between an average Na concentration obtained using two urines (first and second urines after wake-up) and a measured Na concentration in total urine in one day is stored in the correlation storage section 15. At the same time, as shown in FIG. 9B, data indicating a correlation between an average K concentration obtained using two urines (first and second urines after wake-up) and a measured K concentration in total urine in one day is stored.

Specifically, FIG. 9A shows a case where a relationship between an average Na concentration obtained by averaging a measured Na concentration in the first urine after wake-up and a measured Na concentration in the second urine after wake-up (abscissa x, unit: [mmol/L]) and a measured Na concentration in total urine in one day (ordinate y, unit: [mmol/L]) is approximated by a straight line (shown by a solid line in FIG. 9A), and an expression of the straight line is stored as data indicating a correlation. In this case, it is shown that there is a high correlation with the correlation coefficient being r=0.82. FIG. 9B shows a case where a relationship between an average K concentration obtained by averaging a measured K concentration in the first urine after wake-up and a measured K concentration in the second urine after wake-up (abscissa x, unit: [mmol/L]) and a measured K concentration in total urine in one day (ordinate y, unit: [mmol/L]) is similarly approximated by a straight line (shown by a solid line in FIG. 9B), and an expression of the straight line is stored as data indicating a correlation. In this case, it is shown that the correlation coefficient is r=0.78.

Alternatively, in place of the correlation in FIGS. 9A and 9B or in addition to the correlation in FIGS. 9A and 9B, data indicating a correlation between an average Na concentration obtained using two urines (urine just before sleep and first urine after wake-up) and a measured Na concentration in total urine in one day is stored as shown in, for example, FIG. 10A. At the same time, as shown in FIG. 10B, data indicating a correlation between an average K concentration obtained using two urines (urine just before sleep and first urine after wake-up) and a measured K concentration in total urine in one day is stored.

Specifically, FIG. 10A shows a case where a relationship between an average Na concentration obtained by averaging a measured Na concentration in the urine just before sleep and a measured Na concentration in the first urine after wake-up (abscissa x, unit: [mmol/L]) and a measured Na concentration in total urine in one day (ordinate y, unit: [mmol/L]) is approximated by a straight line (shown by a solid line in FIG. 10A), and an expression of the straight line is stored as data indicating a correlation. In this case, it is shown that the correlation coefficient is r=0.83. FIG. 10B shows a case where a relationship between an average K concentration obtained by averaging a measured K concentration in the urine just before sleep and a measured K concentration in the first urine after wake-up (abscissa x, unit: [mmol/L]) and a measured K concentration in total urine in one day (ordinate y, unit: [mmol/L]) is similarly approximated by a straight line (shown by a solid line in FIG. 10B), and an expression of the straight line is stored as data indicating a correlation. In this case, it is shown that the correlation coefficient is r=0.75.

Figure 4:
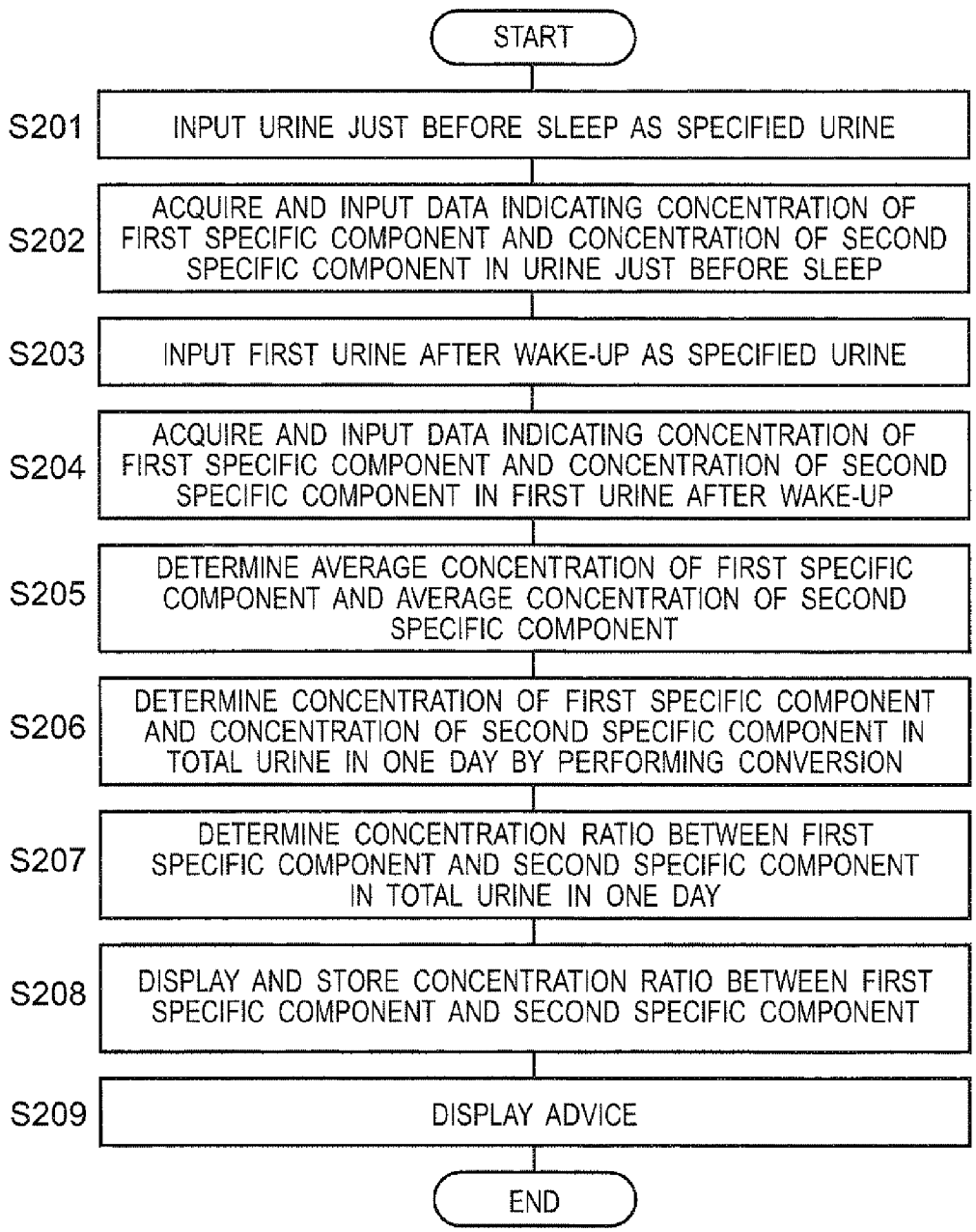
FIG. 4 is a view showing another example of an operational flow of the urine component analysis device.

In this case, a urine component analysis device 90 is operated under control by a control section 11 generally in accordance with a flow shown in, for example, FIG. 4.

i) First, for example when a user turns on a power switch (not illustrated), a first urine specification mode is started as shown in Step S201 in FIG. 4.

In this example, in the first urine specification mode, the user inputs, via an operation section 13, urine specification information indicating that urine to be measured is the urine just before sleep. When input of urine specification information is completed, a first urine measurement mode is started.

ii) In the first urine measurement mode, the user spritzes urine 99 on a sensor section 30 as shown in, for example, FIG. 2A, and depresses a scroll button 13A. Then, as shown in Step S202 in FIG. 4, the sensor section 30 acquires data indicating a Na concentration and a K concentration in one urine 99, and a data input section 12 inputs in real time each of the data indicating a Na concentration and a K concentration in this example.

In this example, a calculation mode is not started here, and the user turns off a power switch (not illustrated). The already input Na/K ratio is stored in a storage section 14.

iii) Next, when the user turns on a power switch (not illustrated), a second urine specification mode is started as shown in Step S203 in FIG. 4.

In this example, in the second urine specification mode, the user inputs, via the operation section 13, urine specification information indicating that urine to be measured is the first urine after wake-up. When input of urine specification information is completed, a second urine measurement mode is started.

iv) In the second urine measurement mode, the user spritzes the urine 99 on a sensor section 30 again as shown in, for example, FIG. 2A, and depresses a scroll button 13A. Then, as shown in Step S204 in FIG. 4, the sensor section 30 acquires data indicating a Na concentration and a K concentration in one urine 99, and a data input section 12 inputs in real time each of the data indicating a Na concentration and a K concentration in this example.

When this second data input is completed, a calculation mode is started.

v) In the calculation mode, as shown in Step S205 in FIG. 4, the control section 11 acts as a calculation section to determine an average concentration by averaging the concentration in two urines excreted by the subject (urine just before sleep and first urine after wake-up in this example) for each of Na and K. That is, an average Na concentration is obtained by averaging a measured Na concentration in the urine just before sleep and a measured Na concentration in the first urine after wake-up. At the same time, an average K concentration is obtained by averaging a measured K concentration in the urine just before sleep and a measured K concentration in the first urine after wake-up. The average Na concentration and average K concentration are an object to be converted.

vi) Next, as shown in Step S206 in FIG. 4, the control section 11 acts as a calculation section to determine a Na concentration and a K concentration in total urine in one day when all the urine excreted by the subject in the one day is gathered into one volume, by performing conversion using a correlation (the correlation shown in FIGS. 10A and 10B in this example) stored in a correlation storage section 15, based on the obtained average Na concentration and average K concentration.

When the object to be converted is one associated with "first urine after wake-up" and "second urine after wake-up", the correlation shown in FIG. 9A and FIG. 9B is accordingly used.

vii) Further, as shown in Step S207 in FIG. 4, the control section 11 acts as a calculation section to calculate, based on those results of conversion, a Na/K ratio in total urine in one day when all the urine excreted by the subject in the one day is gathered into one volume.

viii) Then, as shown in Step S208, the Na/K ratio obtained by conversion is stored in a calculation result storage section 16 in correspondence with a measurement date and time. At the same time, the control section 11 acts as a calculation result notification section to display on the display section 18 the Na/K ratio obtained by conversion.

ix) As shown in Step S209, the control section 11 acts as an advice section to select an advice appropriate to the Na/K ratio obtained by conversion, by referring to an advice table 17 (FIG. 21 or FIG. 22), and display on the display section 18 the advice along with the Na/K ratio obtained by conversion.

FIGS. 11A and 11B each show a result of examining a Na/K ratio in total urine in one day, which is obtained by conversion using two urines as described above, by using a measured Na/K ratio in total urine per day (including results for two or more subjects). Specifically, FIG. 11A shows a result of determining a correlation coefficient by matching a Na/K ratio in total urine in one day (abscissa), which is obtained by conversion using the first and second urines after wake-up, with a measured Na/K ratio in total urine in one day (ordinate). The correlation coefficient at this time was r=0.77. FIG. 11B shows a result of determining a correlation coefficient by matching a Na/K ratio in total urine in one, day (abscissa), which is obtained by conversion using the urine just before sleep and the first urine after wake-up, with a measured Na/K ratio in total urine in one day (ordinate). The correlation coefficient at this time was r=0.74.

In the results of examination in FIGS. 11A and 11B, a high correlation (correlation coefficient) is obtained between converted value and the measured value. Thus, it has become apparent that a Na/K ratio in total urine excreted by the subject in one day can be accurately determined.

When a Na concentration and a K concentration in one urine or an average Na concentration and an average K concentration in two urines are used as an object to be converted, it is desirable that which is to be used should be determined in consideration of accuracy of conversion and ease of performing urine measurement by the subject. As for the order of accuracy, generally, a combination of "first urine after wake-up" and "second urine after wake-up" is ranked first, a combination of "urine just before sleep" and "first urine after wake-up" is ranked second, "second urine after wake-up" is ranked third, and "first urine after wake-up" is ranked fourth (one ranked first and one ranked second are comparable in accuracy). When the subject goes to work immediately after measuring a Na concentration and a K concentration in the first urine after wake-up at home, it is difficult in practice to measure a Na concentration and a K concentration in the "second urine after wake-up" at the workplace. Therefore, in this case, it is desirable to use a combination of "urine just before sleep" and "first urine after wake-up".

The "measured Na concentration in total urine in one day" and "measured K concentration in total urine in one day", which serve as a basis of the correlation stored in the correlation storage section 15, can be each determined as a concentration in total urine in one day or plural days when all the urine excreted by a human over the one day or the plural days is gathered into one volume. In this case, the determined concentration is not affected by an amount of urine and a number of urine discharges in each day. The "measured Na concentration in total urine in one day" and "measured K concentration in total urine in one day", which serve as a basis of the correlation, may be each determined by determining an average value of the concentration per day for urine excreted by a human and averaging the average value per day over plural days. In this case, urine may be gathered every day to determine an average value of the concentration per day without the necessity to gather all the urine excreted by a human over plural days into one volume. Accordingly, the correlation can be easily acquired.

Third Embodiment

In the first and second embodiments described above, a Na concentration and a K concentration in total urine in one day are each determined by performing conversion based on a Na concentration and a K concentration in the urine excreted by a subject, and a Na/K ratio is determined therefrom, but the present invention is not limited thereto. A control section 11 as a calculation section may use, as an object to be converted, a Na/K ratio in the urine excreted by the subject.

In this case, as shown in, for example, FIGS. 14A and 14B, data indicating a correlation between a Na/K ratio in one urine excreted by a human and a Na/K ratio in total urine in one day when all the urine excreted by a human in the one day is gathered into one volume is stored in a correlation storage section 15.

Specifically, FIG. 14A shows a case where a relationship between a measured Na/K ratio in the first urine after wake-up (abscissa x) and a measured Na/K ratio in total urine in one day (ordinate y) is approximated by an exponential function (shown by a solid line in FIG. 14A), and an expression of the exponential function is stored as data indicating a correlation. In this case, it is shown that the correlation coefficient is r=0.60. FIG. 14B shows a case where a relationship between a measured Na/K ratio in the second urine after wake-up (abscissa x) and a measured Na/K ratio in total urine in one day (ordinate y) is similarly approximated by an exponential function (shown by a solid line in FIG. 14B), and an expression of the exponential function is stored as data indicating a correlation. In this case, it is shown that the correlation coefficient is r=0.88.

A sensor section 30 directly acquires a Na/K ratio in one urine or plural urines excreted by the subject, and a data input section 12 inputs in real time data indicating the Na/K ratio.

Figure 12:
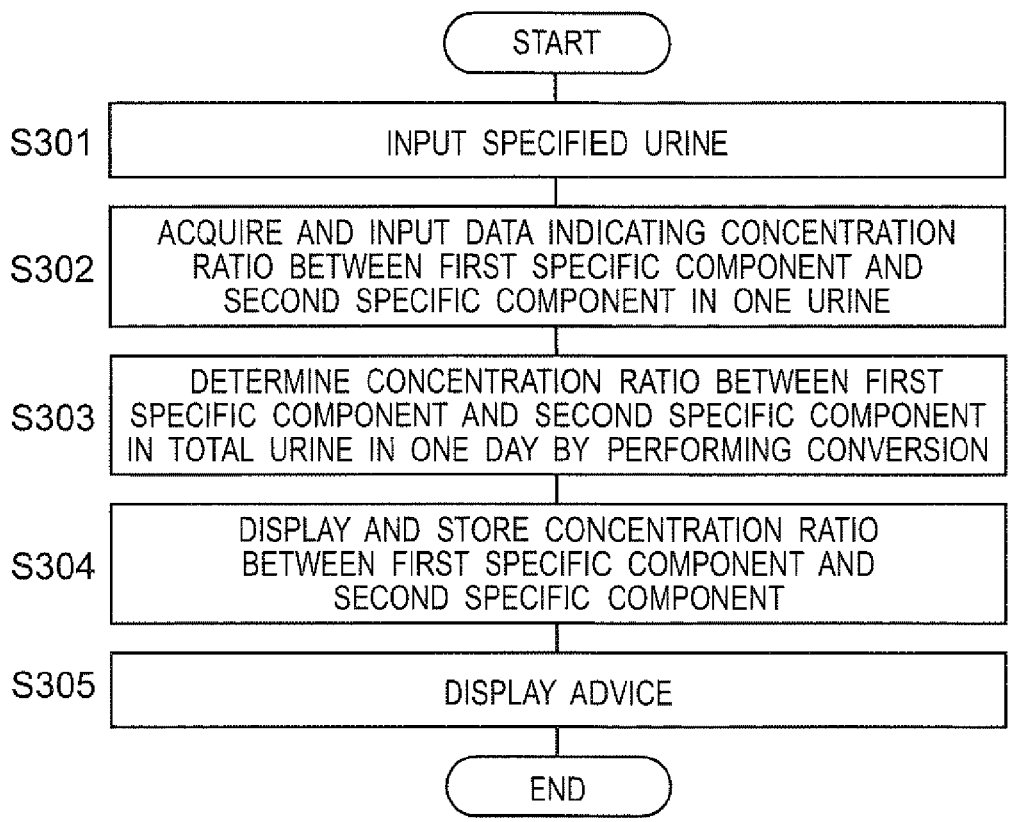
FIG. 12 is a view showing still another example of an operational flow of the urine component analysis device.

The urine component analysis device 90 is operated under control by the control section 11 generally in accordance with a flow shown in, for example, FIG. 12.

i) First, for example when a user turns on a power switch (not illustrated), a urine specification mode is started as shown in Step S301 in FIG. 12.

In this example, in the urine specification mode, the user inputs, via the operation section 13, urine specification information indicating that urine to be measured is the first urine after wake-up. When input of urine specification information is completed, a urine measurement mode is started.

If urine to be measured is always limited to, for example, "first urine after wake-up", the urine specification mode (Step S301) can be skipped.

ii) Next, in the urine measurement mode, the user spritzes the urine 99 on the sensor section 30 as shown in, for example, FIG. 2A, and depresses the scroll button 13A. Then, as shown in Step S302 in FIG. 12, the sensor section 30 acquires data indicating a Na/K ratio in one urine 99, and the data input section 12 inputs in real time the data indicating a Na/K ratio in this example.

When this data input is completed, a calculation mode is started.

iii) Next, in the calculation mode, as shown in Step S303 in FIG. 12, the control section 11 acts as a calculation section to determine a Na/K ratio in total urine in one day when all the urine excreted by the subject in the one day is gathered into one volume, by performing conversion using a correlation (the correlation shown in FIG. 14A) stored in the correlation storage section 15, based on the Na/K ratio in one urine 99 of the subject which is obtained via the data input section 12.

When the object to be converted is one associated with "second urine after wake-up", the correlation shown in FIG. 14B is accordingly used.

iv) Then, as shown in Step S304 in FIG. 12, the Na/K ratio obtained by conversion is stored in a calculation result storage section 16 in correspondence with a measurement date and time. At the same time, the control section 11 acts as a calculation result notification section to display on the display section 18 the Na/K ratio obtained by conversion.

v) As shown in Step S305, the control section 11 acts as an advice section to select an advice appropriate to the Na/K ratio obtained by conversion, by referring to an advice table 17 (FIG. 21 or FIG. 22), and display on the display section 18 the advice along with the Na/K ratio obtained by conversion.

In this case, a Na/K ratio in total urine in one day is determined by performing conversion based on a Na/K ratio in one urine excreted by the subject, and therefore it is not necessary to actually measure an amount of urine excreted by the subject. When a Na/K ratio in at least one urine excreted by the subject are obtained as input data, a result of conversion is obtained. Therefore, according to the urine component analysis device 90, a Na/K ratio in total urine excreted by the subject in one day can be easily and conveniently determined.

FIGS. 15A and 15B each show a result of examining a Na/K ratio in total urine in one day, which is obtained by conversion using one urine as described above, by using a measured Na/K ratio in total urine in one day (including results for two or more subjects). Specifically, FIG. 15A shows a result of determining a correlation coefficient by matching a Na/K ratio in total urine in one day (abscissa), which is obtained by conversion using the first urine after wake-up, with a measured Na/K ratio in total urine in one day (ordinate). The correlation coefficient at this time was r=0.60. FIG. 15B shows a result of determining a correlation coefficient by matching a Na/K ratio in total urine in one day (abscissa), which is obtained by conversion using the second urine after wake-up, with a measured Na/K ratio in total urine in one day (ordinate). The correlation coefficient at this time was r=0.88.

FIG. 16A shows, for subject No. 2, a result of examining a daily Na/K ratio in total urine (data connected by a dashed line in the figure), which is obtained by conversion using one urine (first urine after wake-up), by using a measured daily Na/K ratio in total urine (data connected by a solid line in the figure). FIG. 16B shows, for subject No. 6, a result of examining a daily Na/K ratio in total urine (data connected by a dashed line in the figure), which is obtained by conversion using one urine (first urine after wake-up), by using a measured daily Na/K ratio in total urine (data connected by a solid line in the figure).

In the results of examination in FIGS. 15A and 15B and FIGS. 16A and 15B, a high correlation (correlation coefficient) is obtained between converted value and the measured value. Thus, it has become apparent that a Na/K ratio in total urine excreted by the subject in one day can be accurately determined.

In this embodiment, the correlation stored in the correlation storage section 15 is approximated by an exponential function, but the present invention is not limited thereto, and the correlation may be approximated by a straight line. Even when the correlation is approximated by a straight line, a Na/K ratio in total urine excreted by the subject in one day can be easily and conveniently determined.

Fourth Embodiment

In the third embodiment described above, a Na/K ratio in total urine in one day is determined by performing conversion based on a N/K ratio in one urine excreted by a subject, but the present invention is not limited thereto. A Na/K ratio in total urine in one day may be determined by performing conversion based on a Na/K ratio in plural urines (two urines in this example) excreted by the subject over one day or plural days.

In this case, as shown in, for example, FIG. 17A, data indicating a correlation between an average Na/K ratio obtained using two urines (first and second urines after wake-up) and a measured Na/K ratio in total urine in one day is stored in the correlation storage section 15. Specifically, FIG. 17A shows a case where a relationship between an average Na/K ratio obtained by averaging a measured Na/K ratio in the first urine after wake-up and a measured Na/K ratio in the second urine after wake-up (abscissa x) and a measured Na/K ratio in total urine in one day (ordinate y) is approximated by a straight line (shown by a solid line in FIG. 17A), and an expression of the straight line is stored as data indicating a correlation. In this case, it is shown that there is a high correlation with the correlation coefficient being r=0.76.

Alternatively, in place of the correlation in FIG. 17A or in addition to the correlation in FIG. 17A, data indicating a correlation between an average Na/K ratio obtained using two urines (urine just before sleep and first urine after wake-up) and a measured Na/K ratio in total urine in one day is stored as shown in, for example, FIG. 17B. Specifically, FIG. 17B shows a case where a relationship between an average Na/K ratio obtained by averaging a measured Na/K ratio in the urine just before sleep and a measured Na/K ratio in the first urine after wake-up (abscissa x) and a measured Na/K ratio in total urine in one day (ordinate y) is similarly approximated by a straight line (shown by a solid line in FIG. 17B), and an expression of the straight line is stored as data indicating a correlation. In this case, it is shown that the correlation coefficient is r=0.76.

Figure 13:
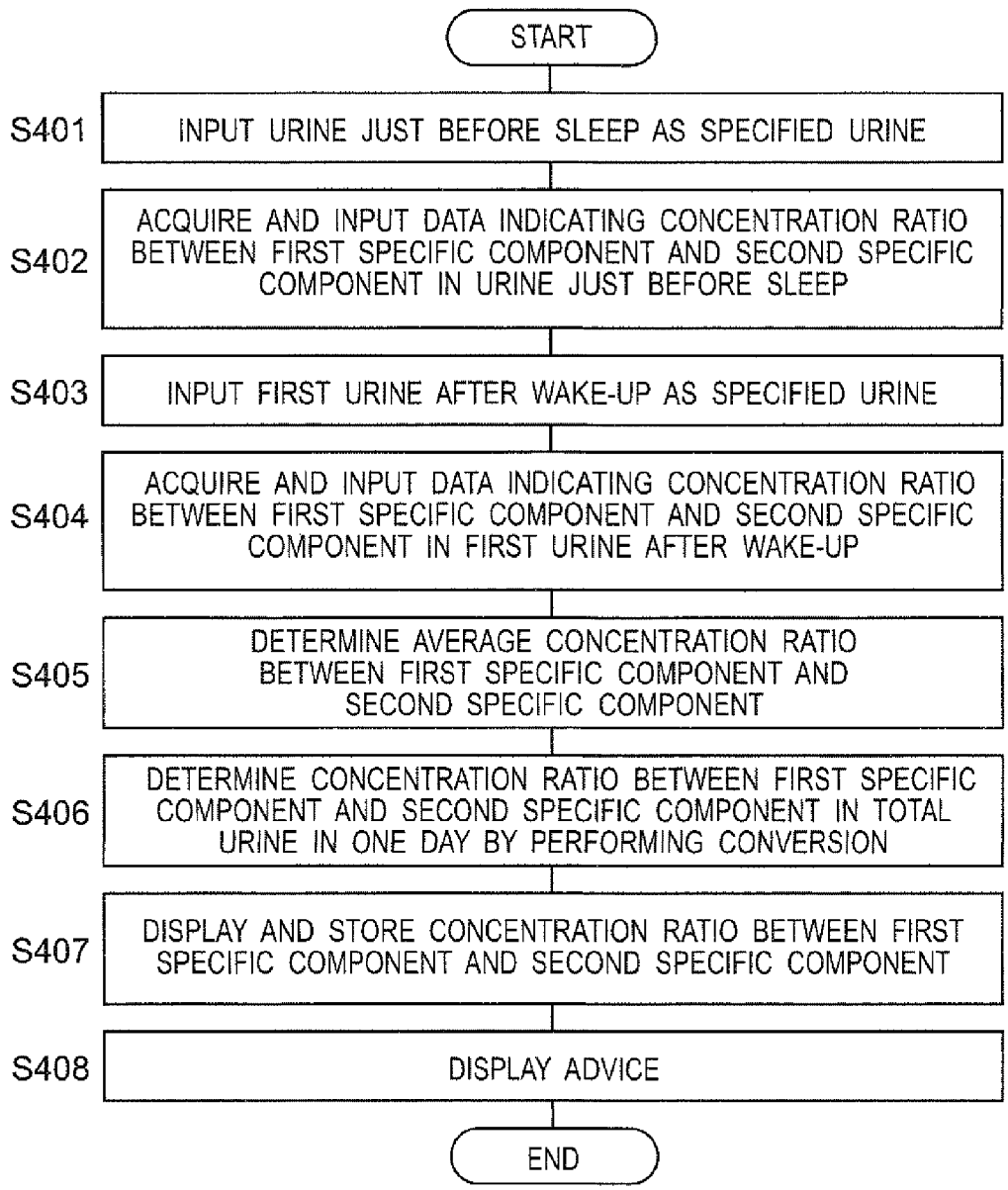
FIG. 13 is a view showing still another example of an operational flow of the urine component analysis device.

In this case, a urine component analysis device 90 is operated under control by a control section 11 generally in accordance with a flow shown in, for example, FIG. 13.

i) First, for example when a user turns on a power switch (not illustrated), a first urine specification mode is started as shown in Step S401 in FIG. 13.

In this example, in the first urine specification mode, the user inputs, via an operation section 13, urine specification information indicating that urine to be measured is the urine just before sleep. When input of urine specification information is completed, a first urine measurement mode is started.

ii) In the first urine measurement mode, the user spritzes urine 99 on a sensor section 30 as shown in, for example, FIG. 2A, and depresses a scroll button 13A. Then, as shown in Step S402 in FIG. 13, the sensor section 30 acquires data indicating a Na/K ratio in one urine 99, and the data input section 12 inputs in real time the data indicating a Na/K ratio in this example.

In this example, a calculation mode is not started here, and the user turns off a power switch (not illustrated). The already input Na/K ratio is stored in a storage section 14.

iii) Next, when the user turns on a power switch (not illustrated), a second urine specification mode is started as shown in Step S403 in FIG. 13.

In this example, in the second urine specification mode, the user inputs, via the operation section 13, urine specification information indicating that urine to be measured is the first urine after wake-up. When input of urine specification information is completed, a second urine measurement mode is started.

iv) In the second urine measurement mode, the user spritzes the urine 99 on a sensor section 30 again as shown in, for example, FIG. 2A, and depresses a scroll button 13A. Then, as shown in Step S404 in FIG. 13, the sensor section 30 acquires data indicating a Na/K ratio in one urine 99, and the data input section 12 inputs in real time the data indicating a Na/K ratio in this example.

When this second data input is completed, a calculation mode is started.

v) In the calculation mode, as shown in Step S405 in FIG. 13, the control section 11 acts as a calculation section to determine an average Na/K ratio by averaging the Na/K ratio in two urines (urine just before sleep and first urine after wake-up in this example) excreted by the subject. That is, an average Na concentration is obtained by averaging a measured Na/K ratio in the urine just before sleep and a measured Na/K ratio in the first urine after wake-up. The average Na/K ratio is an object to be converted.

vi) Next, as shown in Step S406 in FIG. 13, the control section 11 acts as a calculation section to determine a Na/K ratio in total urine in one day when all the urine excreted by the subject in the one day is gathered into one volume, by performing conversion using a correlation (the correlation shown in FIG. 17B in this example) stored in a correlation storage section 15, based on the obtained average Na/K ratio.

When the object to be converted is one associated with "first urine after wake-up" and "second urine after wake-up", the correlation shown in FIG. 17A is accordingly used.

vii) Further, as shown in Step S407 in FIG. 13, the Na/K ratio obtained by conversion is stored in a calculation result storage section 16 in correspondence with a measurement date and time. At the same time, the control section 11 acts as a calculation result notification section to display on the display section 18 the Na/K ratio obtained by conversion.

viii) Then, as shown in Step S408, the control section 11 acts as an advice section to select an advice according to the Na/K ratio obtained by conversion, by referring to an advice table 17 (FIG. 21 or FIG. 22), and display on the display section 18 the advice along with the Na/K ratio obtained by conversion.

Even when a Na/K ratio in total urine in one day is determined by performing conversion based on a Na/K ratio in two urines, a high correlation (correlation coefficient) is obtained between the converted value and the measured value, and resultantly a Na/K ratio in total urine excreted by the subject in one day can be accurately determined.

When a Na/K ratio in one urine or an average Na/K ratio in two urines is used as an object to be converted, it is desirable that which is to be used should be determined in consideration of accuracy of conversion and ease of performing urine measurement by the subject. As for the order of accuracy, generally, a combination of "first urine after wake-up" and "second urine after wake-up" is ranked first, a combination of "urine just before sleep" and "first urine after wake-up" is ranked second, "second urine after wake-up" is ranked third, and "first urine after wake-up" is ranked fourth (one ranked first and one ranked second are comparable in accuracy). When the subject goes to work immediately after measuring a Na/K ratio in the first urine after wake-up at home, it is difficult in practice to measure a Na/K ratio in the "second urine after wake-up" at the workplace. Therefore, in this case, it is desirable to use a combination of "urine just before sleep" and "first urine after wake-up".

The "measured Na/K ratio in total urine in one day", which serves as a basis of the correlation stored in the correlation storage section 15, can be determined as a Na/K ratio in total urine in one day or plural days when all the urine excreted by a human over the one day or the plural days is gathered into one volume. In this case, the determined concentration is not affected by an amount of urine and a number of urine discharges in each day. The "measured Na/K ratio in total urine in one day", which serves as a basis of the correlation, may be determined by determining an average value of the concentration per day for urine excreted by a human and averaging the average value per day over plural days. In this case, urine may be gathered every day to determine an average value of the concentration per day without the necessity to gather all the urine excreted by a human over plural days into one volume. Accordingly, the correlation can be easily acquired.

Fifth Embodiment

In the fourth embodiment described above, a Na/K ratio in total urine in one day is determined by performing conversion based on a N/K ratio in two urines excreted by a subject, but the present invention is not limited thereto. A Na/K ratio in total urine in one day may be determined by performing conversion based on a Na/K ratio in three or more urine excreted by the subject over plural days.

In this case, as shown in, for example, FIGS. 18A and 18B, FIGS. 19A and 19B and FIG. 20, data indicating a correlation between an average Na/K ratio obtained using one urine, two urines, three urines, five urines or seven urines and a measured Na/K ratio in total urine in one day is stored in a correlation storage section 15.

Specifically, FIG. 18A shows a case where a relationship between a measured Na/K ratio in the first urine after wake-up in one day (abscissa x) and a measured Na/K ratio in total urine in one day (ordinate y) is approximated by a straight line (shown by a solid line in FIG. 18A), and an expression of the straight line is stored as data indicating a correlation. In this case, it is shown that the correlation coefficient is r=0.50. FIG. 18B shows a case where a relationship between an average Na/K ratio obtained by averaging the Na/K ratio in the first urines after wake-up over two days (abscissa x) and a measured Na/K ratio in total urine in two days (ordinate y) is approximated by a straight line (shown by a solid line in FIG. 18B), and an expression of the straight line is stored as data indicating a correlation. In this case, it is shown that the correlation coefficient is r=0.65. FIG. 19A shows a case where a relationship between an average Na/K ratio obtained by averaging the Na/K ratio in the first urines after wake-up over three days (abscissa x) and a measured Na/K ratio in total urine in three days (ordinate y) is approximated by a straight line (shown by a solid line in FIG. 19A), and an expression of the straight line is stored as data indicating a correlation. In this case, it is shown that the correlation coefficient is r=0.72. FIG. 19B shows a case where a relationship between an average Na/K ratio obtained by averaging the Na/K ratio in the first urines after wake-up over five days (abscissa x) and a measured Na/K ratio in total urine in five days (ordinate y) is approximated by a straight line (shown by a solid line in FIG. 19B), and an expression of the straight line is stored as data indicating a correlation. In this case, it is shown that the correlation coefficient is r=0.72. FIG. 20 shows a case where a relationship between an average Na/K ratio obtained by averaging the Na/K ratio in the first urines after wake-up over seven days (abscissa x) and a measured Na/K ratio in total urine in seven days (ordinate y) is approximated by a straight line (shown by a solid line in FIG. 20), and an expression of the straight line is stored as data indicating a correlation. In this case, it is shown that the correlation coefficient is r=0.68.

Here, when a Na/K ratio in total urine in one day is determined by performing conversion based on a Na/K ratio in one urine excreted by the subject, the flow of control by the control section 11 of the urine component analysis device 90 is exactly the same as the flow shown in FIG. 12. Here, when a Na/K ratio in total urine in one day is determined by performing conversion based on a Na/K ratio in plural urines excreted by the subject, the flow of control by a control section 11 of the urine component analysis device 90 is the same as the flow in FIG. 13 except that the urine specification mode of Step S401 and the urine measurement mode of Step S402 are repeated a number of times which is equal to a number of urine measurements. Processing from Step S405 through to Step S408 is similar to that in the fourth embodiment.

Also in this case, a high correlation (correlation coefficient) is obtained between the converted value and the measured value, so that a Na/K ratio in total urine excreted by the subject in one day can be accurately determined.

As a whole, for the number of times and the period (number of days) in which data about a concentration of a specific component in the urine excreted by the subject is measured, one urine or plural urines per day may be measured over one day or plural days. When the number of measurements and the number of measurement days are increased, accuracy of the Na/K ratio obtained by conversion can be enhanced. The subject is not required to perform measurement every day during the measurement period. For example, measurement may be performed only six times during a measurement period of seven days.

In the embodiments described above, the user inputs, via an operation section 13, urine specification information indicating whether urine to be measured is the first urine after wake-up or the second urine after wake-up or the urine just before sleep, but the present invention is not limited thereto. The control section 11 may act as a urine determination section to determine whether the one urine or the plural urines excreted by the subject are the first urine after wake-up or the second urine after wake-up or the urine just before sleep, in accordance with a time at which data about a Na concentration and a K concentration is input. In this way, time and labor of inputting urine specification information by the user can be saved.

In this case, it is desirable that the user uses the control section 13 as a sleep time zone setting section to set a sleep time zone during which the subject gets sleep. When the sleep time zone is set as described above, the control section 11 can act as a urine determination section to determine whether the one urine or the plural urines excreted by the subject are the first urine after wake-up or the second urine after wake-up or the urine just before sleep by comparing a time, at which data about a Na concentration and a K concentration is input, with the sleep time zone. Accordingly, accuracy of determination by the control section 11 as a urine determination section is enhanced.

Setting input of a sleep time zone can be performed in the same manner as in the case of input of the foregoing "urine specification", "blood pressure", "BMI" and "urine discharge date and time" etc. That is, when the user continuously depresses a scroll button 13A for 3 or more seconds subsequent to turning on the power switch, the control section 11 displays on a display section 18 an option of whether information of "sleep time zone" is to be input subsequent to "urine specification", "blood pressure" and "BMI" etc. When the user rotates the scroll button 13A as the option is displayed, values of commencement of "sleep time zone" are displayed on the display section 18 in the ascending or descending manner. When the user depresses the scroll button 13A, a time displayed at this time is input as the commencement of "sleep time zone". When the user subsequently rotates the scroll button 13A, values of termination of "sleep time zone" are displayed on the display section 18 in the ascending or descending manner. When the user depresses the scroll button 13A, a time displayed at this time is input as the termination of "sleep time zone". In this manner, a "sleep time zone" is set. The sleep time zone is stored in a storage section 14.

In the embodiments described above, the display section 18 is provided for notification of various kinds of information, but the present invention is not limited thereto. For example, a speaker may be provided in addition to the display section 18 or in place of the display section 18. In this case, the user can be notified of a Na/K ratio calculated by the control section 11 and an advice appropriate to the Na/K ratio by voice through the speaker.

Sixth Embodiment

The present inventors have further conducted experiments while increasing the number of measurements and the number of measurement days. As a result, it has been found that by selecting, as an object to be converted, data of two or more measurements in mutually different time zones wherever possible in mutually different days wherever possible when measurement data (Na/K ratio) of plural urines over plural days is used, accuracy of the Na/K ratio obtained by conversion can be enhanced.

For example, FIG. 23 shows a correlation between a number of measurements and a correlation coefficient when a Na/K ratio in one urine at per day is measured up to 7 days. The abscissa in the figure represents a number of measurements (number of actual measurements) of a Na/K ratio in one urine excreted by a subject. The ordinate in the figure represents a correlation coefficient r between an average Na/K ratio obtained by averaging the measured Na/K ratio in one urine by a number of measurements (represented by the abscissa) and a measured Na/K ratio in total urine in seven days. Here, when the number of measurements is less than 7, an average Na/K ratio for days of from the first day to a day corresponding to the number of measurements is used for conversion. For example, when the number of measurements is 4, an average Na/K ratio for four measurements of from the first day to the fourth day is used for conversion. In the present situation of the medical field, the Na/K in total urine in seven days when all the urine excreted by a human in the seven days is gathered into one volume serves as a basis for evaluation of health conditions of the human.

The ○ mark in the figure denotes a result when the measurement object in each day is limited to "first urine after wake-up". The □ mark in the figure denotes a result when the measurement object in each day is limited to "second urine after wake-up". The Δ mark in the figure denotes a result when the measurement object in each day is limited to "urine just before sleep". The ◇ mark in the figure denotes a result when the measurement object in each day is random, i.e. spot urine.

It is apparent from FIG. 23 that as the number of measurements of a Na/K ratio in one urine is increased, the correlation efficient r is increased, so that accuracy of conversion is enhanced. However, when the number of measurements is 5 or more, the correlation coefficient r is almost saturated. The correlation coefficient r is higher (particularly when the number of measurements is 3 or more) when the measurement object is random, i.e. spot urine than when the measurement object is limited to "first urine after wake-up", "second urine after wake-up" or "urine just before sleep".

Therefore, it is desirable that a control section 11 which acts as a calculation section select, as an object to be converted, data of two or more measurements in mutually different time zones in mutually different days among measurement data about the subject stored in a storage section 14. As a result, accuracy of conversion is enhanced. The "time zone" refers to a time zone obtained by dividing a day into two or more segments, and refers to, for example, a time zone of every hour, every two hours or every three hours.

It is desirable that the control section 11 select, as an object to be converted, data of at least five measurements in mutually different time zones in mutually different days among measurement data about the subject stored in the storage section 14, particularly a later-described measurement data storage section 14A. As a result, accuracy of conversion is enhanced. When data of at least five measurements is used, accuracy of conversion is almost saturated as described above. Therefore, for example, when it is provided beforehand that data of at least five measurements is used, the subject can avoid taking excessive time and labor for urine discharge and measurement.

It is desirable that the mutually different days include at least seven days. In this case, the control section 11 selects, as an object to be converted, data of two or more measurements in mutually different time zones in at least seven mutually different days when selecting measurement data in plural days among measurement data about the subject stored in the storage section 14, particularly the later-described measurement data storage section 14A. As a result, accuracy of conversion is enhanced. The reason why measurement data in at least seven days is selected is that one week (seven days) constitutes a cycle of life (including dietary life) for many people.

It is desirable that the mutually different days include mutually different days of week. In this case, the control section 11 selects, as an object to be converted, data of two or more measurements in mutually different time zones in mutually different days of week when selecting measurement data in plural days among measurement data about the subject stored in the storage section 14, particularly the later-described measurement data storage section 14A. As a result, accuracy of conversion is enhanced. The reason why measurement data in mutually different days of week is selected is that one week (seven days) constitutes a cycle of life (including dietary life) for many people as described above.

FIGS. 24A and 24B, FIGS. 25A and 25B and FIG. 26 show a result of examining a Na/K ratio in total urine in one day, which is obtained by conversion in the control section 11 using one spot urine to five spot urines, respectively, by using a measured Na/K ratio in total urine in one day (it is actually a Na/K ratio in total urine in seven days, but described as a Na/K ratio in total urine in one day; the same hereinafter).

Specifically, FIG. 24A shows a result of matching a Na/K ratio in total urine in one day, which is obtained by conversion using one spot urine, with a measured Na/K ratio in total urine in one day. At this time, the correlation coefficient is $r=0.53$ and the standard deviation is $SD=1.13$. FIG. 24B shows a result of matching a Na/K ratio in total urine in one day, which is obtained by conversion using two spot urines at mutually different dates and times, with a measured Na/K ratio in total urine in one day. At this time, the correlation coefficient is $r=0.69$ and the standard deviation is $SD=1.04$. FIG. 25A shows a result of matching a Na/K ratio in total urine in one day, which is obtained by conversion using three spot urines at mutually different dates and times, with a measured Na/K ratio in total urine in one day. At this time, the correlation coefficient is $r=0.76$ and the standard deviation is $SD=0.81$. FIG. 25B shows a result of matching a Na/K ratio in total urine in one day, which is obtained by conversion using four spot urines at mutually different dates and times, with a measured Na/K ratio in total urine in one day. At this time, the correlation coefficient is r=0.83 and the standard deviation is SD=0.67. FIG. 26 shows a result of matching a Na/K ratio in total urine in one day, which is obtained by conversion using five spot urines at mutually different dates and times, with a measured Na/K ratio in total urine in one day. At this time, the correlation coefficient is r=0.85 and the standard deviation is SD=0.63.

Thus, as the number of measurements of a Na/K ratio in one urine is increased from 1 to 5, it could be confirmed that the correlation efficient r is increased and the standard deviation SD is reduced, so that accuracy of conversion is enhanced.

Even when the control section 11 uses measurement data of five urines as an object to be converted, accuracy of conversion is not so much enhanced if there is a deviation in the urine discharge time zone or in the urine discharge day.

For example, FIG. 27A shows a result of matching a Na/K ratio in total urine in one day, which is obtained by conversion using only the first urines after wake-up in five days as five urines, with a measured Na/K ratio in total urine in one day. At this time, the correlation coefficient is r=0.67 and the standard deviation is SD=1.00. FIG. 27B shows a result of matching a Na/K ratio in total urine in one day, which is obtained by conversion using only the urines just before sleep in five days as five urines, with a measured Na/K ratio in total urine in one day. At this time, the correlation coefficient is r=0.73 and the standard deviation is SD=0.86. FIG. 28 is a view showing a result of matching a Na/K ratio in total urine in one day, which is obtained by conversion using only every urine excreted in the same day, with a measured Na/K ratio in total urine in one day. At this time, the correlation coefficient is r=0.73 and the standard deviation is SD=0.85.

In the case of FIGS. 27A and 27B and FIG. 28, the correlation coefficient r is low and the standard deviation SD is high as compared to the case of FIG. 26. Therefore, even when measurement data of plural urines is used as an object to be converted, accuracy of conversion is not so much enhanced.

It could be confirmed from these results that by selecting data of two or more measurements in mutually different time zones wherever possible in mutually different days wherever possible when measurement data of urine over plural days is used, accuracy of the Na/K ratio obtained by conversion can be enhanced.

The control section 11 can include, as data of two or more measurements selected, the last measured Na/K ratio in one urine among measurement data about the subject stored in the measurement data storage section. As a result, the result of conversion obtained by the calculation section 11 reflects the latest health conditions of the subject.

Seventh Embodiment

FIG. 29 shows a block configuration of a urine component analysis device 90B suitable for obtaining a result of conversion of a Na/K ratio using data of two or more urine measurements over two or more days, the urine component analysis device 90B being a modification of the urine component analysis device 90 of FIG. 1. In FIG. 29, constituent elements same as those in FIG. 1 are given the same symbols.

The urine component analysis device 90B includes a clock 41, a network communication section 42, a NFC communication section 43 and an alarm section 44 in addition to the constituent elements of the urine component analysis device 90 of FIG. 1. Further, the urine component analysis device 90B includes in a storage section 14 a measurement data storage section 14A to store a measurement data table with respect to the urine component analysis device 90 of FIG. 1.

The clock 41 counts the present date and time.

The network communication section 42 sends information from the control section 11 to other devices (not illustrated) on the network via a wireless communication line such as a 3G (third generation mobile communication system) or Wi-Fi (registered trademark) in this example, and receives information sent from other devices (not illustrated) on the network and delivers the received information to the control section 11. In this way, health-related information can be provided to a user in cooperation with other devices via, for example, Internet. The communication line is not limited to a wireless line, but may be a wired line.

The NFC (Near Field Communication; short range wireless communication) communication section 43 acts as a personal authentication section with the control section 11 to identify a subject when an ID (identification) card carried by the subject is brought close thereto. Thus, by discriminating measurement data about the subject on an individual basis, the urine component analysis device 90B can be shared by two or more subjects. For identifying the subject, the subject may input an ID number via an operation section 13 in place of the NFC communication section 43, or a reading section to read fingerprints or the like may be provided to perform biometric authentication.

The alarm section 44 includes a buzzer in this example, and sounds an alarm in response to a control signal from the control section 11.

The measurement data storage section 14A stores, for example, the following measurement data table.

| (Measurement Data Table) | | | |
|---|---|---|---|
| Subject | Urine discharge date and time | Measurement date and time | Na/K ratio in one urine |
| Taro Yamada | 2011/10/21 07:00 | 2011/10/21 07:00 | 4.5 |
| Taro Yamada | 2011/10/21 16:00 | 2011/10/21 16:00 | 4.8 |
| . . . | . . . | . . . | . . . |
| Hanako Suzuki | 2011/12/01 07:00 | 2011/12/01 18:00 | 3.5 |
| Hanako Suzuki | 2011/12/02 11:00 | 2011/12/02 18:00 | 3.7 |
| . . . | . . . | . . . | . . . |

As is apparent from the above, the measurement data table stores, for each subject, a Na/K ratio in each one urine over one day or plural days, which is obtained via a data input section 12, in correspondence with a urine discharge date and time at which each urine is excreted and a measurement date and time at which the Na/K of the urine is measured, as measurement data about the subject.

Here, measurement data of the subject "Taro Yamada" was recorded in the following manner. First, Taro Yamada brought an ID card close to the NFC communication section 43, so that it was authenticated that the subject is "Taro Yamada". Subsequent to the personal authentication, Taro Yamada spritzed urine on a sensor section 30 for measurement, the sensor section 30 directly acquired a Na/K ratio in the one urine and a data input section 12 inputted in real time data indicating the Na/K ratio. At the same time, the present date and time counted by the clock 41 was captured as a urine discharge date and time and a measurement date and time. As a result, for the measurement data of the subject "Taro Yamada", the urine discharge date and time and the measurement date and time are identical to each other. For example, for the first measurement data of the subject "Taro Yamada", the urine discharge date and time: 2011/10/21 07:00 and the measurement date and time: 2011/10/21 07:00 are identical to each other. The Na/K ratio in the one urine was 4.5. In this case, time and labor of inputting the urine discharge date and time by the user can be saved.

Measurement data of the subject "Hanako Suzuki" was recorded in the following manner. Hanako Suzuki excreted urine for measurement, and stored the urine in a container on a temporary basis. Thereafter, Hanako Suzuki brought an ID card close to the NFC communication section 43, so that it was authenticated that the subject is "Hanako Suzuki". Subsequent to this personal authentication, Hanako Suzuki inputted a urine discharge date and time for the urine using the operation section 13 as a urine discharge date and time input section. Subsequently, Hanako Suzuki immersed the sensor section 30 in the urine in the container, the sensor section 30 directly acquired a Na/K ratio in the one urine and a data input section 12 inputted in real time data indicating the Na/K ratio. As a result, for the measurement data of the subject "Hanako Suzuki", the measurement date and time is preceded by the urine discharge date and time. For example, for the first measurement data of the subject "Hanako Suzuki", the measurement date and time: 2011/12/01 18:00 is preceded by the urine discharge date and time: 2011/12/01 7:00. The Na/K ratio in the one urine was 3.5. Input of the urine discharge date and time may be performed after the sensor section 30 is immersed in urine (after the measurement date and time).

Thus, when the measurement data storage section 14A stores a measurement data table, various forms of use are possible.

The control section 11 can act as a calculation section to obtain the foregoing result of conversion using the measurement data table.

Input of a urine discharge date and time can be performed in the same manner as in the case of input of the foregoing "urine specification", "blood pressure" and "BMI" etc. That is, when the user continuously depresses a scroll button 13A for 3 or more seconds subsequent to turning on the power switch, the control section 11 displays on a display section 18 an option of whether information of "urine discharge date and time" is to be input subsequent to "urine specification", "blood pressure" and "BMI" etc. When the user rotates the scroll button 13A as the option is displayed, values of input candidates of "urine discharge date and time" are displayed on the display section 18 in the ascending or descending manner. When the user depresses the scroll button 13A, a value displayed at this time is input as a urine discharge date and time.

Eighth Embodiment

FIG. 30 shows a flow of operations for display of a history and recommendation of urine by a urine component analysis device 90B shown in FIG. 29. A control section 11 acts as a urine discharge history notification section and a urine discharge recommendation date and time notification section to execute this flow.

i) First, a Na/K ratio in one urine of a subject is measured as shown in Step S501 in FIG. 30, and a urine discharge date and time, a measurement date and time and the Na/K ratio for the one urine are stored in a measurement data storage section 14A as shown in Step S502. By repeating Steps S501 and S502, a measurement data table as described above is built in the measurement data storage section 14A.

ii) Next, the control section 11 acts as a histogram preparation section to prepare a histogram indicating a history of date and time of urine discharge by the subject within a period of one day or plural days based on the urine discharge date and time stored in the measurement data table.

The histogram may indicate the history of date and time of urine discharge by the subject as a "number of measurements" for each day of week as shown in, for example, FIG. 32A, or may indicate the history of date and time of urine discharge by the subject as a "number of measurements" for each time zone as shown in FIG. 32B. In this example, both the histogram for each day of week as in FIG. 32A and the histogram for each time zone as in FIG. 32B are prepared.

In this example, the histogram for each day of week in FIG. 32A shows that the subject has a record of discharging urine and performing measurement one time or more in each of Monday, Wednesday, Friday, Saturday and Sunday, but does not have a record (has no record) of discharging urine and performing measurement in Tuesday and Thursday. The histogram for each time zone in FIG. 32B shows that the subject has a record of discharging urine and performing measurement one time or more in each of (one-hour) time zones between 0:00 and 1:00, between 6:00 and 7:00, between 7:00 and 8:00, between 20:00 and 21:00, between 21:00 and 22:00, between 22:00 and 23:00 and between 23:00 and 24:00 but does not have a record (has no record) of discharging urine and performing measurement in a time zone between 8:00 and 10:00 and a time zone between 11:00 and 20:00.

iii) Next, as shown in Step S504 in FIG. 30, the control section 11 acts as a urine discharge recommendation date and time determination section to determine a urine discharge recommendation date and time for the subject to discharge urine, based on the urine discharge date and time stored in the measurement data table, so that measurement data about the subject can be obtained in mutually different time zones of one day or in mutually different time zones in mutually different days of plural days.

Specifically, a day of week with no record of discharging urine and performing measurement and a time zone with no record of discharging urine and performing measurement in the measurement data table are determined as a urine discharge recommendation date and time for the subject to discharge urine.

For example, there is no record of discharging urine and performing measurement in Tuesday and Thursday in the examples in FIGS. 32A and 32B. There is no record of discharging urine and performing measurement in a time zone between 1:00 and 6:00, a time zone between 8:00 and 10:00 and a time zone between 11:00 and 20:00. Therefore, Tuesday and Thursday, and a time zone between 1:00 and 6:00, a time zone between 8:00 and 10:00 and a time zone between 11:00 and 20:00 are determined as a urine discharge recommendation date and time for the subject to discharge urine.

iv) Next, as shown in Step S505 in FIG. 30, the control section 11 acts as a urine discharge recommendation date and time notification section to give a notification by displaying on a display section 18 a histogram indicating a history of date and time of urine discharge by the subject and a urine discharge recommendation date and time for the subject to discharge urine.

By seeing a histogram as in, for example, FIGS. 32A and 32B, the subject as a user can intuitively recognize through visual sensation a day of week and a time zone during which the subject did not discharge urine and perform measurement in the past. The subject is encouraged to discharge urine and perform measurement hereafter in a day of week and a time zone during which the subject did not discharge urine and perform measurement in the past. Therefore, the subject can keep it in mind to discharge urine and perform measurement hereafter such days of week and time zones.

In this example, a message of "discharge urine and perform measurement on Tuesday and Thursday and in a time zone between 1:00 and 6:00, a time zone between 8:00 and 10:00 and a time zone between 11:00 and 20:00" may be displayed as the urine discharge recommendation date and time for the subject to discharge urine. Alternatively, a message with a date and time specified therein, for example, a message of "discharge urine and perform measurement at around 11:00 on May 1, 2012 (Tuesday)" may be displayed.

An alarm section 44 may be caused to sound an alarm at a urine discharge recommendation date and time instead of or in addition to displaying on the display section 18 a urine discharge recommendation date and time for the subject to discharge urine. In this case, the subject is encouraged to discharge urine and perform measurement at a date and time when an alarm is sounded. Alternatively, a network communication section 42 may be caused to send a mail, which encourages the subject to discharge urine, to the subject at a urine discharge recommendation date and time. In this case, the subject is encouraged to discharge urine and perform measurement at a date and time when the mail is received on, for example, the subject's mobile phone or smart phone. Prior to a urine discharge recommendation date and time, a mail with the urine discharge recommendation date and time written therein may be sent to the subject to encourage the subject to discharge urine and perform measurement at the urine discharge recommendation date and time. When the subject carries a smart phone, the subject may be notified of a urine discharge recommendation date and time via software (including a social networking service (SNS) such as Facebook (registered trademark)). In any case, the subject may be notified of a urine discharge recommendation date and time for the subject to discharge urine and perform measurement, either at the urine discharge recommendation date and time or prior to the urine discharge recommendation date and time.

It is considered that execution of an operation to sound an alarm or send a mail should be avoided in, for example, a time zone during which the subject sleeps because the subject is annoyed. In this case, it is desirable that subject use the operation section 13 as a notification prohibition time zone setting section to set a notification prohibition time zone (e.g. 23:00 to 07:00) during which an operation to sound an alarm or send a mail by the control section 11 should be prohibited. The notification prohibition time zone is stored in the storage section 14.

Setting input of a notification prohibition time zone can be performed in the same manner as in the case of input of the foregoing "urine specification", "blood pressure", "BMI" and "urine discharge date and time" etc. That is, when the user continuously depresses a scroll button 13A for 3 or more seconds subsequent to turning on the power switch, the control section 11 displays on a display section 18 an option of whether information of "notification prohibition time zone" is to be input subsequent to "urine specification", "blood pressure" and "BMI" etc. When the user rotates the scroll button 13A as the option is displayed, values of commencement of "notification prohibition time zone" are displayed on the display section 18 in the ascending or descending manner. When the user depresses the scroll button 13A, a time displayed at this time is input as the commencement of "notification prohibition time zone". When the user subsequently rotates the scroll button 13A, values of termination of "notification prohibition time zone" are displayed on the display section 18 in the ascending or descending manner. When the user depresses the scroll button 13A, a time displayed at this time is input as the termination of "notification prohibition time zone". In this manner, a "notification prohibition time zone" is set.

FIG. 31 shows a flow of operations by the control section 11 when such a notification prohibition time zone is set.

First at Step S601, the control section 11 determines whether or not a urine discharge recommendation date and time is given (determined). When a urine discharge recommendation date and time is given (YES at Step S601), the control section 11 determines whether or not the current time belongs to a notification prohibition time zone (Step S602) by referring to the clock 41. When the current time does not belong to the notification prohibition time zone (NO at Step S602), a notification of urine discharge recommendation date and time is given (Step S603). This notification encourages the subject to discharge urine and perform measurement.

On the other hand, when the current time belongs to the notification prohibition time zone (YES at Step S602), passage of time is awaited, and a notification of urine discharge recommendation date and time is given (Step S603) at the time when the current time goes out of the notification prohibition time zone (NO at Step S602). In this way, a situation can be avoided in which the subject is forced to discharge urine by the alarm or mail in a time zone during which the subject sleeps.

Ninth Embodiment

When in the urine component analysis device of FIG. 29, past measurement data is not stored in a measurement data storage section 14A (e.g. a user uses the device for the first time), a future urine discharge recommendation date and time may have to be determined without depending on past measurement data.

In this case, a control section 11 acts as a second urine discharge recommendation date and time determination section to explain how to determine a urine discharge recommendation date and time for a subject to discharge urine by using a urine collection plan table 180 shown in FIG. 33. In the urine collection plan table 180, plural days, at least a week (seven days) from Monday to Sunday in this example, are shown on a table head 180a. Time zones in the morning, in the day and in the evening, which range from a wake-up time to a bedtime of the subject, are shown on a table side 180b. On a table body 180c, urine collection container marks 181 representing a urine collection container containing urine are shown while being arranged for each day of week on the table head 180a and for each time zone on the table side 180b (marks 181 are appropriately replaced by three-dots . . . ). The current date and time (before wake-up time on Monday in this example) is shown by a ☆ mark 182.

In the example in FIG. 33, immediately before the wake-up time on Monday, i.e. the current date and time, the control section 11 acts as the second urine discharge recommendation date and time determination section to determine, at random by lot, a urine discharge recommendation date and time for the subject to discharge urine during a future week (the "future" means that a day to which the current time belongs may be included when the current time precedes the wake-up time). On the table body 180c, a urine discharge recommendation date and time determined in this manner is shown by thick-bordered box marks 183a,183b,183c,183d, 183e and 183f. Specifically, a urine collection container mark 181 (or three-dots . . . ) corresponding to a time zone including the urine discharge recommendation date and time is surrounded by thick-bordered box marks 183a,183b,183c, 183d,183e and 183f. For example, the thick-bordered box mark 183b indicates that the urine discharge recommendation date and time belongs to a time zone just before sleep on Tuesday. The thick-bordered box mark 183c indicates that the urine discharge recommendation date and time belongs to a time zone including the midday on Wednesday. It is indicated that the urine discharge recommendation date and time belongs to a time zone immediately after wake-up on Thursday.

As shown in a urine collection plan table 180' in FIG. 34, the control section 11 may determine, at random by lot, a urine discharge recommendation date and time for the subject to discharge urine in one day immediately before the wake-up time in the day, which is the current date and time. In the example in FIG. 34, the thick-bordered box mark 183 indicates that the determined urine discharge recommendation date and time belongs to a time zone just before sleep.

The control section 11 acts as a urine discharge recommendation date and time notification section to notify the subject of the determined urine discharge recommendation date and time. The subject can be notified in various manners, for example by displaying the urine discharge recommendation date and time on a display section 18 or sounding an alarm as described in connection with Step S505 in FIG. 30.

In the above example, the time at which the control section 11 determines a urine discharge recommendation date and time is immediately before the wake-up time in the first day (or one day) in a period (target period) shown by the urine collection plan table 180, 180', but the present invention is not limited thereto. The time at which the control section 11 determines a urine discharge recommendation date and time is not limited as long as it is before the wake-up time in the first day (one day) in a target period. For example, it may be at the night before the first day (or one day) in a target period.

Tenth Embodiment

FIG. 35A shows an aspect of a urine component analysis device (denoted by symbol 90C as a whole) of another embodiment of the present invention.

The urine component analysis device 90C is a toilet bowl-mounted type urine component analysis device, and includes a housing 10C attached on a circumference of a toilet bowl 198 (on a side surface of a water tank 196 in this example), and a sensor section 30C disposed in a space inside the toilet bowl 198.

Constituent elements similar to those in the housing 10 of the urine component analysis device 90B of FIG. 29 are mounted in the housing 10C. The sensor section 30C is supported by an arm 32. The arm 32 extends from the vicinity of the base of a toilet seat cover 197 to substantially the center of the inside of the toilet bowl 198. In this way, the sensor section 30C is held at a position above a water pool 199.

The sensor section 30C is a constituent element identical to the sensor section 30 in FIG. 29, and is connected to a data input section 12 in the housing 10C by wiring (not illustrated) in this example. In this way, the urine component analysis device 90C can be operated in the same manner as in the case of the urine component analysis device 90B of FIG. 29.

For example, when the toilet bowl-mounted type urine component analysis device 90C is used, urine is spritzed on the sensor section 30C in a space inside the toilet bowl 198 when the subject as a user discharges urine. In this way, the sensor section 30C comes into contact with urine excreted by the subject to acquire data about concentrations of the first specific component and the second specific component, a Na/K ratio in this example. According to the toilet bowl-mounted type urine component analysis device 90C, the subject as a user is not required to provide a container to store urine, such as a paper cup.

The housing 10 is not necessarily provided on the side surface of the water tank 196, but may be provided on the circumference of the toilet bowl 198 or at any location in a room where the toilet bowl 198 is provided. The housing 10 may be incorporated integrally with the water tank 196 or the toilet bowl 198.

The sensor section 30C may be disposed in a space inside the toilet bowl 198 in a form shown in FIG. 35B. In the example in FIG. 35B, the sensor section 30C is attached at the center of a long and narrow bar 33. Arc-shaped hooks 34A and 34B are formed integrally at both ends of the bar 33, respectively. The hooks 34A and 34B are each hung at the upper edge of the toilet bowl 198. In this way, the bar 33 is laid between portions on the upper edge of the toilet bowl 198, which face each other. In this manner, the sensor section 30C is held at a position above the water pool 199.

The bar 33 in FIG. 35B may be deformed downward in a convex form rather than extending straight.

Eleventh Embodiment

FIG. 36 shows a block configuration of a urine component analysis device (denoted by symbol 90A as a whole) of another embodiment of the present invention. For easy understanding, constituent elements same as those in FIG. 1 are given the same symbols, and duplicated explanations are omitted.

The urine component analysis device 90A includes a housing 10A, a control section 11 mounted and stored in the housing 10, a storage section 14 and a communication section 20.

In this example, the housing 10A is formed as a tower type housing to be placed on a desk or a floor.

The communication section 20 includes a data input section 12 and a calculation result sending section 19. The communication section 20 is connected via a wireless or wired communication line 300 to a mobile phone or personal computer (PC) 200 present outside the housing 10A. In this example, a subject as a user uses the mobile phone or PC 200 by operating an operation section 201 (keyboard, ten key and mouse etc.).

The data input section 12 receives data about concentrations of two specific components (Na concentration and K concentration in this example) in the urine excreted by the subject via the communication line 300 from the mobile phone or PC 200, and inputs the data. An ID number for identifying a subject, a Na/K ratio in each one urine, and a urine discharge date and time and measurement date and time for the one urine may be input in correspondence with one another so that the foregoing measurement data table is built in the storage section 14.

The calculation result sending section 19 outputs a calculation result (Na/K ratio in this example) calculated by the control section 11 to the mobile phone or PC 200 via the communication line 300.

As a result, the urine component analysis device 90A is formed as a server type urine component analysis device that performs input of data and output of a calculation result via the wireless or wired communication line 300.

For example, when the server type urine component analysis device 90A is used, the subject as a user at a remote location away from the housing 10A acquires data about a Na concentration and a K concentration by a commercially available sensor etc. The data is input by the data input section 12 via the wireless or wired communication line 300 from the mobile phone or PC 200 which is operated by the subject. At the same time, the subject inputs, via the operation section 201 of the mobile phone or PC 200, urine specification information indicating whether urine to be measured is the first urine after wake-up or the second urine after wake-up or the urine just before sleep. The urine specification information is input from the mobile phone or PC 200 to the control section 11 via the wireless or wired communication line 300 and via the communication section 20. As a result, a Na/K ratio in total urine in one day when all the urine excreted by the subject in the one day is gathered into one volume is calculated by the control section 11. The Na/K ratio calculated by the calculation section 11 is output, together with an advice appropriate to the Na/K ratio, to the mobile phone or PC 200 of the subject at a remote location away from the housing 10A via the wireless or wired communication line 300 by the calculation result sending section 19. As a result, the subject can know the Na/K ratio calculated by the control section 11 and the advice appropriate to the Na/K ratio, through a display section (LCD etc.) 202 of the mobile phone or PC 200, at a location where the subject is present.

Thus, the server type urine component analysis device 90A can be easily used by a user at a remote location away from the housing 10A.

In the embodiments described above, the first specific component and the second specific component in urine to be determined by conversion are sodium (Na) and potassium (K), respectively, but the present invention is not limited thereto. The first specific component and the second specific component may be each one of, for example, sodium, potassium, calcium and glucose, the first and second specific components being mutually different. When these components are obtained, an advice useful for improvement of life habits, such as dietary life, of the subject can be given. Particularly, when the first specific component and the second specific component are sodium (Na) and potassium (K), respectively, a Na/K ratio obtained by conversion can be used as information for improving hypertension of the subject.

As described above, a urine component analysis device of the present invention comprises:

a correlation storage section which stores data indicating a correlation between a concentration ratio between a first specific component and a second specific component in one urine excreted by a human and a concentration ratio between the first specific component and the second specific component in total urine in one day when all the urine excreted by the human in the one day is gathered into one volume;

a data input section which inputs data indicating a concentration ratio between the first specific component and the second specific component in one urine excreted by a subject; and a calculation section which determines a concentration ratio between the first specific component and the second specific component in total urine in one day when all the urine excreted by the subject in the one day is gathered into one volume, by performing conversion using the correlation stored in the correlation storage section, based on the concentration ratio between the first specific component and the second specific component in the one urine of the subject obtained via the data input section.

According to the urine component analysis device of the present invention, the correlation storage section stores data indicating a correlation between a concentration ratio between a first specific component and a second specific component in one urine excreted by a human and a concentration ratio between the first specific component and the second specific component in total urine in one day when all the urine excreted by the human in the one day is gathered into one volume. The data input section inputs data indicating a concentration ratio between the first specific component and the second specific component in one urine excreted by a subject. The calculation section determines a concentration ratio between the first specific component and the second specific component in total urine in one day when all the urine excreted by the subject in the one day is gathered into one volume, by performing conversion using the correlation stored in the correlation storage section, based on the concentration ratio between the first specific component and the second specific component in the one urine of the subject obtained via the data input section.

Here, in the urine component analysis device, a concentration ratio between the first specific component and the second specific component in total urine in one day is determined by performing conversion based on a concentration ratio between the first specific component and the second specific component in one urine excreted by the subject, and therefore it is not necessary to actually measure an amount of urine excreted by the subject. When a concentration ratio between the first specific component and the second specific component in at least one urine excreted by the subject is obtained as input data, a result of conversion is obtained. Therefore, according to the urine component analysis device, a concentration ratio between two specific components in total urine excreted by the subject in one day can be easily and conveniently determined.

In the urine component analysis device of one embodiment, the correlation storage section stores data indicating a correlation between an average concentration ratio obtained by averaging the concentration ratio between the first specific component and the second specific component in plural urines excreted by the human over one day or plural days and a concentration ratio between the first specific component and the second specific component in total urine in one day or plural days when all the urine excreted by the human over the one day or the plural days is gathered into one volume; and the calculation section obtains an average concentration ratio by averaging the concentration ratio between the first specific component and the second specific component in the plural urines excreted by the subject over one day or plural days, and defines the average concentration ratio as an object for the conversion.

In the urine component analysis device of this embodiment, the correlation storage section stores data indicating a correlation between an average concentration ratio obtained by averaging the concentration ratio between the first specific component and the second specific component in plural urines excreted by the human over one day or plural days and a concentration ratio between the first specific component and the second specific component in total urine in one day or plural days when all the urine excreted by the human over the one day or the plural days is gathered into one volume. The calculation section obtains an average concentration ratio by averaging the concentration ratio between the first specific component and the second specific component in the plural urines excreted by the subject over one day or plural days, and defines the average concentration ratio as an object for the conversion. That is, the calculation section determines a concentration ratio between the first specific component and the second specific component in total urine in one day when all the urine excreted by the subject in the one day is gathered into one volume, by performing conversion using the correlation stored in the correlation storage section, based on the obtained average concentration ratio between the first specific component and the second specific component. In this case, accuracy of the calculated concentration ratio between the first specific component and the second specific component in the total urine in the one day is enhanced.

In the urine component analysis device of one embodiment, the correlation storage section stores data indicating a correlation between an average concentration ratio obtained by averaging the concentration ratio between the first specific component and the second specific component in plural urines excreted by the human over one day or plural days and a concentration ratio between the first specific component and the second specific component, which serves as a basis;

the concentration ratio between the first specific component and the second specific component, which serves as a basis, is obtained by determining an average value per day of concentration ratios between the first specific component and the second specific component for urine excreted by the human, and averaging the average value per day over plural days; and the calculation section obtains an average concentration ratio by averaging the concentration ratio between the first specific component and the second specific component in the plural urines excreted by the subject over one day or plural days, and defines the average concentration ratio as an object for the conversion.

In the urine component analysis device of this embodiment, the correlation storage section stores data indicating a correlation between an average concentration ratio obtained by averaging the concentration ratio between the first specific component and the second specific component in plural urines excreted by the human over one day or plural days and a concentration ratio between the first specific component and the second specific component, which serves as a basis. The calculation section obtains an average concentration ratio by averaging the concentration ratio between the first specific component and the second specific component in the plural urines excreted by the subject over one day or plural days, and defines the average concentration ratio as an object for the conversion. That is, the calculation section determines a concentration ratio between the first specific component and the second specific component in total urine in one day when all the urine excreted by the subject in the one day is gathered into one volume, by performing conversion using the correlation stored in the correlation storage section, based on the obtained average concentration ratio between the first specific component and the second specific component. In this case, accuracy of the calculated concentration ratio between the first specific component and the second specific component in the total urine in the one day is enhanced. Furthermore, the concentration ratio between the first specific component and the second specific component, which serves as a basis, is obtained by determining an average value per day of concentration ratios between the first specific component and the second specific component for urine excreted by the human, and averaging the average value per day over plural days. That is, when the correlation is determined for urine over plural days, urine may be gathered every day to determine an average value per day of concentration ratios between the first specific component and the second specific component without the necessity to gather all the urine excreted by a human over plural days into one volume. Accordingly, the correlation can be easily acquired.

In another aspect, the urine component analysis device of the present invention comprises:

a correlation storage section which stores data indicating a correlation between a concentration in one urine excreted by a human and a concentration in total urine in one day when all the urine excreted by the human in the one day is gathered into one volume for each of a first specific component and a second specific component in the urine excreted by the human;

a data input section which inputs data indicating a concentration of the first specific component and a concentration of the second specific component in one urine excreted by a subject; and a calculation section which determines each of a concentration of the first specific component and a concentration of the second specific component in total urine in one day when all the urine excreted by the subject in the one day is gathered into one volume, by performing conversion using the correlation stored in the correlation storage section, based on the concentration of the first specific component and the concentration of the second specific component in the one urine of the subject obtained via the data input section, and calculates, based on the results of conversion, a concentration ratio between the first specific component and the second specific component in the total urine of the subject in the one day.

According to the urine component analysis device of the present invention, the correlation storage section stores data indicating a correlation between a concentration in one urine excreted by a human and a concentration in total urine in one day when all the urine excreted by the human in the one day is gathered into one volume for each of a first specific component and a second specific component in the urine excreted by the human. The data input section inputs data indicating a concentration of the first specific component and a concentration of the second specific component in one urine excreted by a subject. The calculation section first determines each of a concentration of the first specific component and a concentration of the second specific component in total urine in one day when all the urine excreted by the subject in the one day is gathered into one volume, by performing conversion using the correlation stored in the correlation storage section, based on the concentration of the first specific component and the concentration of the second specific component in the one urine of the subject obtained via the data input section. The calculation section further calculates, based on results of the conversion, a concentration ratio between the first specific component and the second specific component in the total urine of the subject in the one day.

Here, in the urine component analysis device, a concentration of the first specific component and a concentration of the second specific component in total urine in one day are each determined by performing conversion based on a concentration of the first specific component and a concentration of the second specific component in one urine excreted by the subject, and therefore it is not necessary to actually measure an amount of urine excreted by the subject. When a concentration of the first specific component and a concentration of the second specific component in at least one urine excreted by the subject are obtained as input data, a result of conversion is obtained. Therefore, according to the urine component analysis device, a concentration ratio between two specific components in total urine excreted by the subject in one day can be easily and conveniently determined.

In the urine component analysis device of one embodiment, the correlation storage section stores data indicating a correlation between an average concentration obtained by averaging the concentration in plural urines excreted by the human over one day or plural days and a concentration in total urine in one day or plural days when all the urine excreted by the human over the one day or the plural days is gathered into one volume for each of the first specific component and the second specific component;

the data input section inputs data indicating a concentration of the first specific component and a concentration of the second specific component in plural urines excreted by the subject over one day or plural days; and the calculation section obtains an average concentration by averaging, for each of the first specific component and the second specific component, the concentration in the plural urines excreted by the subject over one day or plural days, and defines the average concentration as an object for the conversion.

In the urine component analysis device of this embodiment, the correlation storage section stores data indicating a correlation between an average concentration obtained by averaging the concentration in plural urines excreted by the human over one day or plural days and a concentration in total urine in one day or plural days when all the urine excreted by the human over the one day or the plural days is gathered into one volume for each of the first specific component and the second specific component. The data input section inputs data indicating a concentration of the first specific component and a concentration of the second specific component in plural urines excreted by the subject over one day or plural days. The calculation section obtains an average concentration by averaging, for each of the first specific component and the second specific component, the concentration in the plural urines excreted by the subject over one day or plural days, and defines the average concentration as an object for the conversion. That is, the calculation section first determines a concentration of the first specific component and a concentration of the second specific component in total urine in one day when all the urine excreted by the subject in the one day is gathered into one volume, by performing conversion using the correlation stored in the correlation storage section, based on the obtained average concentration of the first specific component and average concentration of the second specific component. The calculation section further calculates a concentration ratio between the first specific component and the second specific component in the total urine of the subject in the one day based on the results of conversion. In this case, accuracy of the calculated concentration ratio between the first specific component and the second specific component in the total urine in the one day is enhanced.

In the urine component analysis device of one embodiment, the correlation storage section stores data indicating a correlation between an average concentration obtained by averaging the concentration in plural urines excreted by the human over one day or plural days and a concentration serving as a basis for each of the first specific component and the second specific component;

the concentration serving as a basis is obtained by determining an average value of the concentration per day for the urine excreted by the human, and averaging the average value of the concentration per day over plural days;

the data input section inputs data indicating a concentration of the first specific component and a concentration of the second specific component in plural urines excreted by the subject over one day or plural days; and the calculation section obtains an average concentration by averaging, for each of the first specific component and the second specific component, the concentration in the plural urines excreted by the subject over one day or plural days, and defines the average concentration as an object for the conversion.

In the urine component analysis device of this embodiment, the correlation storage section stores data indicating a correlation between an average concentration obtained by averaging the concentration in plural urines excreted by the human over one day or plural days and a concentration serving as a basis for each of the first specific component and the second specific component. The data input section inputs data indicating a concentration of the first specific component and a concentration of the second specific component in plural urines excreted by the subject over one day or plural days. The calculation section obtains an average concentration by averaging, for each of the first specific component and the second specific component, the concentration in the plural urines excreted by the subject over one day or plural days, and defines the average concentration as an object for the conversion. That is, the calculation section first determines a concentration of the first specific component and a concentration of the second specific component in total urine in one day when all the urine excreted by the subject in the one day is gathered into one volume, by performing conversion using the correlation stored in the correlation storage section, based on the obtained average concentration of the first specific component and average concentration of the second specific component. The calculation section further calculates a concentration ratio between the first specific component and the second specific component in the total urine of the subject in the one day based on the results of conversion. In this case, accuracy of the calculated concentration ratio between the first specific component and the second specific component in the total urine in the one day is enhanced. Furthermore, the concentration serving as a basis is obtained by determining an average value of the concentration per day for the urine excreted by the human, and averaging the average value of the concentration per day over plural days. That is, when the correlation is determined for urine over plural days, the urine may be gathered every day to determine an average value per day of concentrations of the first specific component and an average value per day of concentrations of the second specific component without the necessity to gather all the urine excreted by a human over plural days into one volume. Accordingly, the correlation can be easily acquired.

In the urine component analysis device of one embodiment, the one urine or the plural urines are one of first urine after wake-up, second urine after wake-up and urine just before sleep; and the calculation section uses the correlation corresponding to whether the one urine or the plural urines are the first urine after wake-up or the second urine after wake-up or the urine just before sleep.

In this specification, the "urine just before sleep" refers to the last one urine excreted by the subject before sleep.

In the urine component analysis device of this embodiment, the one urine or the plural urines are one of first urine after wake-up, second urine after wake-up and urine just before sleep. The calculation section uses the correlation corresponding to whether the one urine or the plural urines are the first urine after wake-up or the second urine after wake-up or the urine just before sleep. In this case, accuracy of the calculated concentration ratio between the first specific component and the second specific component in the total urine in the one day is further enhanced.

The urine component analysis device of one embodiment further comprises a urine specification section which inputs information indicating whether the one urine or the plural urines excreted by the subject are the first urine after wake-up or the second urine after wake-up or the urine just before sleep.

In the urine component analysis device of this embodiment, a user (may be identical to the subject or may be one who operates the device for the subject) can input, via a urine specification section, information indicating whether the one urine or the plural urines excreted by the subject are the first urine after wake-up or the second urine after wake-up or the urine just before sleep. By input of the information, whether the one urine or the plural urines excreted by the subject are the first urine after wake-up or the second urine after wake-up or the urine just before sleep is specified. As a result, among correlations stored in the correlation storage section, the calculation section can select and use a correlation corresponding to whether the one urine or the plural urines are the first urine after wake-up or the second urine after wake-up or the urine just before sleep.

In the urine component analysis device of one embodiment, the data input section inputs data about concentrations of the first specific component and the second specific component in real time. The urine component analysis device further comprises a urine determination section which determines whether the one urine or the plural urines excreted by the subject are the first urine after wake-up or the second urine after wake-up or the urine just before sleep, in accordance with a time at which the data about concentrations of the first specific component and the second specific component is input.

In this specification, the "data about concentrations of the first specific component and the second specific component" includes data indicating a concentration of the first specific component and a concentration of the second specific component or a concentration ratio between the first specific component and the second specific component, and may further include data for correcting the concentrations and concentration ratio.

The phrase "data is input in real time" means that data is input substantially synchronization with the date and time of urine discharge by the subject.

In the urine component analysis device of this embodiment, the data input section inputs data about concentrations of the first specific component and the second specific component in real time. The urine determination section determines whether the one urine or the plural urines excreted by the subject are the first urine after wake-up or the second urine after wake-up or the urine just before sleep, in accordance with a time at which the data about concentrations of the first specific component and the second specific component is input. By this result of determination, whether the one urine or the plural urines excreted by the subject are the first urine after wake-up or the second urine after wake-up or the urine just before sleep is specified. As a result, among correlations stored in the correlation storage section, the calculation section can select and use a correlation corresponding to whether the one urine or the plural urines are the first urine after wake-up or the second urine after wake-up or the urine just before sleep. In this way, time and labor of inputting urine specification information by the user can be saved.

The urine component analysis device of one embodiment further comprises a sleep time zone setting section for setting a sleep time zone during which the subject gets sleep. The urine determination section determines whether the one urine or the plural urines excreted by the subject are the first urine after wake-up or the second urine after wake-up or the urine just before sleep, by comparing a time, at which the data about concentrations of the first specific component and the second specific component is input, with the sleep time zone.

In the urine component analysis device of this embodiment, the user can set, via the sleep time zone setting section, a sleep time zone during which the subject gets sleep. When a sleep time zone is set as described above, the urine determination section determines whether the one urine or the plural urines excreted by the subject are the first urine after wake-up or the second urine after wake-up or the urine just before sleep, by comparing a time, at which the data about concentrations of the first specific component and the second specific component is input, with the sleep time zone. Accordingly, accuracy of determination by the urine determination section is enhanced.

The urine component analysis device of one embodiment further comprises a measurement data storage section which stores, as measurement data about the subject, a concentration ratio between the first specific component and the second specific component in each one urine over the one day or the plural days, which is obtained via the data input section, in correspondence with a measurement date and time at which each concentration ratio is measured.

In the urine component analysis device of this embodiment, the measurement data storage section stores, as measurement data about the subject, a concentration ratio between the first specific component and the second specific component in each one urine over the one day or the plural days, which is obtained via the data input section, in correspondence with a measurement date and time at which each concentration ratio is measured. Accordingly, the calculation section can obtain the result of conversion using measurement data about the subject stored in the measurement data storage section.

In the urine component analysis device of one embodiment, the calculation section selects, as an object for the conversion, data of two or more measurements in mutually different time zones in mutually different days among measurement data about the subject stored in the measurement data storage section.

In this specification, the "time zone" refers to a time zone obtained by dividing a day into two or more segments, and refers to, for example, a time zone of every hour, every two hours or every three hours.

In the urine component analysis device of this embodiment, the calculation section selects, as an object for the conversion, data of two or more measurements in mutually different time zones in mutually different days among measurement data about the subject stored in the measurement data storage section. As a result, accuracy of conversion is enhanced.

In the urine component analysis device of one embodiment, the number of measurements is at least 5.

In the urine component analysis device of this embodiment, the number of measurements is at least 5. That is, the calculation section selects, as an object for the conversion, data of at least five measurements in mutually different time zones in mutually different days among measurement data about the subject stored in the measurement data storage section. As a result, accuracy of conversion is enhanced. When data of at least five measurements is used, accuracy of conversion is almost saturated. Therefore, for example, when it is provided beforehand that data of at least five measurements is used, the subject can avoid taking excessive time and labor for urine discharge and measurement.

In the urine component analysis device of one embodiment, the mutually different days include at least seven days.

In the urine component analysis device of this embodiment, the mutually different days include at least seven days. That is, the calculation section selects, as an object for the conversion, data of two or more measurements in mutually different time zones in at least seven mutually different days among measurement data about the subject stored in the measurement data storage section. As a result, accuracy of conversion is enhanced. The reason why measurement data in at least seven days is selected is that one week (seven days) constitutes a cycle of life (including dietary life) for many people.

In the urine component analysis device of one embodiment, the mutually different days include mutually different days of week.

In the urine component analysis device of this embodiment, the mutually different days include mutually different days of week. That is, the calculation section selects, as an object for the conversion, data of two or more measurements in mutually different time zones in mutually different days of week among measurement data about the subject stored in the measurement data storage section. As a result, accuracy of conversion is enhanced. The reason why measurement data in mutually different days of week is selected is that one week (seven days) constitutes a cycle of life (including dietary life) for many people.

In the urine component analysis device of one embodiment, the calculation section includes, as the selected data of two or more measurements, the last measured concentration ratio between the first specific component and the second specific component in one urine among measurement data about the subject stored in the measurement data storage section.

In the urine component analysis device of this embodiment, the calculation section includes, as the selected data of two or more measurements, the last measured concentration ratio between the first specific component and the second specific component in one urine among measurement data about the subject stored in the measurement data storage section. As a result, the result of conversion obtained by the calculation section reflects the latest health conditions of the subject.

In the urine component analysis device of one embodiment, the measurement data storage section stores, as measurement data about the subject, a concentration ratio between the first specific component and the second specific component in each one urine over the one day or the plural days, which is obtained via the data input section, in correspondence with urine discharge date and time by the subject in addition to the measurement date and time at which each concentration ratio is measured.

In the urine component analysis device of this embodiment, the measurement data storage section stores, as measurement data about the subject, a concentration ratio between the first specific component and the second specific component in each one urine over the one day or the plural days, which is obtained via the data input section, in correspondence with urine discharge date and time by the subject in addition to the measurement date and time at which each concentration ratio is measured. Therefore, for example, a manner of use is possible in which the subject stores his or her excreted urine on a temporary basis, and thereafter the subject measures a concentration ratio between the first specific component and the second specific component of the urine, and inputs a urine discharge date and time of the urine before or after the measurement. A manner of use is also possible in which the subject discharges the urine and performs measurement at the same time, and the measurement data storage section simultaneously stores a concentration ratio between the first specific component and the second specific component which is obtained via the data input section.

The urine component analysis device of one embodiment further comprises a urine discharge history notification section which gives a notification of a history of urine discharge date and time by the subject in a period of the one day or the plural days based on the urine discharge date and time stored in the measurement data storage section.

In the urine component analysis device of this embodiment, the urine discharge history notification section gives a notification of a history of urine discharge date and time by the subject in a period of the one day or the plural days based on the urine discharge date and time stored in the measurement data storage section. In this way, the user (may be a subject as described previously) can recognize a day of week and a time zone during which the subject did not discharge urine and perform measurement in the past. Therefore, the subject can keep it in mind to discharge urine and perform measurement hereafter in a day of week and a time zone during which the subject did not discharge urine and perform measurement in the past.

In the urine component analysis device of one embodiment, the urine discharge history notification section comprises a histogram preparation section which prepares a histogram indicating a number of urine discharges by the subject for each day of week or each time zone based on the urine discharge date and time stored in the measurement data storage section.

In the urine component analysis device of this embodiment, the histogram preparation section in the urine discharge history notification section prepares a histogram indicating a number of urine discharges by the subject for each day of week or each time zone based on the urine discharge date and time stored in the measurement data storage section. By seeing the histogram, the user can intuitively recognize through visual sensation a day of week and a time zone during which the subject did not discharge urine and perform measurement in the past.

The urine component analysis device of one embodiment further comprises a urine discharge date and time input section for inputting the urine discharge date and time.

In the urine component analysis device of this embodiment, the urine discharge date and time input section for inputting the urine discharge date and time is provided. Therefore, the user can easily input a urine discharge date and time via the urine discharge date and time input section.

In the urine component analysis device of one embodiment, the data input section inputs in real time the concentration ratio between the first specific component and the second specific component in each one urine; and the measurement data storage section stores the urine discharge date and time in correspondence with a date and time at which the concentration ratio between the first specific component and the second specific component in each one urine is input by the data input section.

In the urine component analysis device of this embodiment, the data input section inputs the concentration ratio between the first specific component and the second specific component in each one urine in real time, in other words, in substantially synchronization with the urine discharge date and time by the subject. The measurement data storage section stores the urine discharge date and time in correspondence with a date and time at which the concentration ratio between the first specific component and the second specific component in each one urine is input by the data input section. In this way, time and labor of inputting the urine discharge date and time by the user can be saved.

The urine component analysis device of one embodiment further comprises:

a first urine discharge recommendation date and time determination section which determines a urine discharge recommendation date and time for the subject to discharge urine, based on the urine discharge date and time stored in the measurement data storage section, so that measurement data about the subject can be obtained in mutually different time zones of the one day or in mutually different time zones in mutually different days of the plural days; and a urine discharge recommendation date and time notification section which gives a notification of the determined urine discharge recommendation date and time.

In the urine component analysis device of this embodiment, the first urine discharge recommendation date and time determination section determines a urine discharge recommendation date and time for the subject to discharge urine, based on the urine discharge date and time stored in the measurement data storage section, so that measurement data about the subject can be obtained in mutually different time zones of the one day or in mutually different time zones in mutually different days of the plural days. The urine discharge recommendation date and time notification section gives a notification of the determined urine discharge recommendation date and time. In this way, the subject is encouraged to discharge urine and perform measurement hereafter in a day of week and a time zone during which the subject did not discharge urine and perform measurement in the past.

The urine component analysis device of one embodiment further comprises:

a second urine discharge recommendation date and time determination section which determines a urine discharge recommendation date and time for the subject to discharge urine during one day or plural days in future; and a urine discharge recommendation date and time notification section which gives a notification of the determined urine discharge recommendation date and time.

Here, it is meant that "one day or plural days in future" may include a day to which the current time belongs as long as the current time is earlier than the wake-up time.

In the urine component analysis device of this embodiment, The second urine discharge recommendation date and time determination section which determines a urine discharge recommendation date and time for the subject to discharge urine during one day or plural days in future. The urine discharge recommendation date and time notification section gives a notification of the determined urine discharge recommendation date and time. In this way, the subject can know a urine discharge recommendation date and time at which the urine should be discharged during one day or plural days in future.

In the urine component analysis device of one embodiment, the urine discharge recommendation date and time notification section executes an operation to sound an alarm at the urine discharge recommendation date and time.

In the urine component analysis device of this embodiment, the urine discharge recommendation date and time notification section executes an operation to sound an alarm at the urine discharge recommendation date and time. Therefore, the subject is encouraged to discharge urine and perform measurement at a date and time when the alarm is sounded.

In the urine component analysis device of one embodiment, the urine discharge recommendation date and time notification section executes an operation to send to the subject a mail to encourage the subject to discharge urine at the urine discharge recommendation date and time.

In the urine component analysis device of this embodiment, the urine discharge recommendation date and time notification section executes an operation to send to the subject a mail to encourage the subject to discharge urine at the urine discharge recommendation date and time. Therefore, the subject is encouraged to discharge urine and perform measurement at a date and time when the mail is received on, for example, the subject's mobile phone or smart phone.

The urine component analysis device of one embodiment further comprises a notification prohibition time zone setting section for setting a notification prohibition time zone during which an operation of the urine discharge recommendation date and time notification section should be prohibited. The urine discharge recommendation date and time notification section prohibits the operation when the urine discharge recommendation date and time belongs to the notification prohibition time zone.

In the urine component analysis device of this embodiment, the user can set, via the notification prohibition time zone setting section, a notification prohibition time zone during which operation of the urine discharge recommendation date and time notification section should be prohibited. For example, a time zone during which the subject sleeps is set as the notification prohibition time zone. In this way, a situation can be avoided in which the subject is forced to discharge urine by the urine discharge recommendation date and time notification section in a time zone during which the subject sleeps.

The urine component analysis device of one embodiment further comprises a sensor section which comes into contact with urine excreted by the subject to acquire data about concentrations of the first specific component and the second specific component.

In the urine component analysis device of this embodiment, the sensor section comes into contact with urine excreted by the subject to acquire data about concentrations of the first specific component and the second specific component. Concentrations of the first specific component and the second specific component, which are acquired by the sensor section are input by the data input section to become an object to be converted by the calculation section.

The urine component analysis device of one embodiment further comprises a calculation result storage section which stores a concentration ratio between the first specific component and the second specific component calculated by the calculation section.

In the urine component analysis device of this embodiment, the calculation result storage section stores a concentration ratio between the first specific component and the second specific component calculated by the calculation section. Therefore, the user can easily know a concentration ratio between the first specific component and the second specific component in the total urine of the subject in the one day by reading the contents of the calculation result storage section. Particularly, when a concentration ratio between the first specific component and the second specific component in total urine of the subject in one day is daily stored in the calculation result storage section, the user can easily know a tendency of daily change in concentration ratio between the first specific component and the second specific component.

The urine component analysis device of one embodiment further comprises a calculation result notification section which gives a notification of a concentration ratio between the first specific component and the second specific component calculated by the calculation section.

In the urine component analysis device of this embodiment, the calculation result notification section gives a notification of a concentration ratio between the first specific component and the second specific component calculated by the calculation section. Therefore, the user can easily know a concentration ratio between the first specific component and the second specific component in total urine of the subject in one day by receiving a notification from the calculation result notification section.

The urine component analysis device of one embodiment further comprises a housing including at least the correlation storage section, the data input section and the calculation section. The sensor section is attached to the housing so as to be projected to outside from the housing.

The urine component analysis device of this embodiment comprises a housing including at least the correlation storage section, the data input section and the calculation section. The sensor section is attached to the housing so as to be projected to outside from the housing. Accordingly, a hand-held type urine component analysis device that is used by the user with the housing held in the hand is constituted.

For example, when the hand-held type urine component analysis device is used, urine is spritzed on the sensor section with the housing held in the hand when the subject as a user discharges the urine. In this way, the sensor section comes into contact with urine excreted by the subject to acquire data about concentrations of the first specific component and the second specific component.

Alternatively, when the subject as a user discharges urine, the subject may collect a part of one urine in a disposable paper cup, and immerse the sensor section in the urine in the paper cup with the housing held in the hand.

Alternatively, when the subject as a user discharges urine, the subject may infiltrate a part of one urine into a sheet of toilet paper, and bring the sensor section into contact with the urine infiltrated in the sheet of toilet paper with the housing held in the hand.

Alternatively, when the subject as a user discharges urine, the subject may store urine in a toilet bowl, and immerse the sensor section in the urine stored in the toilet bowl with the housing held in the hand. Even if water exists in the toilet bowl to dilute urine, dilution of urine does not itself affect the obtained calculation result (concentration ratio).

In any case, according to the hand-held type urine component analysis device, a calculation result is obtained by simple operations.

The urine component analysis device of one embodiment further comprises a housing including at least the correlation storage section, the data input section and the calculation section. The housing is disposed on a circumference of a toilet bowl or in a room provided with a toilet bowl. Furthermore, the sensor section is disposed in a space inside the toilet bowl.

The urine component analysis device of this embodiment comprises a housing including at least the correlation storage section, the data input section and the calculation section. The housing is disposed on a circumference of a toilet bowl or in a room provided with a toilet bowl. Furthermore, the sensor section is disposed in a space inside the toilet bowl. Accordingly, a toilet bowl-mounted type urine component analysis device can be formed.

For example, when the toilet bowl-mounted type urine component analysis device is used, urine is spritzed on the sensor section in a space inside the toilet bowl when the subject as a user discharges urine. In this way, the sensor section comes into contact with urine excreted by the subject to acquire data about concentrations of the first specific component and the second specific component. According to the toilet bowl-mounted type urine component analysis device, the subject as a user is not required to provide a container to store urine, such as a paper cup.

In this specification, the phrase "the housing is disposed "on the circumference of a toilet bowl" includes a case where the housing is attached on a toilet bowl or its annexed equipment (water tank etc.) and a case where the housing is incorporated integrally with a toilet bowl or its annexed equipment.

The urine component analysis device of one embodiment further comprises a housing including at least the correlation storage section, the data input section and the calculation section. The data input section inputs data about concentrations of the first specific component and the second specific component via a wireless or wired communication line from the outside of the housing. Furthermore, the housing further includes a calculation result sending section which sends a concentration ratio between the first specific component and the second specific component calculated by the calculation section to outside the housing via a wireless or wired communication line.

The urine component analysis device of this embodiment comprises a housing including at least the correlation storage section, the data input section and the calculation section. The data input section inputs data about concentrations of the first specific component and the second specific component via a wireless or wired communication line from the outside of the housing. Furthermore, the housing further includes a calculation result sending section which sends a concentration ratio between the first specific component and the second specific component calculated by the calculation section to outside the housing via a wireless or wired communication line. Accordingly, a server type urine component analysis device that performs input of data and output of a calculation result via a wireless or wired communication line can be formed.

For example, when the server type urine component analysis device is used, the subject as a user at a remote location away from the housing acquires data about concentrations of the first specific component and the second specific component by a commercially available sensor etc. The data is input by the data input section via a wireless or wired communication line from a mobile phone or personal computer which is operated by the subject. As a result, a concentration ratio between the first specific component and the second specific component in total urine in one day when all the urine excreted by the subject in the one day is gathered into one volume is calculated by the calculation section. The concentration ratio between the first specific component and the second specific component calculated by the calculation section is output to the mobile phone or personal computer of the subject at a remote location away from the housing via the wireless or wired communication line by the calculation result sending section. As a result, the subject can know a concentration ratio between the first specific component and the second specific component calculated by the calculation section, through a display screen of the mobile phone or personal computer, at a location where the subject is present.

Thus, the server type urine component analysis device can be easily used by a user at a remote location away from the housing.

The urine component analysis device of one embodiment further comprises a personal authentication section for identifying the subject.

The urine component analysis device of this embodiment comprises a personal authentication section for identifying the subject. Therefore, by discriminating measurement data about the subject on an individual basis, the urine component analysis device can be shared by two or more subjects.

In the urine component analysis device of one embodiment, the first specific component and the second specific component are each one of sodium, potassium, calcium and glucose, the first and second specific components being mutually different.

In the urine component analysis device of this embodiment, the first specific component and the second specific component are each one of sodium, potassium, calcium and glucose, the first and second specific components being mutually different. Therefore, the concentration ratio between the first specific component and the second specific component in total urine of the subject in one day, which is obtained by the calculation section, can be used as useful information for improving the dietary life of the subject. Particularly, when the first specific component is sodium and the second specific component is potassium, and therefore the concentration ratio between the first specific component and the second specific component in total urine of the subject in one day, which is obtained by the calculation section, is a Na/K ratio, the Na/K ratio can be used as information about hypertension of the subject.

The urine component analysis device of one embodiment further comprises:

an advice table which stores a concentration ratio between sodium as the first specific component and potassium as the second specific component in correspondence with an advice appropriate to the concentration ratio for the subject; and an advice section which selects an advice appropriate to the concentration ratio between sodium as the first specific component and potassium as the second specific component, which is calculated by the calculation section, by referring to the advice table.

Here, for example, the "advice" may be an advice about hypertension of the subject.

The urine component analysis device of this embodiment comprises an advice table which stores a concentration ratio between sodium as the first specific component and potassium as the second specific component in correspondence with an advice appropriate to the concentration ratio for the subject. The advice section selects an advice appropriate to the concentration ratio between sodium as the first specific component and potassium as the second specific component, which is calculated by the calculation section, by referring to the advice table. Therefore, for example, an advice about hypertension of the subject can be given in accordance with the concentration ratio (Na/K ratio) between sodium as the first specific component and potassium as the second specific component, which is obtained by the calculation section.

In another aspect, the urine component analysis method of the present invention comprises:

storing in a predetermined storage section data indicating a correlation between a concentration ratio between a first specific component and a second specific component in one urine excreted by a human and a concentration ratio between the first specific component and the second specific component in total urine in one day when all the urine excreted by the human in the one day is gathered into one volume;

inputting data indicating a concentration ratio between the first specific component and the second specific component in one urine excreted by a subject; and determining a concentration ratio between the first specific component and the second specific component in total urine in one day when all the urine excreted by the subject in the one day is gathered into one volume, by performing conversion using the correlation stored in the storage section, based on the input concentration ratio between the first specific component and the second specific component in the one urine of the subject.

According to the urine component analysis method, a concentration ratio between the first specific component and the second specific component in total urine in one day is determined by performing conversion based on a concentration ratio between the first specific component and the second specific component in one urine excreted by the subject, and therefore it is not necessary to actually measure an amount of urine excreted by the subject. When a concentration ratio between the first specific component and the second specific component in at least one urine excreted by the subject is obtained as input data, a result of conversion is obtained. Therefore, according to the urine component analysis device, a concentration ratio between two specific components in total urine excreted by the subject in one day can be easily and conveniently determined.

In another aspect, the urine component analysis method of the present invention comprises:

storing in a predetermined storage section data indicating a correlation between a concentration in one urine excreted by a human and a concentration in total urine in one day when all the urine excreted by the human in the one day is gathered into one volume for each of a first specific component and a second specific component in the urine excreted by the human;

inputting data indicating a concentration of the first specific component and a concentration of the second specific component in one urine excreted by a subject; and determining each of a concentration of the first specific component and a concentration of the second specific component in total urine in one day when all the urine excreted by the subject in the one day is gathered into one volume, by performing conversion using the correlation stored in the storage section, based on the input concentration of the first specific component and the input concentration of the second specific component in the one urine of the subject, and calculating, based on the results of calculation, a concentration ratio between the first specific component and the second specific component in the total urine of the subject in the one day.

According to the urine component analysis method, a concentration of the first specific component and a concentration of the second specific component in total urine in one day are each determined by performing conversion based on a concentration of the first specific component and a concentration of the second specific component in one urine excreted by the subject, and therefore it is not necessary to actually measure an amount of urine excreted by the subject. When a concentration of the first specific component and a concentration of the second specific component in at least one urine excreted by the subject are obtained as input data, a result of conversion is obtained. Therefore, according to the urine component analysis device, a concentration ratio between two specific components in total urine excreted by the subject in one day can be easily and conveniently determined.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A urine component analysis device for determining a concentration ratio between two specific components in total urine excreted by a subject in one day, the device comprising:
 a sensor section that comes into contact with urine excreted by the subject and is configured to acquire data about concentrations of a first specific component and a second specific component;
 a correlation storage section comprising a non-transitory memory which stores data indicating a correlation between a concentration ratio between the first specific component and the second specific component in one urine excreted by a human and a concentration ratio between the first specific component and the second specific component in total urine in one day when all the urine excreted by the human in the one day is gathered into one volume;
 a data input section which inputs data acquired by the sensor and indicating a concentration ratio between the first specific component and the second specific component in one urine excreted by the subject;
 a calculation section comprising a processor that is programmed with instructions for carrying out the instructions to determine a concentration ratio between the first specific component and the second specific component in total urine in one day when all the urine excreted by the subject in the one day is gathered into one volume, by performing conversion using the correlation stored in the non-transitory memory of the correlation storage section, based on the concentration ratio between the first specific component and the second specific component in the one urine of the subject obtained via the data input section; and
 a housing including at least the correlation storage section, the data input section and the calculation section, wherein the sensor section is attached to the housing so as to be projected outside from the housing.

2. The urine component analysis device according to claim 1,
 wherein the correlation storage section non-transitory memory stores data indicating a correlation between an average concentration ratio obtained by averaging the concentration ratio between the first specific component and the second specific component in plural urines excreted by the human over one day or plural days and a concentration ratio between the first specific component and the second specific component in total urine in one day or plural days when all the urine excreted by the human over the one day or the plural days is gathered into one volume; and
 the calculation section processor obtains an average concentration ratio by averaging the concentration ratio between the first specific component and the second specific component in the plural urines excreted by the subject over one day or plural days, and define the average concentration ratio as an object for the conversion.

3. The urine component analysis device according to claim 1,
 wherein the correlation storage section non-transitory memory stores data indicating a correlation between an average concentration ratio obtained by averaging the concentration ratio between the first specific component and the second specific component in plural urines excreted by the human over one day or plural days and a concentration ratio between the first specific component and the second specific component, which serves as a basis;
 the concentration ratio between the first specific component and the second specific component, which serves as a basis, is obtained by determining an average value per day of concentration ratios between the first specific component and the second specific component for urine excreted by the human, and averaging the average value per day over plural days; and
 the calculation section is processor obtains an average concentration ratio by averaging the concentration ratio between the first specific component and the second specific component in the plural urines excreted by the subject over one day or plural days, and defines the average concentration ratio as an object for the conversion.

4. The urine component analysis device according to claim 2,
 wherein the one urine or the plural urines are one of first urine after wake-up, second urine after wake-up and urine just before sleep; and
 the calculation section processor uses the correlation corresponding to whether the one urine or the plural urines are the first urine after wake-up or the second urine after wake-up or the urine just before sleep.

5. The urine component analysis device according to claim 4,
 wherein the urine component analysis device comprises a urine specification section which inputs information indicating whether the one urine or the plural urines excreted by the subject are the first urine after wake-up or the second urine after wake-up or the urine just before sleep.

6. The urine component analysis device according to claim 4,
wherein the data input section inputs data about concentrations of the first specific component and the second specific component in real time; and
the urine component analysis device comprises a urine determination section which determines whether the one urine or the plural urines excreted by the subject are the first urine after wake-up or the second urine after wake-up or the urine just before sleep, in accordance with a time at which the data about concentrations of the first specific component and the second specific component is input.

7. The urine component analysis device according to claim 6,
wherein the urine component analysis device comprises a sleep time zone setting section for setting a sleep time zone during which the subject gets sleep; and
the urine determination section determines whether the one urine or the plural urines excreted by the subject are the first urine after wake-up or the second urine after wake-up or the urine just before sleep, by comparing a time, at which the data about concentrations of the first specific component and the second specific component is input, with the sleep time zone.

8. The urine component analysis device according to claim 2,
wherein the urine component analysis device comprises a measurement data storage section which stores, as measurement data about the subject, a concentration ratio between the first specific component and the second specific component in each one urine over the one day or the plural days, which is obtained via the data input section, in correspondence with a measurement date and time at which each concentration ratio is measured.

9. The urine component analysis device according to claim 8,
wherein the calculation section processor selects, as an object for the conversion, data of two or more measurements in mutually different time zones in mutually different days among measurement data about the subject stored in the measurement data storage section.

10. The urine component analysis device according to claim 9,
wherein the number of measurements is at least 5.

11. The urine component analysis device according to claim 9,
wherein the mutually different days include at least seven days.

12. The urine component analysis device according to claim 9,
wherein the mutually different days include mutually different days of week.

13. The urine component analysis device according to claim 9,
wherein the calculation section processor includes, as the selected data of two or more measurements, the last measured concentration ratio between the first specific component and the second specific component in one urine among measurement data about the subject stored in the measurement data storage section.

14. The urine component analysis device according to claim 8,
wherein the measurement data storage section stores, as measurement data about the subject, a concentration ratio between the first specific component and the second specific component in each one urine over the one day or the plural days, which is obtained via the data input section, in correspondence with urine discharge date and time by the subject in addition to the measurement date and time at which each concentration ratio is measured.

15. The urine component analysis device according to claim 14, wherein the urine component analysis device comprises a urine discharge history notification section which gives a notification of a history of urine discharge date and time by the subject in a period of the one day or the plural days based on the urine discharge date and time stored in the measurement data storage section.

16. The urine component analysis device according to claim 15, wherein the urine discharge history notification section comprises a histogram preparation section which prepares a histogram indicating a number of urine discharges by the subject for each day of week or each time zone based on the urine discharge date and time stored in the measurement data storage section.

17. The urine component analysis device according to claim 14,
wherein the urine component analysis device comprises a urine discharge date and time input section for inputting the urine discharge date and time.

18. The urine component analysis device according to claim 14,
wherein the data input section inputs in real time the concentration ratio between the first specific component and the second specific component in each one urine; and
the measurement data storage section stores the urine discharge date and time in correspondence with a date and time at which the concentration ratio between the first specific component and the second specific component in each one urine is input by the data input section.

19. The urine component analysis device according to claim 14,
wherein the urine component analysis device comprises a first urine discharge recommendation date and time determination section which determines a urine discharge recommendation date and time for the subject to discharge urine, based on the urine discharge date and time stored in the measurement data storage section, so that measurement data about the subject can be obtained in mutually different time zones of the one day or in mutually different time zones in mutually different days of the plural days; and
a urine discharge recommendation date and time notification section which gives a notification of the determined urine discharge recommendation date and time.

20. The urine component analysis device according to claim 1,
wherein the urine component analysis device comprises a second urine discharge recommendation date and time determination section which determines a urine discharge recommendation date and time for the subject to discharge urine during one day or plural days in future; and
a urine discharge recommendation date and time notification section which gives a notification of the determined urine discharge recommendation date and time.

21. The urine component analysis device according to claims 19,
wherein the urine discharge recommendation date and time notification section executes an operation to sound an alarm at the urine discharge recommendation date and time.

22. The urine component analysis device according to claim 19,
wherein the urine discharge recommendation date and time notification section executes an operation to send to the subject a mail to encourage the subject to discharge urine at the urine discharge recommendation date and time.

23. The urine component analysis device according to claim 19,
wherein the urine component analysis device comprises a notification prohibition time zone setting section for setting a notification prohibition time zone during which an operation of the urine discharge recommendation date and time notification section should be prohibited; and
the urine discharge recommendation date and time notification section prohibits the operation when the urine discharge recommendation date and time belongs to the notification prohibition time zone.

24. The urine component analysis device according to claim 1,
wherein the urine component analysis device comprises a calculation result storage section which stores a concentration ratio between the first specific component and the second specific component calculated by the calculation section.

25. The urine component analysis device according to claim 1,
wherein the urine component analysis device comprises a calculation result notification section which gives a notification of a concentration ratio between the first specific component and the second specific component calculated by the calculation section.

26. A urine component analysis device for determining a concentration ratio between two specific components in total urine excreted by a subject in one day, the device comprising:
a sensor section that comes into contact with urine excreted by the subject and is configured to acquire data about concentrations of a first specific component and a second specific component;
a correlation storage section comprising a non-transitory memory which stores data indicating a correlation between a concentration ratio between the first specific component and the second specific component in one urine excreted by a human and a concentration ratio between the first specific component and the second specific component in total urine in one day when all the urine excreted by the human in the one day is gathered into one volume;
a data input section which inputs data acquired by the sensor and indicating a concentration ratio between the first specific component and the second specific component in one urine excreted by the subject;
a calculation section comprising a processor that is programmed with instructions for carrying out the instructions to determine a concentration ratio between the first specific component and the second specific component in total urine in one day when all the urine excreted by the subject in the one day is gathered into one volume, by performing conversion using the correlation stored in the non-transitory memory of the correlation storage section, based on the concentration ratio between the first specific component and the second specific component in the one urine of the subject obtained via the data input section; and
a housing including at least the correlation storage section, the data input section and the calculation section,
wherein the housing is disposed on a circumference of a toilet bowl or in a room provided with a toilet bowl; and
the sensor section is disposed in a space inside the toilet bowl.

27. The urine component analysis device according to claim 1,
wherein the data input section inputs data about concentrations of the first specific component and the second specific component via a wireless or wired communication line from the outside of the housing; and
the housing further includes a calculation result sending section which sends a concentration ratio between the first specific component and the second specific component calculated by the calculation section to outside the housing via a wireless or wired communication line.

28. The urine component analysis device according to claim 1,
wherein the urine component analysis device comprises a personal authentication section for identifying the subject.

29. The urine component analysis device according to claim 1,
wherein the first specific component and the second specific component are each one of sodium, potassium, calcium and glucose, the first and second specific components being mutually different.

30. The urine component analysis device according to claim 1,
wherein the urine component analysis device comprises an advice table which stores a concentration ratio between sodium as the first specific component and potassium as the second specific component in correspondence with an advice appropriate to the concentration ratio for the subject; and
an advice section which selects an advice appropriate to the concentration ratio between sodium as the first specific component and potassium as the second specific component, which is calculated by the calculation section, by referring to the advice table.

* * * * *